US012655203B2

(12) United States Patent
Takahashi et al.

(10) Patent No.: US 12,655,203 B2
(45) Date of Patent: Jun. 16, 2026

(54) NEUTRALIZING ANTIBODY FOR TOOTH REGENERATION TREATMENT TARGETING USAG-1 MOLECULE

(71) Applicants: Kyoto University, Kyoto (JP); University of Fukui, Fukui (JP); Osaka University, Suita (JP)

(72) Inventors: Katsu Takahashi, Kyoto (JP); Manabu Sugai, Yoshida-gun (JP); Yoshihito Tokita, Kasugai (JP); Junichi Takagi, Suita (JP); Emiko Mihara, Suita (JP)

(73) Assignees: Kyoto University, Kyoto (JP); University of Fukui, Fukui (JP); Osaka University, Suita (JP)

( * ) Notice: Subject to any disclaimer, the term of this patent is extended or adjusted under 35 U.S.C. 154(b) by 1066 days.

(21) Appl. No.: 17/625,520

(22) PCT Filed: Jul. 10, 2020

(86) PCT No.: PCT/JP2020/027127
§ 371 (c)(1),
(2) Date: Jan. 27, 2022

(87) PCT Pub. No.: WO2021/010346
PCT Pub. Date: Jan. 21, 2021

(65) Prior Publication Data

US 2022/0259298 A1 Aug. 18, 2022

(30) Foreign Application Priority Data

Jul. 12, 2019 (JP) ................................. 2019-130153
Apr. 30, 2020 (JP) ................................. 2020-080723

(51) Int. Cl.
*A61P 1/02* (2006.01)
*C07K 16/22* (2006.01)
*A61K 39/00* (2006.01)

(52) U.S. Cl.
CPC ................ *C07K 16/22* (2013.01); *A61P 1/02* (2018.01); *A61K 2039/505* (2013.01); *C07K 2317/24* (2013.01); *C07K 2317/76* (2013.01)

(58) Field of Classification Search
CPC ........................................................ A61P 1/02
See application file for complete search history.

(56) References Cited

U.S. PATENT DOCUMENTS

| | | | | |
|---|---|---|---|---|
| 11,485,787 | B2 * | 11/2022 | Dekruyff ................ | C07K 16/22 |
| 2009/0130113 | A1 | 5/2009 | Kneissel et al. | |
| 2009/0130114 | A1 | 5/2009 | Qian et al. | |
| 2012/0101005 | A1 | 4/2012 | Tatnell et al. | |
| 2013/0195856 | A1 | 8/2013 | Ellies | |
| 2022/0259298 | A1 | 8/2022 | Takahashi et al. | |

FOREIGN PATENT DOCUMENTS

| | | | |
|---|---|---|---|
| JP | 2012-530502 | A | 12/2012 |
| JP | 2014-167002 | A | 9/2014 |
| JP | 2016-121170 | A | 7/2016 |
| JP | 2021-176829 | A | 11/2021 |
| WO | 03/106657 | A2 | 12/2003 |
| WO | 03/106657 | A3 | 12/2003 |
| WO | 2018/027039 | A1 | 2/2018 |
| WO | 2018/027039 | A8 | 2/2018 |
| WO | 2021/010346 | A1 | 1/2021 |

OTHER PUBLICATIONS

Rudikoff et al. (Proceedings of the National Academy of Sciences, 1982, 79:1979-1983) (Year: 1982).*
MacCallum et al. (Journal of Molecular Biology, 1996, 262:732-745) (Year: 1996).*
Casset et al. (Biochemical and Biophysical Research Communications, 2003, 307:198-205) (Year: 2003).*
Holm et al. (Molecular Immunology, 2007:1075-1084) (Year: 2007).*
Chen et al. (Journal of Molecular Biology, 1999, 293:865-881) (Year: 1999).*
Office Action, including search report, issued in related Chinese Patent Application No. 202080063186.9 dated Aug. 25, 2023.
International Search Report issued in related International Patent Application No. PCT/JP2022/004300 dated Apr. 26, 2022.
International Preliminary Report on Patentability and Written Opinion issued in related International Patent Application No. PCT/JP2022/004300 dated Aug. 15, 2024.
Partial Supplementary European Search Report issued in corresponding European Patent Application No. 20840397.2 dated Oct. 20, 2023.
Rudikoff et al., "Single amino acid substitution altering antigen-binding specificity," PNAS, 79: 1979-1983 (1982).
De la Lastra et al., "Epitope mapping of 10 monoclonal antibodies against the pig analogue of human membrane cofactor protein (MCP)," Immunology, 96 (4): 663-670 (1999).
Yanagita, "Balance between bone morphogenetic proteins and their antagonists in kidney injury," THerapeutic Apheresis and Dialysis 11 (Supplement 1): S38-S43 (2007).
International Search Report issued in corresponding International Patent Application No. PCT/JP2020/027127 dated Sep. 24, 2020.
International Preliminary Report on Patentability issued in corresponding International Patent Application No. PCT/JP2020/027127 dated Jan. 27, 2022.
Cho et al., "Interactions between Shh Sostdc1 and Wnt signaling and a new feedback loop for spatial patterning of the teeth," Development, 138: 1807-1816 (2011).

(Continued)

*Primary Examiner* — Nelson B Moseley, II
*Assistant Examiner* — Dennis J Sullivan
(74) *Attorney, Agent, or Firm* — Morgan, Lewis & Bockius LLP

(57) ABSTRACT

Provided are: an antibody which specifically binds to and neutralizes USAG-1 or an antigen-binding fragment thereof; and a pharmaceutical composition containing the antibody or the antigen-binding fragment.

20 Claims, 22 Drawing Sheets

Specification includes a Sequence Listing.

(56) References Cited

OTHER PUBLICATIONS

Abitbol et al., "Sostdc1, a secreted dual BMP and WNT antagonist is differentially expressed in RCS rdy+ and rdy− rat retinal pigment epithelial cells," ARVO Annual Meeting Abstract, 58 (610) (Jun. 2017).
Chen et al., "Mesenchymal Wnt-beta-catenin signaling induces Wnt and BMP antagonists in dental epithelium," Organogenesis, 15 (2):55-67 (2019).
Ohazama et al., "Stem-cell-based Tissue Engineering of Murine Teeth," Journal of Dental Research, 83(7): 518-522 (2004).
Nakao et al., "The development of a bioengineered organ germ method," Nature Methods, 4 (3): 227-230 (2007).
Supplementary European Search Report dated Jan. 23, 2024, issued in corresponding European Patent Application No. 20840397.2.
Office Action dated Jun. 4, 2024, issued in corresponding Japanese Patent Application No. 2020-119469.
Office Action issued in corresponding Japanese Patent Application No. 2023-578282, dated Dec. 23, 2025.
Office Action issued in corresponding Korean Patent Application No. 10-2022-7004179, dated Dec. 16, 2025.
Office Action issued in Indian Patent Application No. 202447063666, dated Apr. 6, 2026.

* cited by examiner

[FIG. 1]
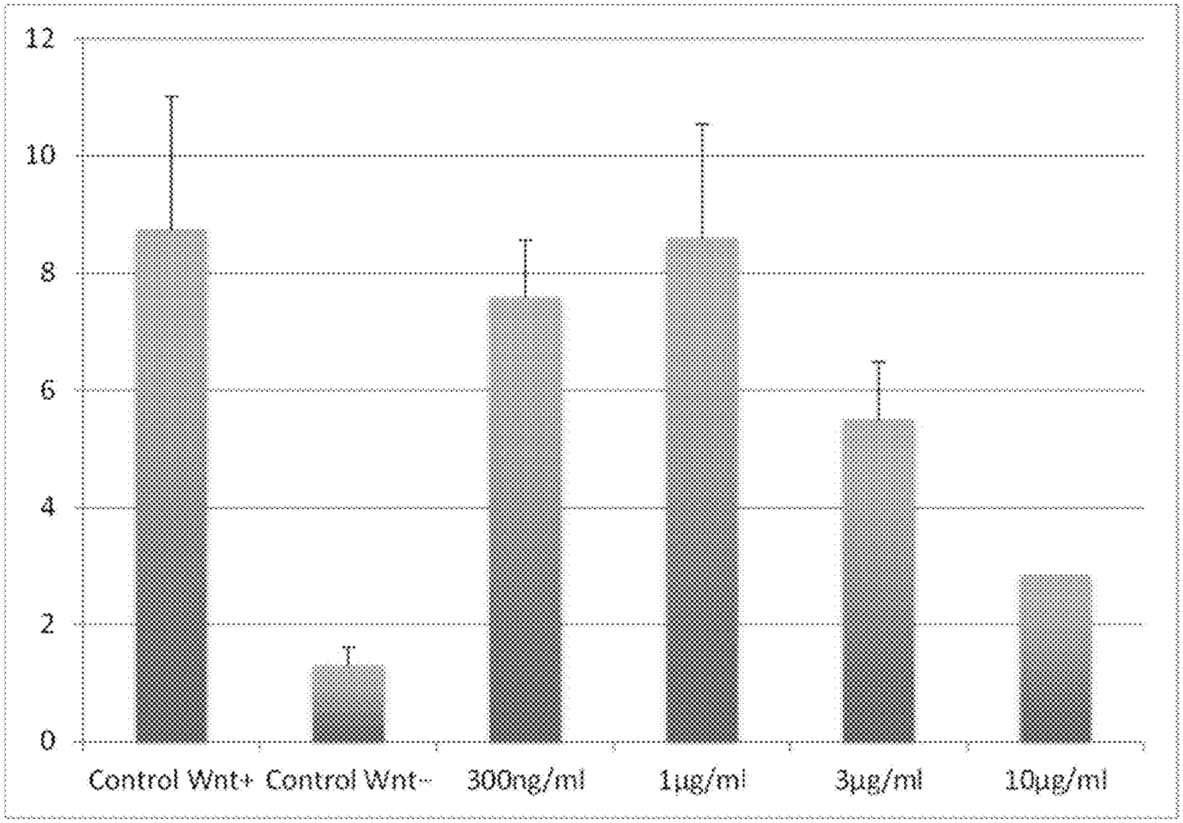

[FIG. 2]
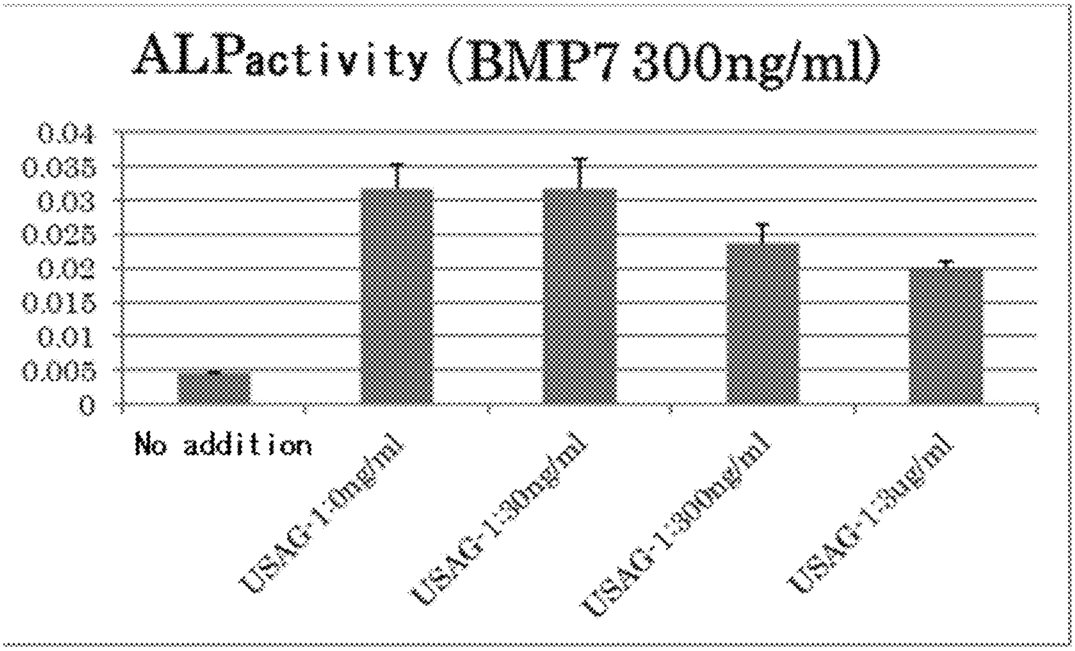

[FIG. 4-1]

| No. | ALP | BMP reporter (BRITER) | WNT(1) Sup. 25% | WNT(2) Sup.20% | WNT(2) Sup. 20% | WNT(3) Sup. 10% | WNT(3) Sup. 10% | solid phase | sandwich | | subtype |
|---|---|---|---|---|---|---|---|---|---|---|---|
| | | | | | | | | | anti-FLAG | anti-6xHis | |
| 1 | | | | | | | | 0.150 | 0.017 | 0.008 | - |
| 2 | | | | * | | | | 1.665 | 0.018 | 0.011 | G2b |
| 3 | * | | | | | | | 2.632 | 0.037 | 0.088 | G2b |
| 4 | * | * | | * | | | | 2.168 | 0.036 | 0.041 | G2b |
| 5 | | | | | | * | | 1.813 | 0.023 | 0.012 | G2b |
| 6 | | | | * | | | | over | 0.024 | 0.023 | G2b |
| 7 | | | | ** | | | | over | 0.027 | 0.029 | G2b |
| 8 | | ** | | * | | ** | | 0.469 | 0.019 | 0.007 | G1 |
| 9 | | | | | | * | | 0.180 | 0.014 | 0.006 | - |
| 10 | | | | * | | | | 2.336 | 0.036 | 0.073 | G2b |
| 11 | | | | | | | | 1.583 | 0.022 | 0.011 | G1 |
| 12 | * * * | | | | | ** | | over | 0.034 | 0.031 | G1 |
| 13 | * * | | | | | * | | over | 0.024 | 0.020 | G2b |
| 14 | | ** | | * | | | | over | 0.016 | 0.006 | G2b |
| 15 | | | | * | | | | over | 0.036 | 0.048 | G2b |
| 16 | * * | * | | * | | | | 1.011 | 0.027 | 0.063 | G1 |
| 17 | | | | | | * | | 1.694 | 0.015 | 0.007 | G2b |
| 18 | | * | | | | ** | | over | 0.018 | 0.013 | G2b |
| 19 | | | | | | ** | | 1.044 | 0.022 | 0.012 | G2b |
| 20 | * | | | * | | | | over | 0.048 | 0.044 | G2b |
| 21 | | | | | | | | 0.207 | 0.015 | 0.007 | - |
| 22 | | | | * | | | | over | 0.019 | 0.014 | G2b |
| 23 | | | | * | | * | | 1.671 | 0.020 | 0.016 | G2b |
| 24 | * * | | | * | | | | over | 0.014 | 0.007 | G2b |
| 25 | * | | | | | | | over | 0.023 | 0.025 | G2b |
| 26 | | | | * | | | | 1.914 | 0.017 | 0.009 | G1 |
| 27 | * | | | * | | | | over | 0.031 | 0.039 | G1 |
| 28 | | | | * | | | | over | 0.031 | 0.032 | G2b |
| 29 | | | | * | | | | over | 0.037 | 0.045 | G1, G2b |
| 30 | | | | | | | | over | 0.028 | 0.032 | G2b |
| 31 | | | | * | | | | over | 0.022 | 0.028 | G1, G2b |
| 32 | * | | | ** | | | | 0.214 | 0.015 | 0.007 | - |
| 33 | | | | | | ** | | 0.317 | 0.020 | 0.019 | G2b |
| 34 | | ** | | * | | * | | 1.464 | 0.015 | 0.009 | G2b |
| 35 | | | | * | | | | over | 0.072 | 0.047 | G1 |
| 36 | | * | | * | | | | 1.589 | 0.023 | 0.008 | G1 |
| 37 | * | | | * | | * | | over | 0.033 | 0.041 | G1 |
| 38 | * | | | * | | | | over | 0.027 | 0.031 | G1 |
| 39 | * | | | * | | | | 2.514 | 0.032 | 0.010 | G1 |
| 40 | | | | * | | | | 1.858 | 0.023 | 0.007 | G1 |
| 41 | | | | | | | | over | 0.037 | 0.052 | G1 |
| 42 | * | | * | | | | * | 0.736 | 0.013 | 0.009 | G2b |
| 43 | * | | | | | | * | over | 0.025 | 0.026 | G1 |
| 44 | | | * | | | | * | 0.058 | 0.016 | 0.007 | - |
| 45 | | | * | | | | * | 2.178 | 0.021 | 0.017 | G2b |
| 46 | | | | | * | | * | 2.144 | 0.021 | 0.018 | G1 |
| 47 | | | | | | | ** | 2.497 | 0.023 | 0.021 | G2a, G2b |
| 48 | | | * | | ** | | * | over | 0.026 | 0.039 | G1 |
| 49 | * | | | | | | * | 2.141 | 0.017 | 0.013 | G2b |
| 50 | * | | | | | | * | over | 0.018 | 0.012 | G1 |

[FIG. 4-2]

| | | | | | | | | | |
|---|---|---|---|---|---|---|---|---|---|
| 51 | | | | | * | over | 0.040 | 0.058 | G1, G2b |
| 52 | | ** | | * | * | 1.880 | 0.019 | 0.012 | G2a |
| 53 | | | * | | * | 0.987 | 0.016 | 0.007 | G2b |
| 54 | | | | | ** | over | 0.035 | 0.043 | G1 |
| 55 | | | | | * | 1.266 | 0.020 | 0.018 | G1 |
| 56 | | | | * | * | over | 0.020 | 0.018 | G1 |
| 57 | | | ** | | ** | over | 0.036 | 0.054 | G1 |
| 58 | | | | | * | over | 0.027 | 0.025 | G2a |
| 59 | | | | | * | over | 0.047 | 0.071 | G1 |
| 60 | | | | | * | over | 0.023 | 0.021 | G2a |
| 61 | | | | | ** | 1.290 | 0.017 | 0.011 | G2a |
| 62 | | | | | * | over | 0.048 | 0.067 | G1, G2b |
| 63 | | | | | | over | 0.031 | 0.039 | G2a, G2b |
| 64 | | | * | * | | 1.243 | 0.014 | 0.008 | G1 |
| 65 | | | * | | * | over | 0.035 | 0.045 | G1 |
| 66 | | | * | | * | over | 0.026 | 0.032 | G1, G2b |
| 67 | | | * | | * | over | 0.023 | 0.031 | G2b |
| 68 | | | | | | 2.849 | 0.019 | 0.013 | G1 |
| 69 | | | * | | | 2.784 | 0.019 | 0.011 | G1 |
| 70 | | | | | * | over | 0.043 | 0.062 | G1 |
| 71 | | | | * | * | 0.731 | 0.017 | 0.010 | G2b |
| 72 | | | * | ** | * | 0.749 | 0.015 | 0.009 | G2b |
| 73 | * * | | | | ** | over | 0.014 | 0.007 | G2b |
| 74 | | | | | | 1.536 | 0.017 | 0.009 | G2b |
| 75 | * | | | | * | over | 0.017 | 0.014 | G1 |
| 76 | * * * | | | | | 2.451 | 0.023 | 0.033 | G1 |
| 77 | * * | | | | * | over | 0.032 | 0.043 | G1 |
| 78 | * * * | | | | * | 1.460 | 0.024 | 0.023 | G2a |
| 79 | | | | | | 0.784 | 0.016 | 0.008 | G2b |
| P.C. | | | | | | over | 0.028 | 0.033 | |
| N.C. | | | | | | 0.004 | 0.015 | 0.014 | |

[FIG. 5]
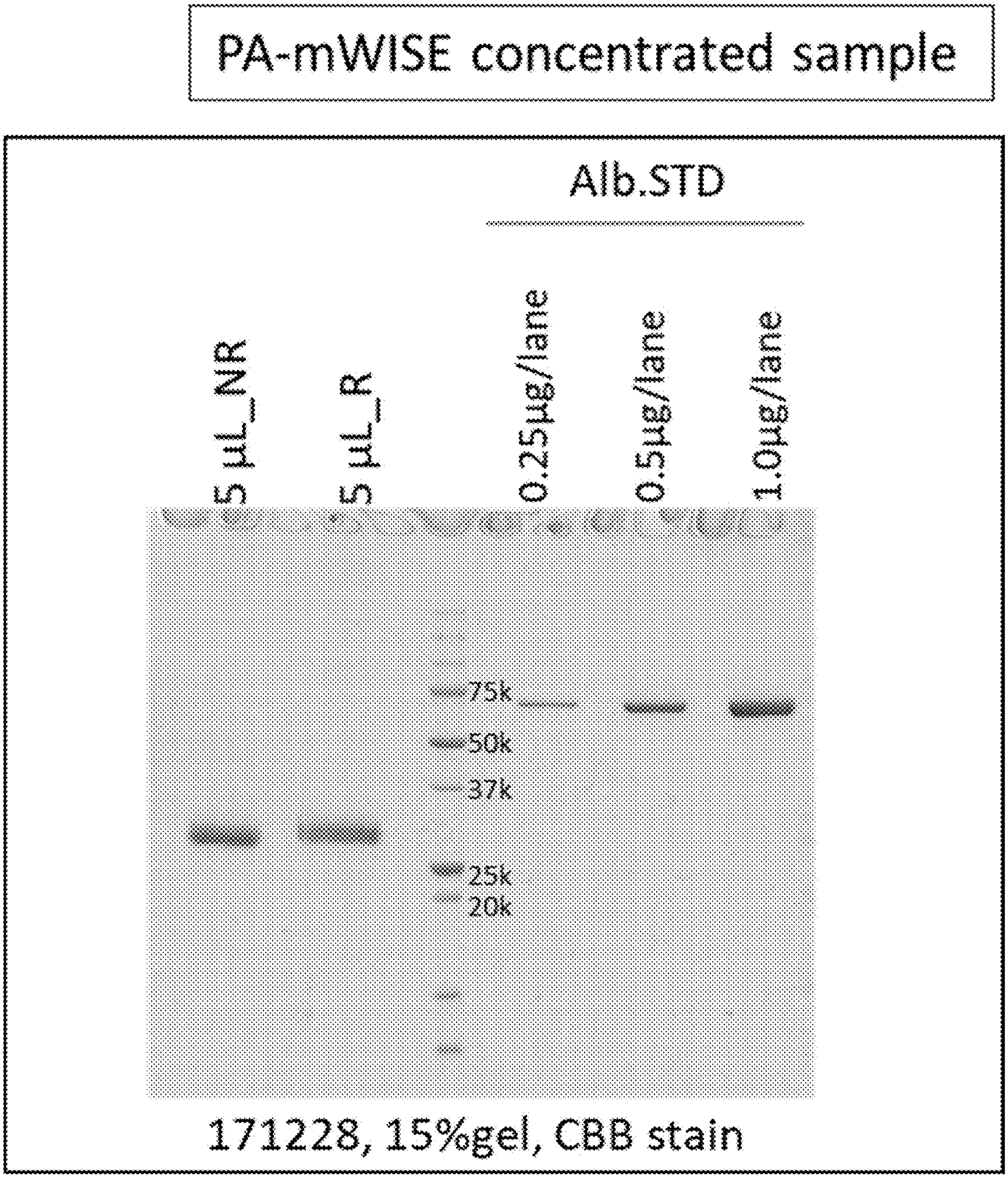

[FIG. 6]
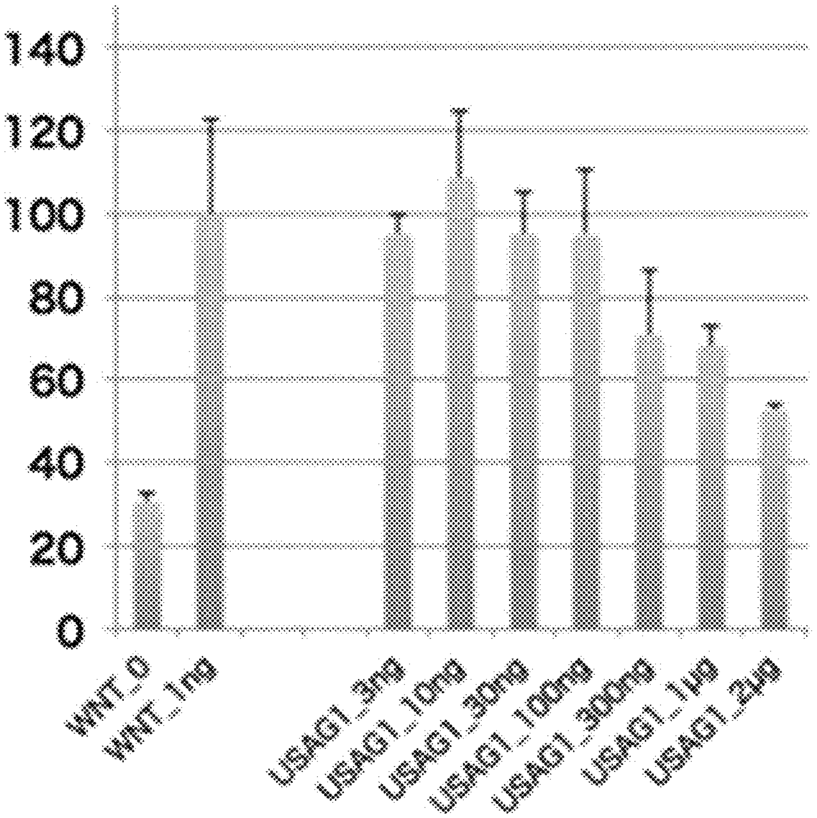
[FIG. 7]
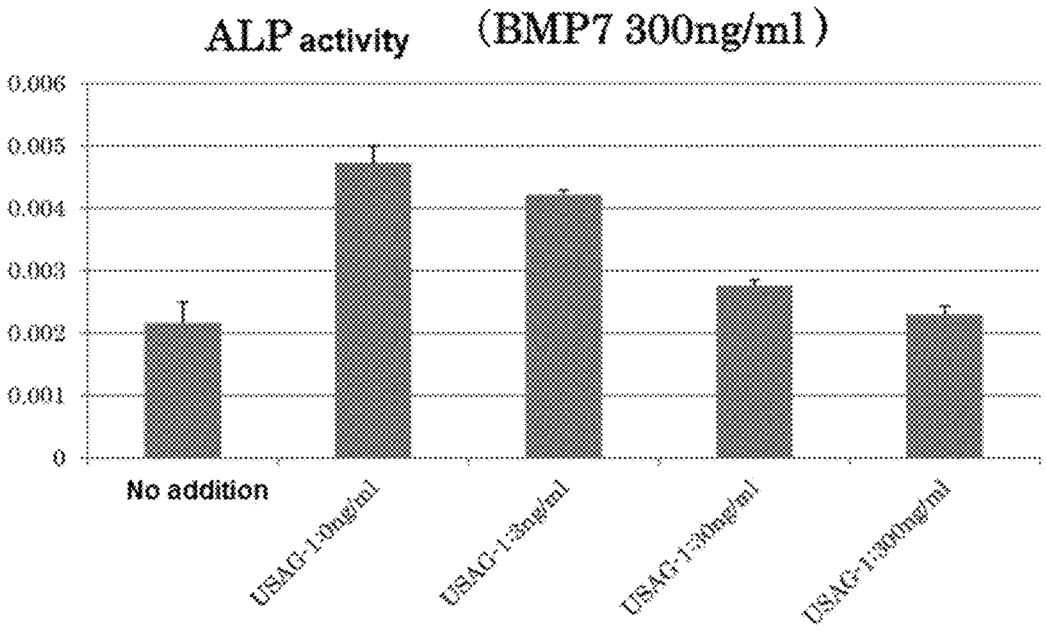

[FIG. 8]
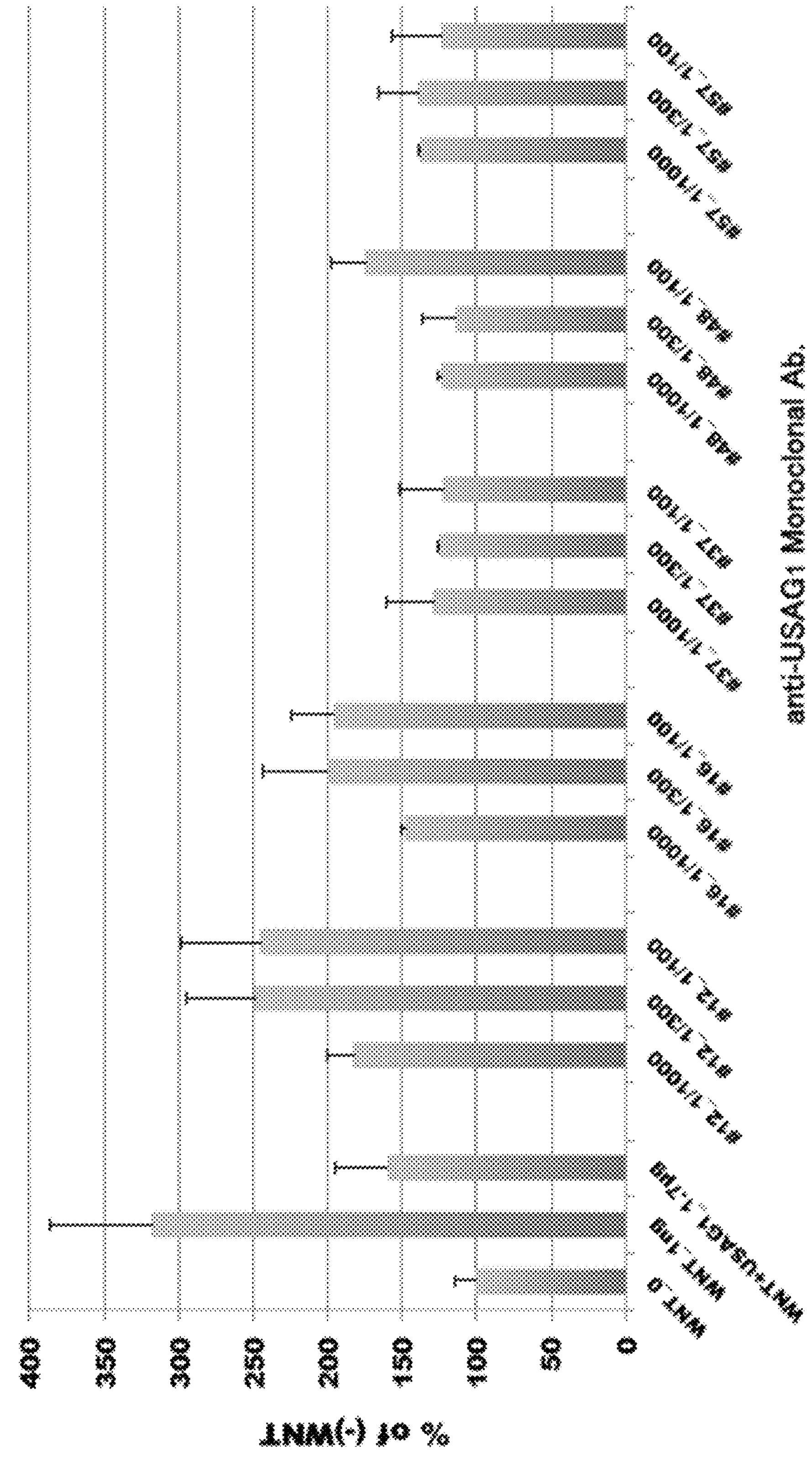

[FIG. 9]
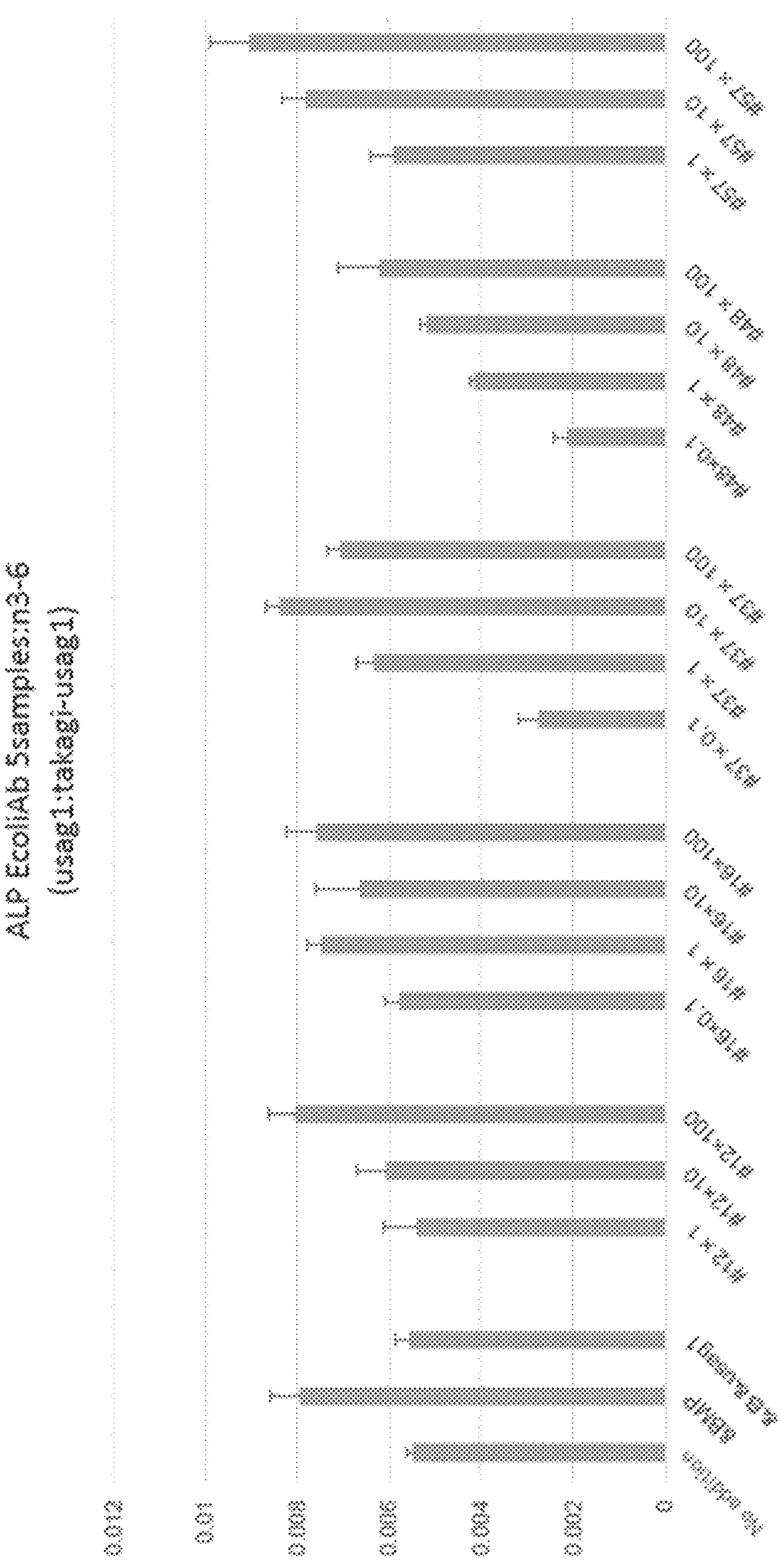

[FIG. 10]
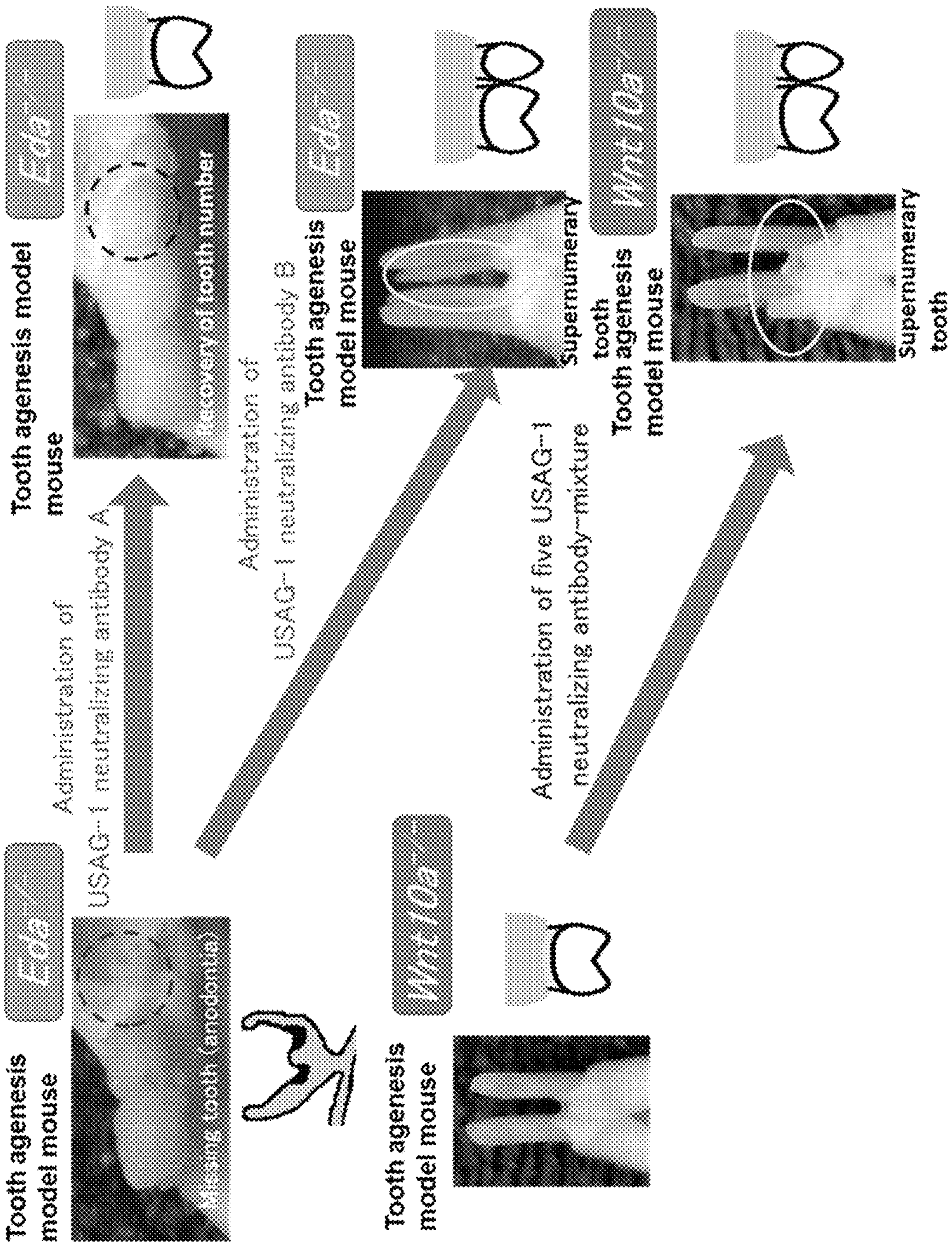

[FIG. 11]
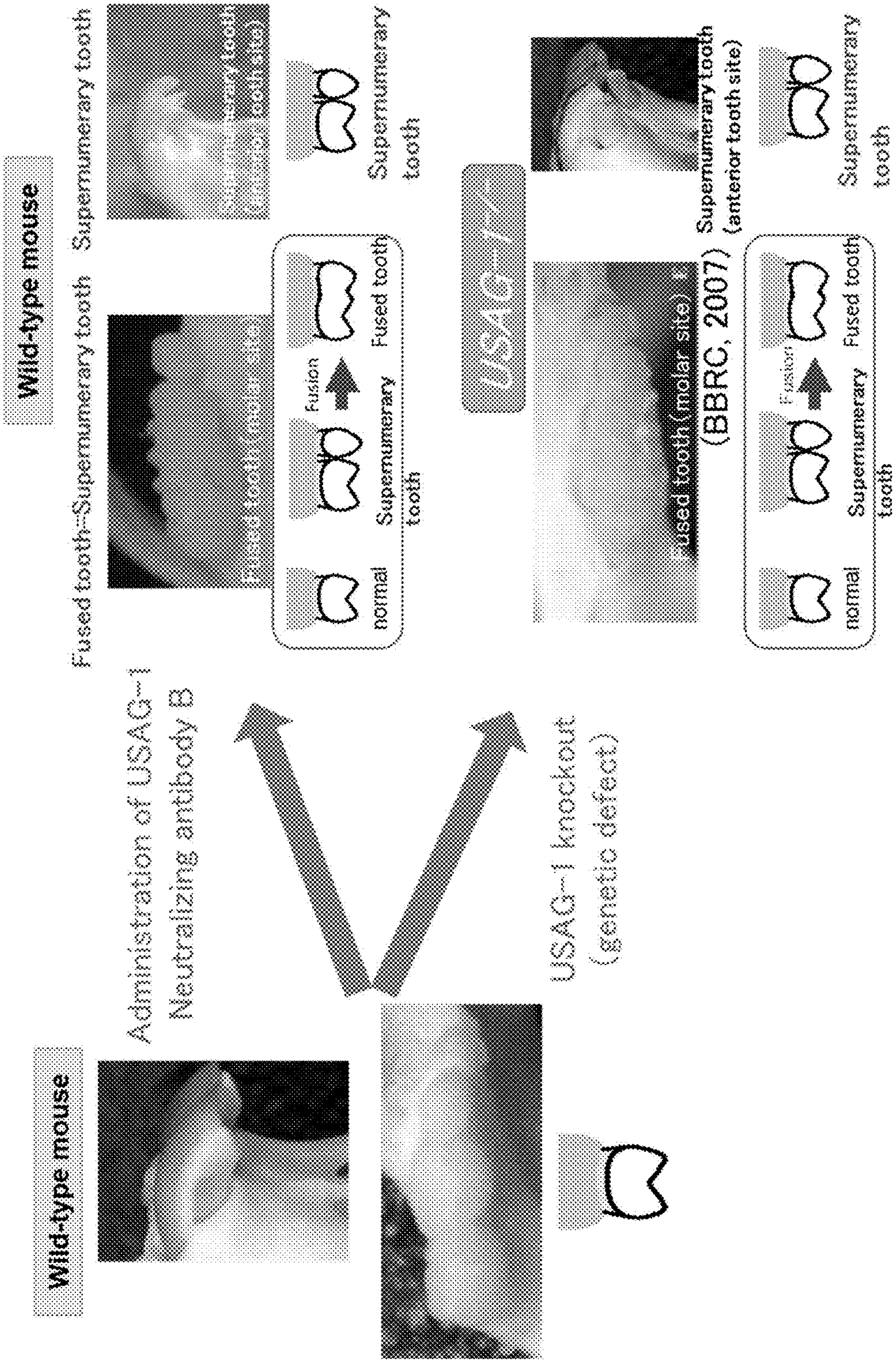

[FIG. 12]
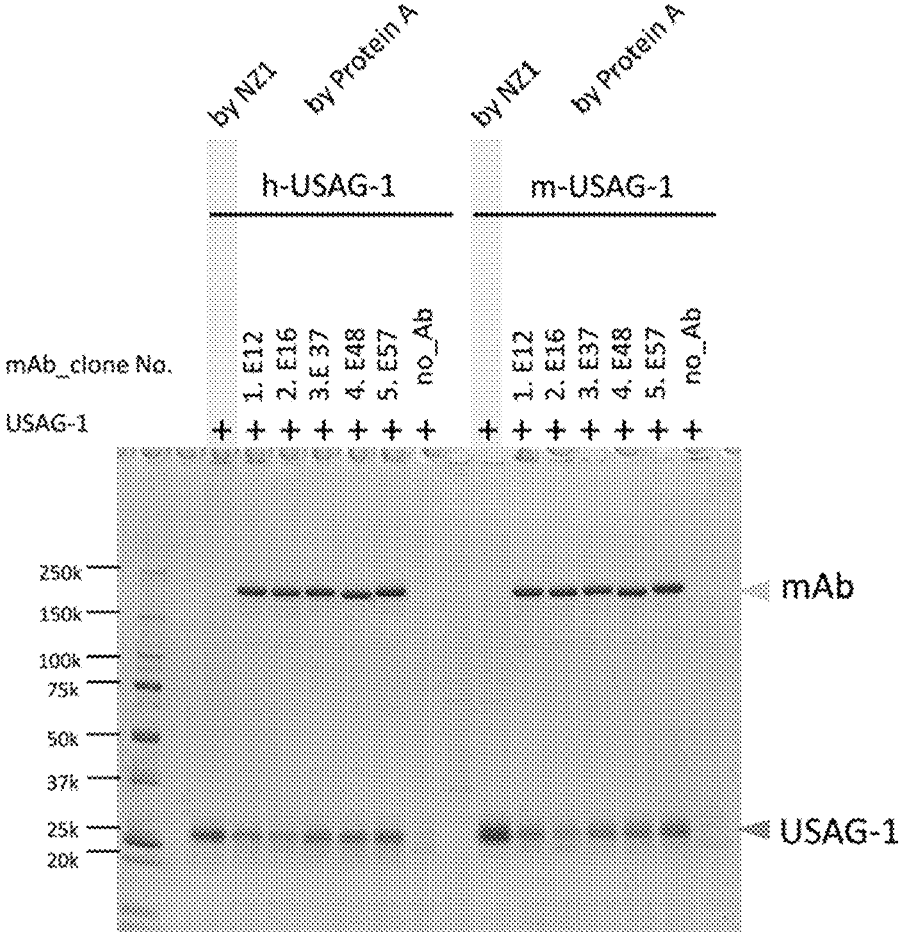

[FIG. 13]
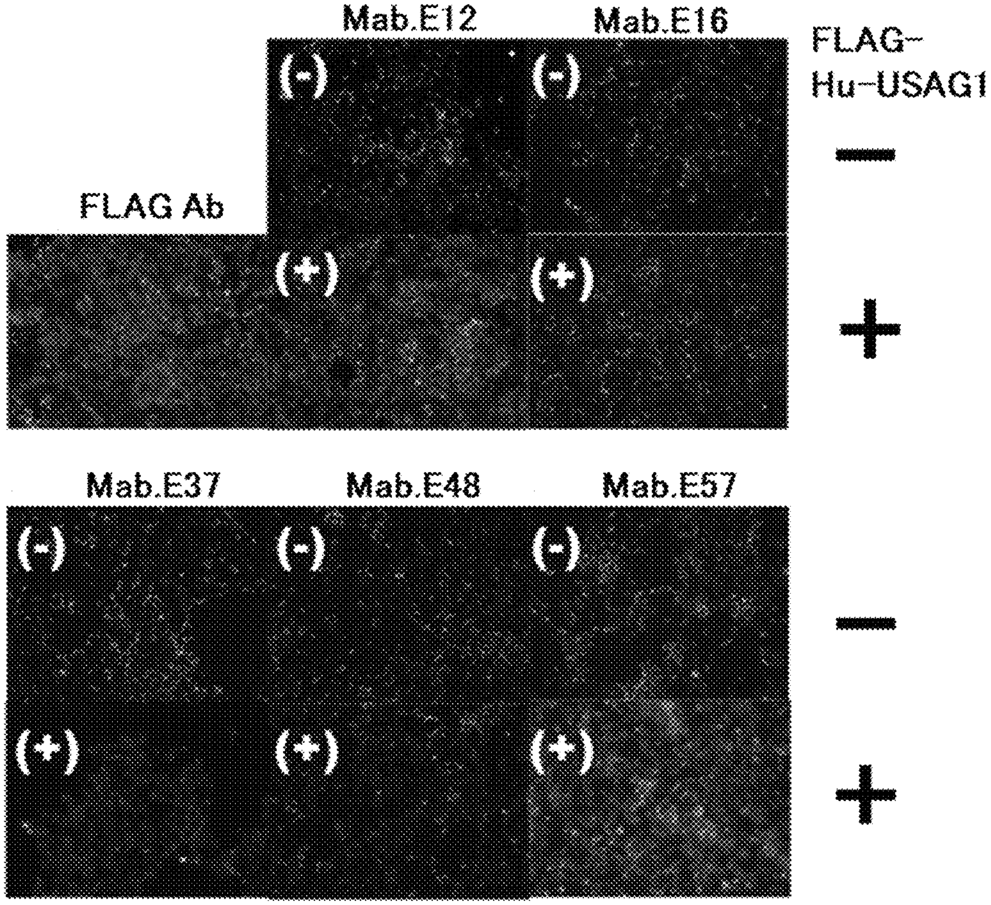

[FIG. 14]

Antibody A

VH (CDR 1,2,3 are underlined, in order from 1 to 3.)
QVQLQQSDAELVNPGASVKISCKVSGYTFTDHTIHWMKQRPEQGLEWIGYIYPGDGSTKY
NEKFKGKATLTADKSSSTAYMQLNSLTSEDSAVYFCARTETYYGRIYYYAMDYWGQGTSV
TVSS VL (CDR 1,2,3 are underlined, in order from 1 to 3.)
QIVLSQSPAILSASPGEKVTMTCRASSSVSYMYWYQQKPGSSPKPWIYATSNLASGVPIRF
SGSGSGTSYSLTISRVEAEDAATYYCQQWSSNLTFGAGTKLELK

Antibody B

VH (CDR 1,2,3 are underlined, in order from 1 to 3.)
EVQLQQSGPELVKPGASVKISCKTSGYSFTGYYMSWVKQSPEKSLEWIGEINPTTGGSTYN
QKFKAKATLTVDKSSSTAYMQLKSLTSEDSAVYYCAREGYYSGISYDAMDYWGQGTSVTV
SS VL (CDR 1,2,3 are underlined, in order from 1 to 3.)
DIQMTQTTSSLSASLGDRVTISCRASQDISNYLSWYQQKPDGTVKLLIYYTSRLHSGVPSRF
SGSGSGTDYSLTISNLEQEDIATYFCQQGNTLPRTFGGGTKLEIK

[FIG. 15]
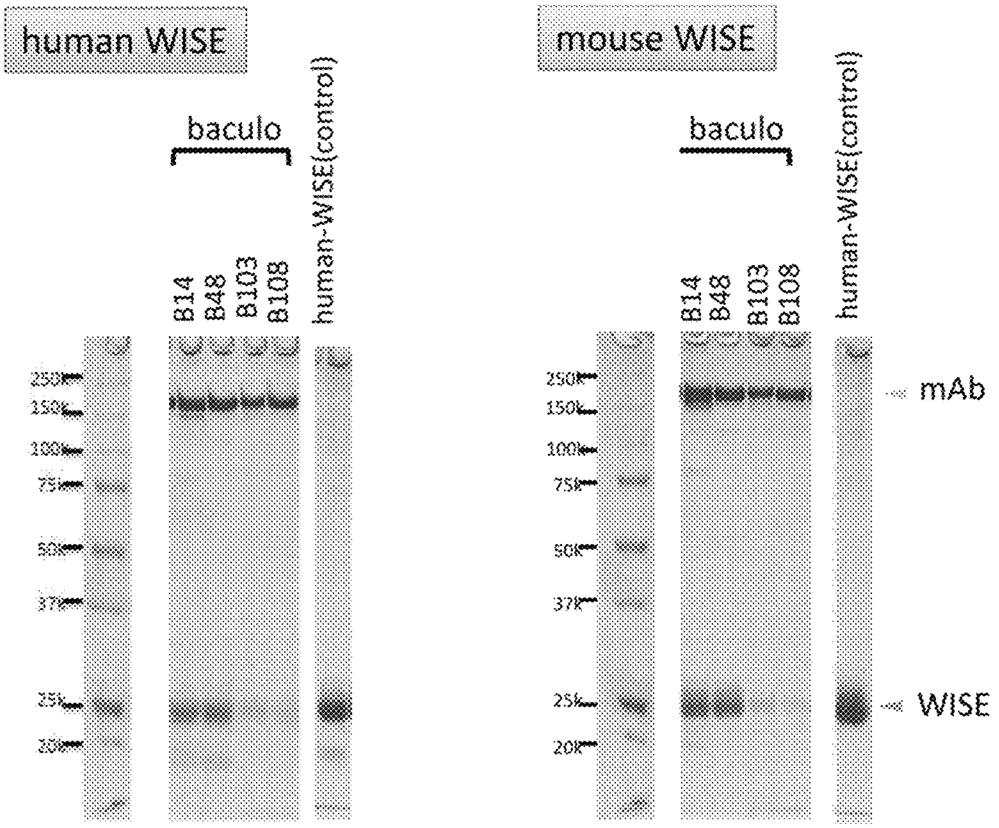

[FIG. 16]
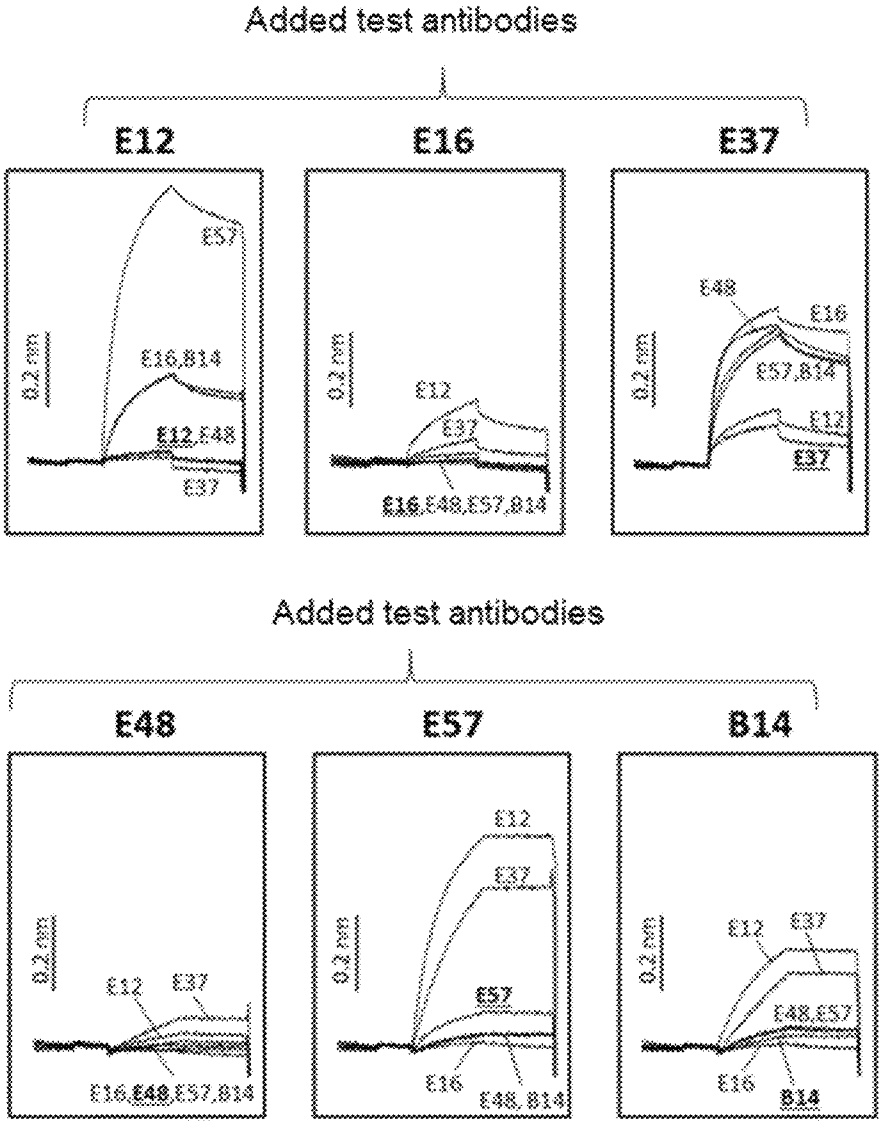

[FIG. 17]
BMP
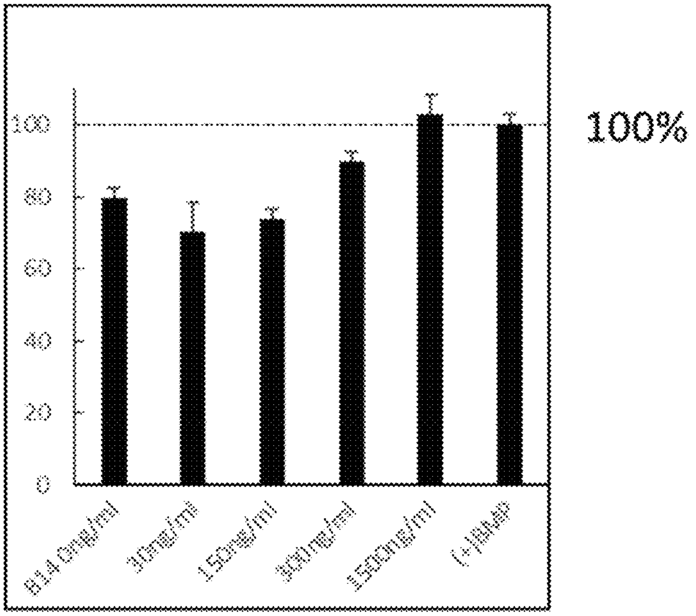
Wnt
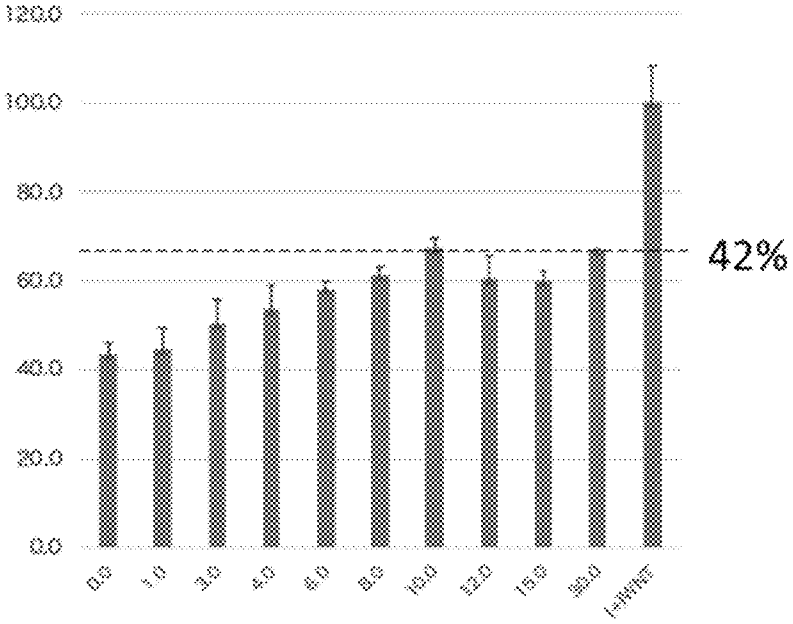

[FIG. 18]
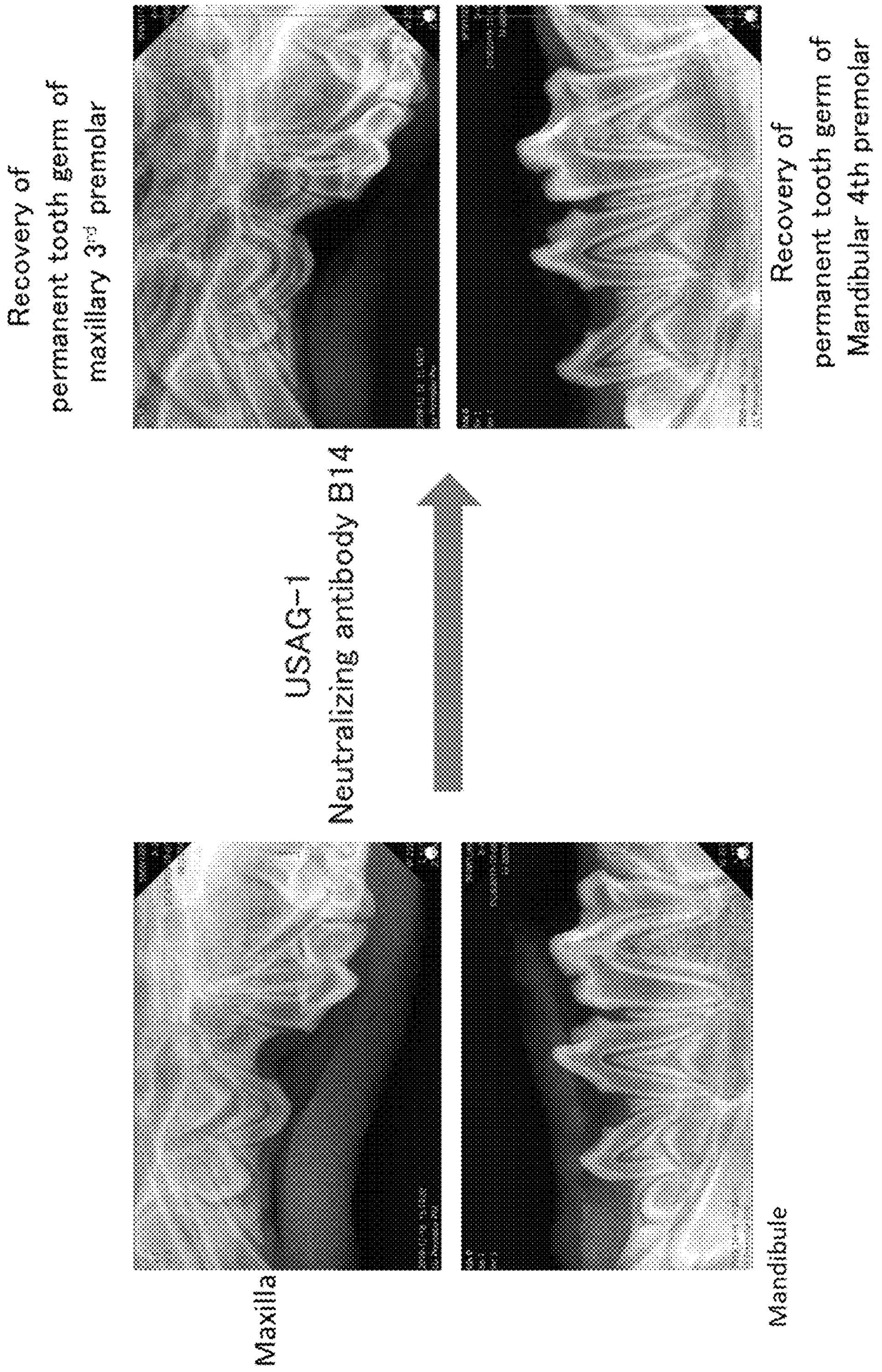

[FIG. 19]
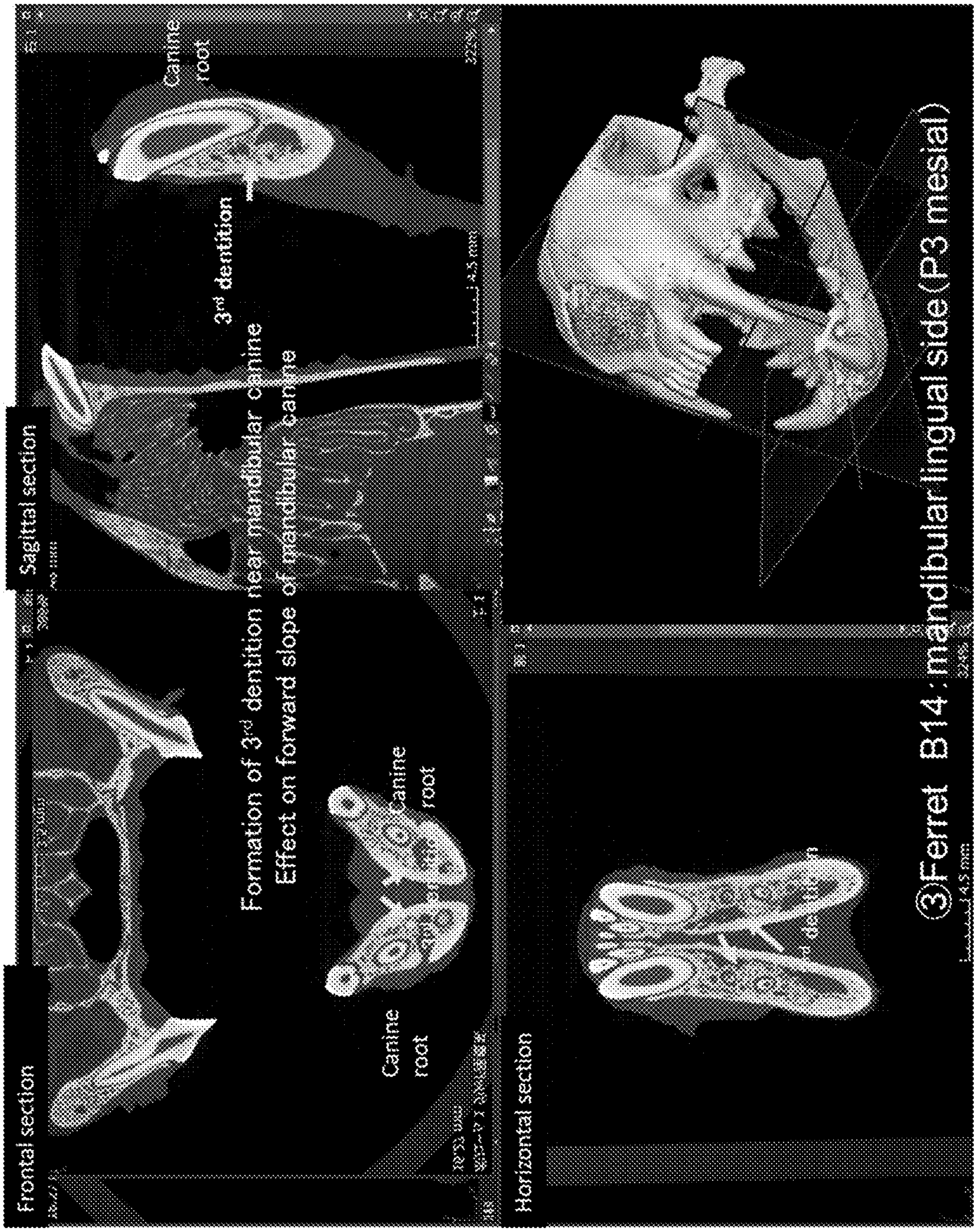

[FIG. 20]

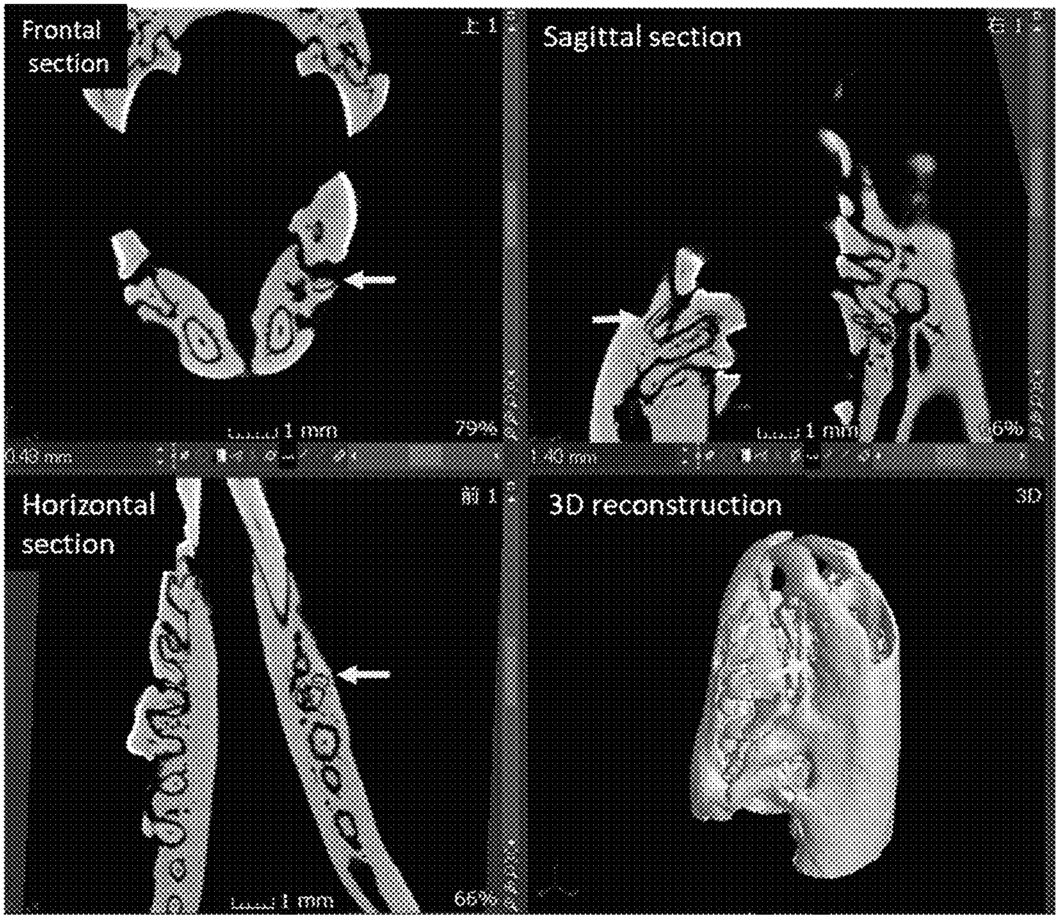

[FIG. 21]

Antibody C

VH (G3) (CDR1,2,3 underilied in order from 1 to 3; Italic: D region; Bold: J region; other: V region)

EVQLQQSGPELVKPGASVKISCKASGYSFTGYYMNWVKQSPEKSLEWIGEIN
PTTGGTTYNQKFKAKATLTVDKSSSTAYMQLKSLTSEDSAVYYCAR*LHYDYDG*
*V*GYAMDYWGQGTSVTVSS

VL (kappa) (CDR1,2,3 underilied in order from 1 to 3; Bold: J region other: V region)

DIVMTQSHKFMSTSVGDRVSITCKASQDVSTAVAWYQQKPGQSPKLLIYSASY
RYTGVPARFTGSGSGTDFTFTISSVQAEDLAVYYCQQHYSTPPTFGGGTKLEI

[FIG. 22]

Antibody D

VH (IgG1) (Underline: CDR1,2,3 in order from 1 to 3; Italic: D region; Bold: J region; Other: V region)

EVQLQQSGAELVRPGASVKLSCTASGFNIKDDYMHWVKQRPEQGLEWIGWIDPENGDTE
YASKFQGKATITADTSSNTAYLQLSSLTSEDTAVYYC*ITPYYYGSSFS*YWYFDVWGTGTTVT
VSS

VL (Igκ) (Underline: CDR1,2,3 in order from 1 to 3; Bold: J region; Other: V region)

DVVMTQTPLTLSVTIGQPASISCKSSQSLLDSDGKTYLNWLLQRPGQSPKRLIYLVSKLDSG
VPDRFTGSGSGTDFTLKISRVEAEDLGVYYCWQGTHFPRTFGGGTKLEIK

Antibody E

VH (IgG1) (Underline: CDR1,2,3 in order from 1 to 3; Italic: D region; Bold: J region; Other: V region)

DVQLQESGPGLVKPSQSLSLTCSVTGYSITSGYYWNWIRQFPGNKLEWMGCISYDGSNN
YNPSLKNRISITRDTSKNQFFLKLNSVTTEDTATYYCAR*GGLL*WGQGTTLTVSS

VL (Igκ) (Underline: CDR1,2,3 in order from 1 to 3; Bold: J region; Other: V region)

DIQMTQSPSSLSASLGERVSLTCRASQEISGYLSWLQQKPDGNIKRLIYAASTLDSGVPKRF
SGSRSGSDYSLTISRLESEDFADYYCLQYASYPWTFGGGTKLEIK

[FIG. 23]

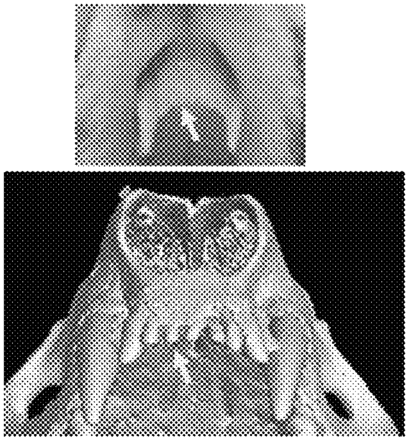

B103: 7 Maxillary anterior teeth

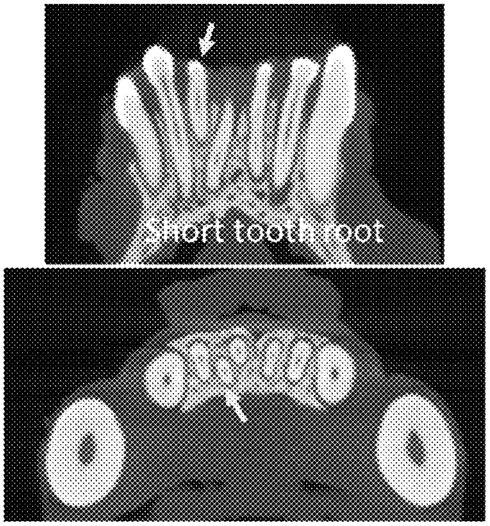

B103:Right upper 2 linguoversion

[FIG. 24]
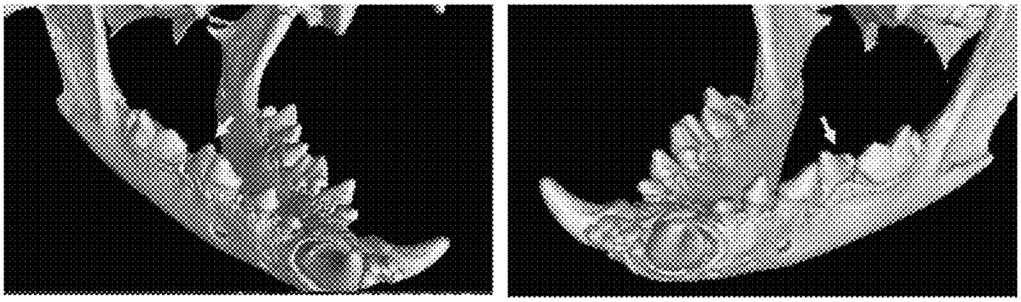
Formation/eruption of 3rd dentition at right lower premolar site
Formation/eruption of 3rd dentition at left lower premolar site
[FIG. 25]
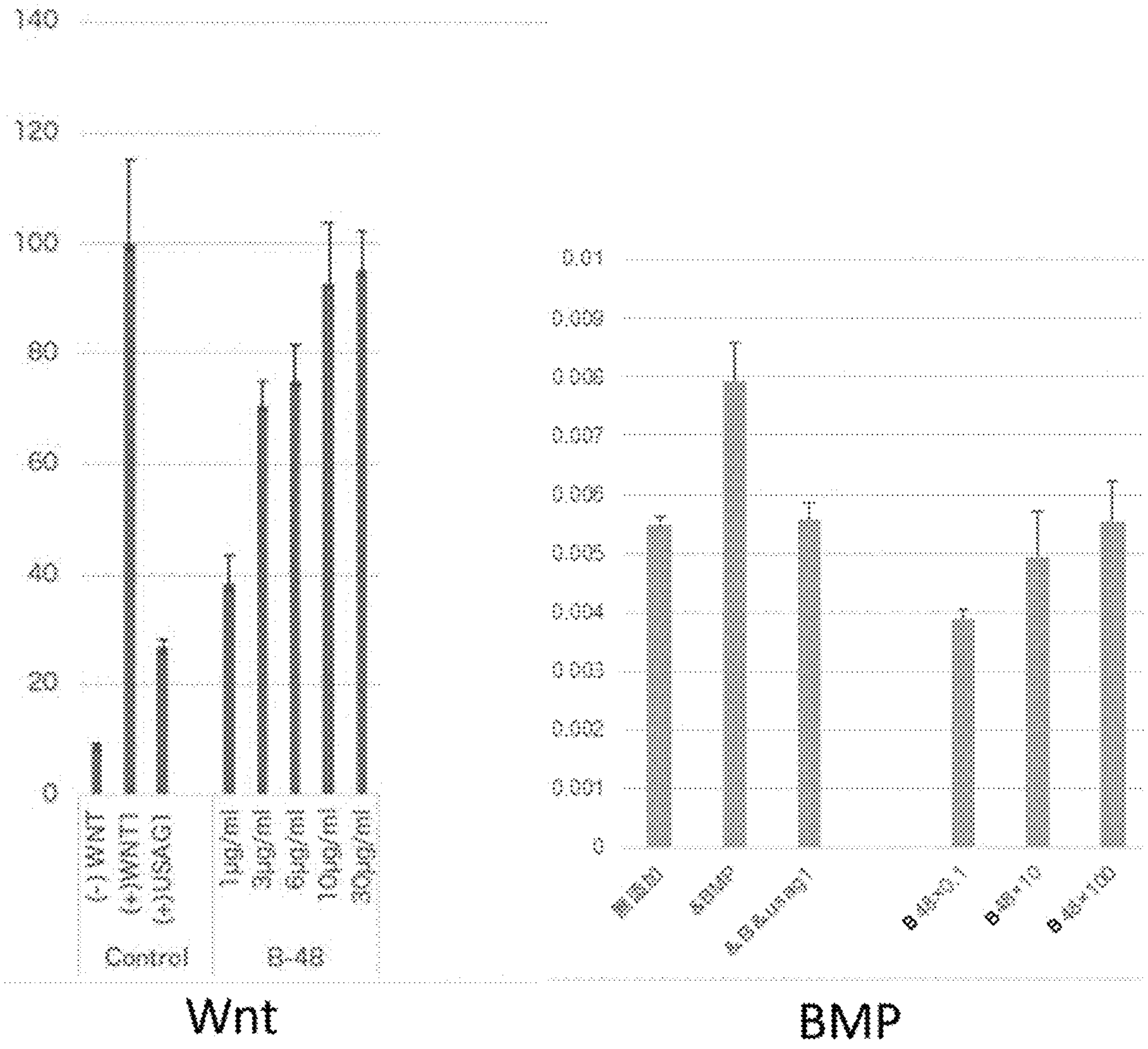

[FIG. 26]
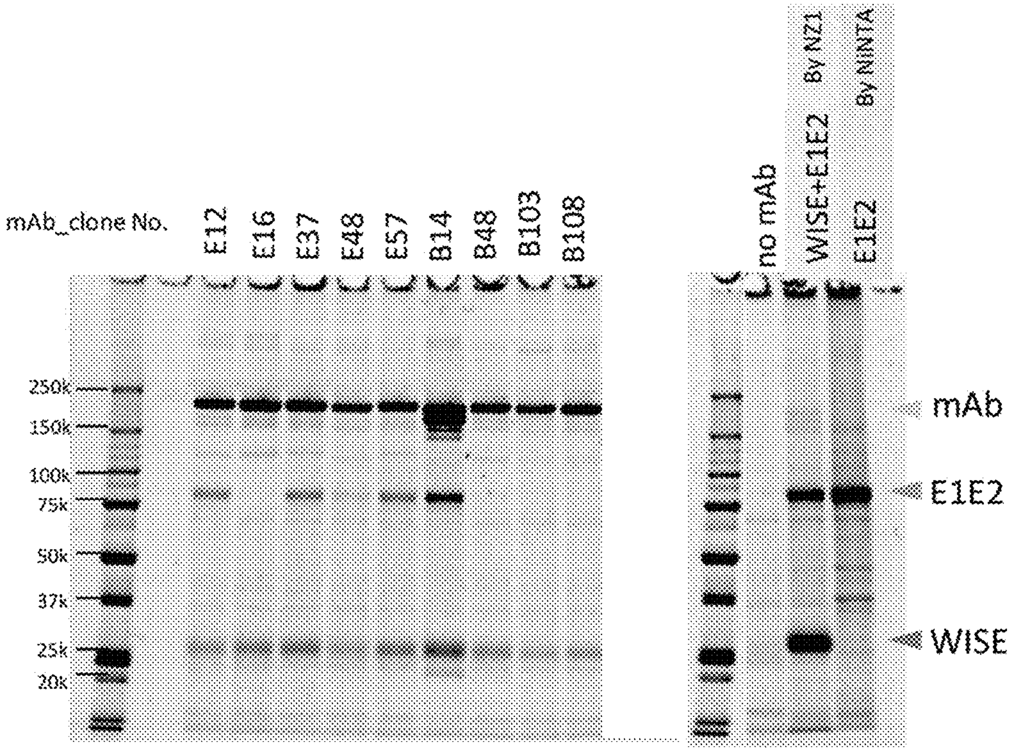

NEUTRALIZING ANTIBODY FOR TOOTH REGENERATION TREATMENT TARGETING USAG-1 MOLECULE

SEQUENCE LISTING SUBMISSION VIA EFS-WEB

A computer readable text file, entitled "SequenceListing.txt," created on Jan. 25, 2022 with a file size of 47,308 bytes contains the sequence listing for this application and is hereby incorporated by reference in its entirety.

TECHNICAL FIELD

The present invention relates to a neutralizing antibody targeting USAG-1 for the treatment of tooth agenesis or tooth regeneration.

BACKGROUND ART

In the majority of patients, acquired diseases such as dental caries and periodontal disease result in tooth agenesis (patients with loss of teeth). As high as 1% incidence rate of congenital tooth agenesis is also reported. Currently, the only treatment method for missing teeth is prosthetic treatment which includes dental implants and dentures, and there is no fundamental treatment method. Numerous studies of tooth regeneration using tissue engineering approaches have been reported. Various cells such as stem cells (Non-Patent Literature 1) are used as cell sources. In addition, in order to allow teeth made in vitro to function in the oral cavity, an "organ primordium method" (Non-Patent Literature 2), a cell manipulation technology for regenerating a dental organ primordium (the rudiment of the organ) in a collagen gel, has been reported. However, owing to cost and safety problems for securing cell sources, tissue engineering approaches have not reached clinical application.

A large number of causative genes for congenital tooth agenesis have been identified, and many of them are common to both human and mouse. For example, RUNX2, MSX1, EDA, WNT10A, PAX9, AXIN2 etc. are known. Among the listed genes, WNT10A gene has been reported to cause congenital tooth agenesis in the largest number of patients. EDA gene is a causative gene for anhidrotic ectodermal dysplasia, which is a representative disease of syndromic congenital tooth agenesis. Congenital tooth agenesis is caused by tooth development stopped prematurely due to defect in the causative gene and suppression of the function of the causative gene.

CITATION LIST

Patent Literature

Patent Literature 1: Ohazama, J Denr Res, 2004
Patent Literature 2: Nakao, Nat Methods, 2007

SUMMARY OF INVENTION

Problem to be Solved by Invention

From a therapeutic viewpoint, the inventors conceived of a novel treatment method to treat congenital tooth agenesis. The new approach promotes differentiation induction from the state of tooth development that has been stopped prematurely to form a complete tooth. Object of the present invention is to provide a technique for treating tooth agenesis which comprises utilizing the differentiation induction inherent in a tooth organ, instead of utilizing surgical tissue transplantation.

Solution for Problem

As a result of diligent research, the present inventors succeeded in developing a neutralizing antibody targeting USAG-1. Furthermore, they found that administration of the antibody regenerated missing teeth in congenital tooth agenesis model mice and formed supernumerary teeth in congenital tooth agenesis model mice or wild-type mice. Thus the present invention was completed.

That is, the present invention relates to:

[1] An antibody or antigen-binding fragment thereof that specifically binds to and neutralizes USAG-1;

[2] The antibody or antigen fragment thereof according to [1], which specifically binds to USAG-1 and neutralizes BMP signaling inhibitory activity of USAG-1;

[3] The antibody or antigen fragment thereof according to [1] or [2], which specifically binds to USAG-1 and neutralizes WNT signaling inhibitory activity of USAG-1;

[4] The antibody or antigen-binding fragment thereof according to any one of [1] to [3], which comprises:

(a) three heavy chain complementarity determining regions that comprise amino acid sequences having at least 90% sequence identity with amino acid sequences set forth in SEQ ID NO: 5, SEQ ID NO: 6 and SEQ ID NO: 7 respectively, or three light chain complementarity determining regions that comprise amino acid sequences having at least 90% sequence identity with amino acid sequences set forth in SEQ ID NO: 8, SEQ ID NO: 9 and SEQ ID NO: 10 respectively;

(b) three heavy chain complementarity determining regions that comprise amino acid sequences having at least 90% sequence identity with amino acid sequences set forth in SEQ ID NO: 15, SEQ ID NO: 16 and SEQ ID NO: 17 respectively, or three light chain complementarity determining regions that comprise amino acid sequences having at least 90% sequence identity with amino acid sequences set forth in SEQ ID NO: 18, SEQ ID NO: 19 and SEQ ID NO: 20 respectively;

(c) three heavy chain complementarity determining regions that comprise amino acid sequences having at least 90% sequence identity with amino acid sequences set forth in SEQ ID NO: 25, SEQ ID NO: 26 and SEQ ID NO: 27 respectively, or three light chain complementarity determining regions that comprise amino acid sequences having at least 90% sequence identity with amino acid sequences set forth in SEQ ID NO: 28, SEQ ID NO: 29 and SEQ ID NO: 30 respectively;

(d) three heavy chain complementarity determining regions that comprise amino acid sequences having at least 90% sequence identity with amino acid sequences set forth in SEQ ID NO: 42, SEQ ID NO: 43 and SEQ ID NO: 44 respectively, or three light chain complementarity determining regions that comprise amino acid sequences having at least 90% sequence identity with amino acid sequences set forth in SEQ ID NO: 45, SEQ ID NO: 46 and SEQ ID NO: 47 respectively; or (e) three heavy chain complementarity determining regions that comprise amino acid sequences having at least 90% sequence identity with amino acid sequences set forth in SEQ ID NO: 52, SEQ ID NO: 53 and SEQ ID NO: 54 respectively, or three light chain complementarity determining regions that comprise amino acid sequences having at least 90% sequence identity with amino acid sequences set forth in SEQ ID NO: 55, SEQ ID NO: 56 and SEQ ID NO: 57 respectively;

[5] The antibody or antigen-binding fragment thereof according to any one of [1] to [4], which comprises:

(f) a heavy chain variable region that comprises an amino acid sequence having at least 90% sequence identity with an amino acid sequence set forth in SEQ ID NO: 3, or a light chain variable region that comprises an amino acid sequence having at least 90% sequence identity with an amino acid sequence set forth in SEQ ID NO: 4;

(g) a heavy chain variable region that comprises an amino acid sequence having at least 90% sequence identity with an amino acid sequence set forth in SEQ ID NO: 13, or a light chain variable region that comprises an amino acid sequence having at least 90% sequence identity with an amino acid sequence set forth in SEQ ID NO: 14;

(h) a heavy chain variable region that comprises an amino acid sequence having at least 90% sequence identity with an amino acid sequence set forth in SEQ ID NO: 23, or a light chain variable region that comprises an amino acid sequence having at least 90% sequence identity with an amino acid sequence set forth in SEQ ID NO: 24;

(i) a heavy chain variable region that comprises an amino acid sequence having at least 90% sequence identity with an amino acid sequence set forth in SEQ ID NO: 40, or a light chain variable region that comprises an amino acid sequence having at least 90% sequence identity with an amino acid sequence set forth in SEQ ID NO: 41; or (j) a heavy chain variable region that comprises an amino acid sequence having at least 90% sequence identity with an amino acid sequence set forth in SEQ ID NO: 50, or a light chain variable region that comprises an amino acid sequence having at least 90% sequence identity with an amino acid sequence set forth in SEQ ID NO: 51;

[6] The antibody or antigen-binding fragment thereof according to any one of [1] to [3], which comprises:

(k) three heavy chain complementarity determining regions that comprise amino acid sequences having at least 90% sequence identity with amino acid sequences set forth in SEQ ID NO: 5, SEQ ID NO: 6 and SEQ ID NO: 7 respectively, and three light chain complementarity determining regions that comprise amino acid sequences having at least 90% sequence identity with amino acid sequences set forth in SEQ ID NO: 8, SEQ ID NO: 9 and SEQ ID NO: 10 respectively;

(l) three heavy chain complementarity determining regions that comprise amino acid sequences having at least 90% sequence identity with amino acid sequences set forth in SEQ ID NO: 15, SEQ ID NO: 16 and SEQ ID NO: 17 respectively, and three light chain complementarity determining regions that comprise amino acid sequences having at least 90% sequence identity with amino acid sequences set forth in SEQ ID NO: 18, SEQ ID NO: 19 and SEQ ID NO: 20 respectively;

(m) three heavy chain complementarity determining regions that comprise amino acid sequences having at least 90% sequence identity with amino acid sequences set forth in SEQ ID NO: 25, SEQ ID NO: 26 and SEQ ID NO: 27 respectively, and three light chain complementarity determining regions that comprise amino acid sequences having at least 90% sequence identity with amino acid sequences set forth in SEQ ID NO: 28, SEQ ID NO: 29 and SEQ ID NO: 30 respectively;

(n) three heavy chain complementarity determining regions that comprise amino acid sequences having at least 90% sequence identity with amino acid sequences set forth in SEQ ID NO: 42, SEQ ID NO: 43 and SEQ ID NO: 44 respectively, and three light chain complementarity determining regions that comprise amino acid sequences having at least 90% sequence identity with amino acid sequences set forth in SEQ ID NO: 45, SEQ ID NO: 46 and SEQ ID NO: 47 respectively; or (o) three heavy chain complementarity determining regions that comprise amino acid sequences having at least 90% sequence identity with amino acid sequences set forth in SEQ ID NO: 52, SEQ ID NO: 53 and SEQ ID NO: 54 respectively, and three light chain complementarity determining regions that comprise amino acid sequences having at least 90% sequence identity with amino acid sequences set forth in SEQ ID NO: 55, SEQ ID NO: 56 and SEQ ID NO: 57 respectively;

[7] The antibody or antigen-binding fragment thereof according to any one of [1] to [3] and [6], which comprises:

(p) a heavy chain variable region that comprises an amino acid sequence having at least 90% sequence identity with an amino acid sequence set forth in SEQ ID NO: 3, and a light chain variable region that comprises an amino acid sequence having at least 90% sequence identity with an amino acid sequence set forth in SEQ ID NO: 4;

(q) a heavy chain variable region that comprises an amino acid sequence having at least 90% sequence identity with an amino acid sequence set forth in SEQ ID NO: 13, and a light chain variable region that comprises an amino acid sequence having at least 90% sequence identity with an amino acid sequence set forth in SEQ ID NO: 14;

(r) a heavy chain variable region that comprises an amino acid sequence having at least 90% sequence identity with an amino acid sequence set forth in SEQ ID NO: 23, and a light chain variable region that comprises an amino acid sequence having at least 90% sequence identity with an amino acid sequence set forth in SEQ ID NO: 24;

(s) a heavy chain variable region that comprises an amino acid sequence having at least 90% sequence identity with an amino acid sequence set forth in SEQ ID NO: 40, and a light chain variable region that comprises an amino acid sequence having at least 90% sequence identity with an amino acid sequence set forth in SEQ ID NO: 41; or (t) a heavy chain variable region that comprises an amino acid sequence having at least 90% sequence identity with an amino acid sequence set forth in SEQ ID NO: 50, and a light chain variable region that comprises an amino acid sequence having at least 90% sequence identity with an amino acid sequence set forth in SEQ ID NO: 51;

[8] An antibody or antigen-binding fragment thereof that competes with the antibody or antigen-binding fragment thereof according to any one of [4] to [7] for binding to USAG-1;

[9] The antibody or antigen-binding fragment thereof according to any one of [1] to [8], wherein the antibody is a humanized antibody or a chimeric antibody; and

[10] A pharmaceutical composition for dental regenerative therapy, which comprises the antibody or antigen-binding fragment thereof according to any one of [1] to [9].

Effects of the Invention

In the present invention, we succeeded in regenerating teeth in vivo by using an antibody preparation. Treatment with the antibody preparation of the present invention can be clinically applied as a tooth regenerative therapy in a general dental and oral surgical approach such as conventional tooth extraction, orthodontics, and tooth transplantation.

BRIEF DESCRIPTION OF DRAWINGS

FIG. 1 shows the Wnt inhibitory activity of a recombinant human UASG-1 protein derived from *Escherichia coli* which was used as an antigen in Examples.

FIG. 2 shows the BMP inhibitory activity of a recombinant human UASG-1 protein derived from *Escherichia coli* which was used as an antigen in Examples.

FIG. 3 shows USAG-1KO mice newly established using CRISPR-CAS9.

FIG. 4-1 shows results of primary screening for anti-USAG-1 neutralizing antibodies.

FIG. 4-2 shows results of primary screening for anti-USAG-1 neutralizing antibodies.

FIG. 5 shows results of purification and concentration of mouse USAG-1 (WISE) with a PA tag at the N-terminal.

FIG. 6 shows dose-dependent WNT signaling inhibitory activity of mouse USAG-1 protein.

FIG. 7 shows dose-dependent BMP signaling inhibitory activity of mouse USAG-1 protein.

FIG. 8 shows antibodies neutralizing the WNT signaling inhibitory activity of mouse USAG-1 in a dose-dependent manner.

FIG. 9 shows antibodies neutralizing the BMP signaling inhibitory activity of mouse USAG-1 in a dose-dependent manner.

FIG. 10 shows that anti-USAG-1 neutralizing antibodies grow teeth in tooth agenesis model mice.

FIG. 11 shows that the anti-USAG-1 neutralizing antibody has the same effect as USAG-1KO.

FIG. 12 shows experimental results of binding of mouse anti-USAG-1 antibodies to mouse/human USAG-1 proteins.

FIG. 13 shows immunostaining with mouse anti-USAG-1 antibodies in HEK293 cells transiently forcibly expressing human FLAG-tagged USAG-1.

FIG. 14 shows sequences of heavy chain and light chain variable regions of antibody A and antibody B.

FIG. 15 shows experimental results of binding of mouse anti-USAG-1 antibodies to mouse/human USAG-1 proteins.

FIG. 16 shows competitive binding data of the obtained 6 antibodies. In the figure, sensorgrams obtained when each of the 6 test antibodies was reacted with sensors of USAG-1 captured by the 6 antibodies are superposed.

FIG. 17 shows the neutralizing activity of the antibody of the present invention on the WNT signaling inhibitory activity and the BMP signaling inhibitory activity of mouse USAG-1.

FIG. 18 provides dental X-ray radiographs showing the effect of administration of the USAG-1 neutralizing antibody on dogs with congenital tooth agenesis.

FIG. 19 provides μCT images and 3D reconstructed images showing the induction of the 3rd dentition at the sites of mandibular 3rd premolars by administration of the USAG-1 neutralizing antibody in ferrets.

FIG. 20 provides μCT images and 3D reconstructed images showing the induction of the 3rd dentition at the sites of mandibular 3rd premolars by administration of the USAG-1 neutralizing antibody in Suncus.

FIG. 21 shows sequences of heavy chain and light chain variable regions of antibody C.

FIG. 22 shows sequences of heavy chain and light chain variable regions of antibody D and antibody E.

FIG. 23 provides μCT sliced images and 3D reconstructed images showing the induction of the 3rd dentition at the site of a maxillary anterior tooth by administration of the USAG-1 neutralizing antibody in ferrets.

FIG. 24 provides 3D reconstructed images that was created based on μCT data, showing the induction of the 3rd dentition at the site of a mandibular premolar by administration of the USAG-1 neutralizing antibody in ferrets.

FIG. 25 shows the neutralizing activity of the antibody of the present invention on the WNT signaling inhibitory activity and the BMP signaling inhibitory activity of mouse USAG-1.

FIG. 26 shows results of pull-down assay, showing the interaction between a complex of the mouse anti-USAG-1 antibody with mouse USAG-1 protein and an LRP6-E1E2 domain.

MODE FOR CARRYING OUT THE INVENTION

USAG-1 (Uterine Sensitization Associated Gene-1) is a bone morphogenetic protein (BMP) antagonist and a Wnt antagonist, and is also called Sostdc-1, Ectodin, or Wise. It is known that in USAG-1 deficient model mice, an increase in BMP signaling is observed, leading to the formation of supernumerary teeth. The present inventors crossed a Runx2-deficient mouse, which is a model mouse for congenital tooth agenesis, with a USAG-1 gene-deficient mouse, which is a model mouse for supernumerary teeth (teeth exceeding the normal number of teeth), to produce a double-knockout mouse. As a result of analysis of the double-knockout mouse, it was found that tooth formation was recovered. Thus it was suggested that inhibition of USAG-1 could treat tooth agenesis.

This time, the present inventors crossed congenital tooth agenesis model mice lacking causative genes Msx1, Eda and Wnt10a other than Runx2 with an USAG-1 gene-deficient mouse that was newly created by CRISPER-CAS9 system as a model mouse for supernumerary teeth, to produce double-knockout mice. As a result of analysis of the double-knockout mice, it was found that tooth formation was recovered in all the tooth agenesis model mice. Thus it was shown that the treatment by inhibition of USAG-1 can be applied to patients with congenital tooth agenesis caused by various gene mutations.

Then, in the present invention, a human USAG-1 recombinant protein whose activity was confirmed was used as an antigen to produce antibodies. Thus antibodies that specifically bind to USAG-1 were obtained. These antibodies were found to increase BMP signaling and/or Wnt signaling.

Therefore, an aspect of the present invention provides an antibody or an antigen-binding fragment thereof that specifically binds to and neutralizes USAG-1, that is, an anti-USAG-1 neutralizing antibody and an antigen-binding fragment thereof. As used herein unless otherwise specified, USAG-1 means mammalian USAG-1. Examples of the mammal include, but not limited to, a human, a dog, a cat, a horse, a mouse, a ferret, a suncus, a pig, and a monkey, and a human is preferable.

As used herein, neutralizing refers to inhibiting the function of USAG-1. The functions of USAG-1 include, for example, BMP signaling inhibitory activity (also referred to as "BMP antagonist activity") and Wnt signaling inhibitory activity (also referred to as "Wnt antagonist activity"). The antibody or antigen-binding fragment thereof of the present disclosure inhibits the BMP signaling inhibitory activity and/or the Wnt signaling inhibitory activity of USAG-1. Therefore, the antibody or antigen-binding fragment thereof of the present disclosure neutralizes either or both of the BMP signaling inhibitory activity of USAG-1 and the Wnt signaling inhibitory activity of USAG-1. For example, the antibody or antigen-binding fragment thereof of the present disclosure includes, but not limited to, an antibody or an antigen-binding fragment thereof that specifically binds to USAG-1 and neutralizes the BMP signaling inhibitory activity of USAG-1 and does not neutralize the Wnt signaling inhibitory activity of USAG-1, and an antibody or an antigen-binding fragment thereof that specifically binds to USAG-1 to neutralize the Wnt signaling inhibitory activity of USAG-1 and does not neutralize the BMP signaling inhibitory activity of USAG-1. As used herein, "inhibition" includes suppression and reduction.

The neutralizing activity of an antibody or an antigen-binding fragment may be determined by a conventional method. The activity of neutralizing the BMP antagonist activity of USAG-1 (also referred to as "BMP antagonist neutralizing activity") can be measured in vitro by, for example, an ALP (alkaline phosphatase) assay or a reporter assay. In the ALP assay, for example, osteoblast progenitor cells and the like are cultured in the presence of BMP with addition of USAG-1 protein and an antibody or an antigen-binding fragment thereof, and ALP generated when differentiation into osteoblasts is induced is measured. The activity of neutralizing the Wnt antagonist activity of USAG-1 (also referred to as "Wnt antagonist neutralizing activity") can be determined in vitro, for example, by a reporter assay. In the reporter assay, for example, a vector containing a promoter region that reacts with BMP or Wnt, ligated to a reporter gene such as luciferase is introduced into a cell, the cell is cultured in the presence of BMP or Wnt with addition of USAG-1 protein and an antibody or an antigen-binding fragment thereof, and expressed luciferase activity is measured. The BMP antagonist activity to be neutralized by the anti-USAG-1 antibody or antigen-binding fragment thereof of the present disclosure may be an antagonist activity against any BMP family. For example, the anti-USAG-1 antibody or antigen-binding fragment thereof of the present disclosure may neutralize the antagonist activity against BMP2, BMP4, BMP6, BMP7, etc. The Wnt antagonist activity to be neutralized by the anti-USAG-1 antibody or antigen-binding fragment thereof of the present disclosure may be an antagonist activity against any Wnt family. For example, the anti-USAG-1 antibody or antigen-binding fragment thereof of the present disclosure may neutralize the antagonist activity against Wnt-1, Wnt-3, etc.

Furthermore, in the present invention, five of the obtained antibodies, namely antibody A, antibody B, antibody C, antibody D and antibody E were sequenced and analyzed. Then, the variable regions and complementarity determining regions of each antibody were determined. Antibody A comprises a heavy chain comprising an amino acid sequence set forth in SEQ ID NO: 1 and a light chain comprising an amino acid sequence set forth in SEQ ID NO: 2, and the heavy chain comprises a heavy chain variable region (SEQ ID NO: 3) comprising heavy chain complementarity determining regions comprising amino acid sequences set forth in SEQ ID NO: 5, SEQ ID NO: 6 and SEQ ID NO: 7, and the light chain comprises a light chain variable regions (SEQ ID NO: 4) comprising light chain complementarity determining regions set forth in SEQ ID NO: 8, SEQ ID NO: 9 and SEQ ID NO: 10. The antibody B comprises a heavy chain comprising an amino acid sequence set forth in SEQ ID NO: 11 and a light chain comprising an amino acid sequence set forth in SEQ ID NO: 12, and the heavy chain comprises a heavy chain variable region (SEQ ID NO: 13) comprising heavy chain complementarity determining regions set forth in SEQ ID NO: 15, SEQ ID NO: 16 and SEQ ID NO: 17, and the light chain comprises a light chain variable regions (SEQ ID NO: 14) comprising light chain complementarity determining regions set forth in SEQ ID NO: 18, SEQ ID NO: 19 and SEQ ID NO: 20. The antibody C comprises a heavy chain comprising an amino acid sequence set forth in SEQ ID NO: 21 and a light chain comprising an amino acid sequence set forth in SEQ ID NO: 22, and the heavy chain comprises a heavy chain variable region (SEQ ID NO: 23) comprising heavy chain complementarity determining regions set forth in SEQ ID NO: 25, SEQ ID NO: 26 and SEQ ID NO: 27, and the light chain comprises a light chain variable regions (SEQ ID NO: 24) comprising light chain complementarity determining regions set forth in SEQ ID NO: 28, SEQ ID NO: 29 and SEQ ID NO: 30. The antibody D comprises a heavy chain comprising an amino acid sequence set forth in SEQ ID NO: 38 and a light chain comprising an amino acid sequence set forth in SEQ ID NO: 39, and the heavy chain comprises a heavy chain variable region (SEQ ID NO: 40) comprising heavy chain complementarity determining regions set forth in SEQ ID NO: 42, SEQ ID NO: 43 and SEQ ID NO: 44, and the light chain comprises a light chain variable regions (SEQ ID NO: 41) comprising light chain complementarity determining regions set forth in SEQ ID NO: 45, SEQ ID NO: 46 and SEQ ID NO: 47. The antibody E comprises a heavy chain comprising an amino acid sequence set forth in SEQ ID NO: 48 and a light chain comprising an amino acid sequence set forth in SEQ ID NO: 49, and the heavy chain comprises a heavy chain variable region (SEQ ID NO: 50) comprising heavy chain complementarity determining regions set forth in SEQ ID NO: 52, SEQ ID NO: 53 and SEQ ID NO: 54, and the light chain comprises a light chain variable regions (SEQ ID NO: 51) comprising light chain complementarity determining regions set forth in SEQ ID NO: 55, SEQ ID NO: 56 and SEQ ID NO: 57. The antibody A, antibody B and antibody C particularly have BMP antagonist neutralizing activity. The antibody C particularly has both BMP antagonist neutralizing activity and Wnt antagonist neutralizing activity. The antibody D and antibody E particularly have Wnt antagonist neutralizing activity.

Therefore, in an aspect of the present invention, antibody A, antibody B, antibody C, antibody D, and antibody E and their mutants are provided as the antibody or antigen-binding fragment thereof of the present disclosure. An example of antibody A or a mutant thereof includes an antibody or an antigen-binding fragment thereof that specifically binds to and neutralizes USAG-1 and comprises three heavy chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 5, SEQ ID NO: 6 and SEQ ID NO: 7 respectively, or three light chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 8, SEQ ID NO: 9 and SEQ ID NO: 10 respectively. Preferably provided is an antibody or an antigen-binding fragment thereof that specifically binds to and neutralizes USAG-1 and comprises three heavy chain complementarity determining regions comprising amino acid sequences set forth in SEQ ID NO: 5, SEQ ID NO: 6 and SEQ ID NO: 7 respectively, or three light chain complementarity determining regions comprising amino acid sequences set forth in SEQ ID NO: 8, SEQ ID NO: 9 and SEQ ID NO: 10 respectively. More preferably provided is an antibody or an antigen-binding fragment thereof that specifically binds to and neutralizes USAG-1 and comprises three heavy chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 5, SEQ ID NO: 6 and SEQ ID NO: 7 respectively, or three light chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 8, SEQ ID NO: 9 and SEQ ID NO: 10 respectively. Still more preferably provides is an antibody or an antigen-binding fragment thereof that specifically binds to and neutralizes USAG-1 and comprises three heavy chain complementarity determining regions consisting of amino acid sequences set forth in SEQ ID NO: 5, SEQ ID NO: 6 and SEQ ID NO: 7 respectively, or three light chain complementarity determining regions consisting of amino acid sequences set forth in SEQ ID NO: 8, SEQ ID NO: 9 and SEQ ID NO: 10 respectively.

A further example of antibody A or a mutant thereof includes an antibody or an antigen-binding fragment thereof that specifically binds to and neutralizes USAG-1, comprises three heavy chain complementarity determining regions comprising amino acid sequences set forth in SEQ ID NO: 5, SEQ ID NO: 6 and SEQ ID NO: 7 respectively, or three light chain complementarity determining regions comprising amino acid sequences set forth in SEQ ID NO: 8, SEQ ID NO: 9 and SEQ ID NO: 10 respectively, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises three heavy chain complementarity determining regions consisting of amino acid sequences set forth in SEQ ID NO: 5, SEQ ID NO: 6 and SEQ ID NO: 7 respectively, or three light chain complementarity determining regions consisting of amino acid sequences set forth in SEQ ID NO: 8, SEQ ID NO: 9 and SEQ ID NO: 10 respectively, and comprises substitution, deletion, insertion or addition of one to several amino acid residues in at least one of the above-mentioned amino acid sequences.

A further example of antibody A or a mutant includes an antibody or an antigen-binding fragment thereof that specifically binds to and neutralizes USAG-1 and comprises a heavy chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 3 or a light chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 4. Preferably provided is an antibody or an antigen-binding fragment thereof that specifically binds to and neutralizes USAG-1 and comprises a heavy chain variable region comprising an amino acid sequence set forth in SEQ ID NO: 3 or a light chain variable region comprising an amino acid sequence set forth in SEQ ID NO: 4. More preferably provided is an antibody or an antigen-binding fragment thereof that specifically binds to and neutralizes USAG-1 and comprises a heavy chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 3 or a light chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 4. Still more preferably provided is an antibody or an antigen-binding fragment thereof that specifically binds to and neutralizes USAG-1 and comprises a heavy chain variable region consisting of an amino acid sequence set forth in SEQ ID NO: 3 or a light chain variable region consisting of an amino acid sequence set forth in SEQ ID NO: 4.

A further example of antibody A or a mutant thereof includes an antibody or an antigen-binding fragment thereof that specifically binds to and neutralizes USAG-1, comprises a heavy chain variable region comprising an amino acid sequence set forth in SEQ ID NO: 3 or a light chain variable region comprising an amino acid sequence set forth in SEQ ID NO: 4, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises a heavy chain variable region consisting of an amino acid sequence set forth in SEQ ID NO: 3 or a light chain variable region consisting of an amino acid sequence set forth in SEQ ID NO: 4, and comprises substitution, deletion, insertion or addition of one to several amino acid residues in at least one of the above-mentioned amino acid sequences.

A further example of antibody A or a mutant thereof includes an antibody or an antigen-binding fragment thereof that specifically binds to and neutralizes USAG-1, and comprises three heavy chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 5, SEQ ID NO: 6 and SEQ ID NO: 7 respectively and three light chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 8, SEQ ID NO: 9 and SEQ ID NO: 10 respectively. Preferably provided is an antibody or an antigen-binding fragment thereof that specifically binds to and neutralizes USAG-1, and comprises three heavy chain complementarity determining regions comprising amino acid sequences set forth in SEQ ID NO: 5, SEQ ID NO: 6 and SEQ ID NO: 7 respectively and three light chain complementarity determining regions comprising amino acid sequences set forth in SEQ ID NO: 8, SEQ ID NO: 9 and SEQ ID NO: 10 respectively. More preferably provided is an antibody or an antigen-binding fragment thereof that specifically binds to and neutralizes USAG-1, and comprises three heavy chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 5, SEQ ID NO: 6 and SEQ ID NO: 7 respectively and three light chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 8, SEQ ID NO: 9 and SEQ ID NO: 10 respectively. Still more preferably provides is an antibody or an antigen-binding fragment thereof that specifically binds to and neutralizes USAG-1, and comprises three heavy chain complementarity determining regions consisting of amino acid sequences set forth in SEQ ID NO: 5, SEQ ID NO: 6 and SEQ ID NO: 7 respectively and three light chain complementarity determining regions consisting of amino acid sequences set forth in SEQ ID NO: 8, SEQ ID NO: 9 and SEQ ID NO: 10 respectively.

A further example of antibody A or a mutant thereof includes an antibody or an antigen-binding fragment thereof that specifically binds to and neutralizes USAG-1, comprises three heavy chain complementarity determining regions comprising amino acid sequences set forth in SEQ ID NO: 5, SEQ ID NO: 6 and SEQ ID NO: 7 respectively and three light chain complementarity determining regions comprising amino acid sequences set forth in SEQ ID NO: 8, SEQ ID NO: 9 and SEQ ID NO: 10 respectively, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises three heavy chain complementarity determining regions consisting of amino acid sequences set forth in SEQ ID NO: 5, SEQ ID NO: 6 and SEQ ID NO: 7 respectively and three light chain complementarity determining regions consisting of amino acid sequences set forth in SEQ ID NO: 8, SEQ ID NO: 9 and SEQ ID NO: 10 respectively, and comprises substitution, deletion, insertion or addition of one to several amino acid residues in at least one of the above-mentioned amino acid sequences.

A further example of antibody A or a mutant thereof includes an antibody or an antigen-binding fragment thereof that specifically binds to and neutralizes USAG-1, and comprises a heavy chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 3 and a light chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 4. Preferably provided is an antibody or an antigen-binding fragment thereof that specifically binds to and neutralizes USAG-1, and comprises a heavy chain variable region comprising an amino acid sequence set forth in SEQ ID NO: 3 and a light chain variable region comprising an amino acid sequence set forth in SEQ ID NO: 4. More preferably provided is an antibody or an antigen-binding fragment thereof that specifically binds to and neutralizes USAG-1, and comprises a heavy chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 3 and a light chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 4. Still more preferably provided is an antibody or an antigen-binding fragment thereof that specifically binds to and neutralizes USAG-1, and comprises a heavy chain variable region consisting of an amino acid sequence set forth in SEQ ID NO: 3 and a light chain variable region consisting of an amino acid sequence set forth in SEQ ID NO: 4.

A further example of antibody A or a mutant thereof includes an antibody or an antigen-binding fragment thereof that specifically binds to and neutralizes USAG-1, comprises a heavy chain variable region comprising an amino acid sequence set forth in SEQ ID NO: 3 and a light chain variable region comprising an amino acid sequence set forth in SEQ ID NO: 4, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises a heavy chain variable region consisting of an amino acid sequence set forth in SEQ ID NO: 3 and a light chain variable region consisting of an amino acid sequence set forth in SEQ ID NO: 4, and comprises substitution, deletion, insertion or addition of one to several amino acid residues in at least one of the above-mentioned amino acid sequences.

An example of antibody B or a mutant thereof includes an antibody or an antigen-binding fragment thereof that specifically binds to and neutralizes USAG-1, and comprises three heavy chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 15, SEQ ID NO: 16 and SEQ ID NO: 17 respectively or three light chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 18, SEQ ID NO: 19 and SEQ ID NO: 20 respectively. Preferably provided is an antibody or an antigen-binding fragment thereof that specifically binds to and neutralizes USAG-1, and comprises three heavy chain complementarity determining regions comprising amino acid sequences set forth in SEQ ID NO: 15, SEQ ID NO: 16 and SEQ ID NO: 17 respectively or three light chain complementarity determining regions comprising amino acid sequences set forth in SEQ ID NO: 18, SEQ ID NO: 19 and SEQ ID NO: 20 respectively. More preferably provided is an antibody or an antigen-binding fragment thereof that specifically binds to and neutralizes USAG-1, and comprises three heavy chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 15, SEQ ID NO: 16 and SEQ ID NO: 17 respectively or three light chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 18, SEQ ID NO: 19 and SEQ ID NO: 20 respectively. Still more preferably provides is an antibody or an antigen-binding fragment thereof that specifically binds to and neutralizes USAG-1, and comprises three heavy chain complementarity determining regions consisting of amino acid sequences set forth in SEQ ID NO: 15, SEQ ID NO: 16 and SEQ ID NO: 17 respectively or three light chain complementarity determining regions consisting of amino acid sequences set forth in SEQ ID NO: 18, SEQ ID NO: 19 and SEQ ID NO: 20 respectively.

A further example of antibody B or a mutant thereof includes an antibody or an antigen-binding fragment thereof that specifically binds to and neutralizes USAG-1, comprises three heavy chain complementarity determining regions comprising amino acid sequences set forth in SEQ ID NO: 15, SEQ ID NO: 16 and SEQ ID NO: 17 respectively or three light chain complementarity determining regions comprising amino acid sequences set forth in SEQ ID NO: 18, SEQ ID NO: 19 and SEQ ID NO: 20 respectively, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises three heavy chain complementarity determining regions consisting of amino acid sequences set forth in SEQ ID NO: 15, SEQ ID NO: 16 and SEQ ID NO: 17 respectively or three light chain complementarity determining regions consisting of amino acid sequences set forth in SEQ ID NO: 18, SEQ ID NO: 19 and SEQ ID NO: 20 respectively, and comprises substitution, deletion, insertion or addition of one to several amino acid residues in at least one of the above-mentioned amino acid sequences.

A further example of antibody B or a mutant includes an antibody or an antigen-binding fragment thereof that specifically binds to and neutralizes USAG-1, and comprises a heavy chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 13 or a light chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 14. Preferably provided is an antibody or an antigen-binding fragment thereof that specifically binds to and neutralizes USAG-1, and comprises a heavy chain variable region comprising an amino acid sequence set forth in SEQ ID NO: 13 or a light chain variable region comprising an amino acid sequence set forth in SEQ ID NO: 14. More preferably provided is an antibody or an antigen-binding fragment thereof that specifically binds to and neutralizes USAG-1, and comprises a heavy chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 13 or a light chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 14. Still more preferably provided is an antibody or an antigen-binding fragment thereof that specifically binds to and neutralizes USAG-1, and comprises a heavy chain variable region consisting of an amino acid sequence set forth in SEQ ID NO: 13 or a light chain variable region consisting of an amino acid sequence set forth in SEQ ID NO: 14.

A further example of antibody B or a mutant thereof includes an antibody or an antigen-binding fragment thereof that specifically binds to and neutralizes USAG-1, comprises a heavy chain variable region comprising an amino acid sequence set forth in SEQ ID NO: 13 or a light chain variable region comprising an amino acid sequence set forth in SEQ ID NO: 14, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises a heavy chain variable region consisting of an amino acid sequence set forth in SEQ ID NO: 13 or a light chain variable region consisting of an amino acid sequence set forth in SEQ ID NO: 14, and comprises substitution, deletion, insertion or addition of one to several amino acid residues in at least one of the above-mentioned amino acid sequences.

A further example of antibody B or a mutant thereof includes an antibody or an antigen-binding fragment thereof that specifically binds to and neutralizes USAG-1, and comprises three heavy chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 15, SEQ ID NO: 16 and SEQ ID NO: 17 respectively and three light chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 18, SEQ ID NO: 19 and SEQ ID NO: 20 respectively. Preferably provided is an antibody or an antigen-binding fragment thereof that specifically binds to and neutralizes USAG-1, and comprises three heavy chain complementarity determining regions comprising amino acid sequences set forth in SEQ ID NO: 15, SEQ ID NO: 16 and SEQ ID NO: 17 respectively and three light chain complementarity determining regions comprising amino acid sequences set forth in SEQ ID NO: 18, SEQ ID NO: 19 and SEQ ID NO: 20 respectively. More preferably provided is an antibody or an antigen-binding fragment thereof that specifically binds to and neutralizes USAG-1, and comprises three heavy chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 15, SEQ ID NO: 16 and SEQ ID NO: 17 respectively and three light chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 18, SEQ ID NO: 19 and SEQ ID NO: 20 respectively. Still more preferably provides is an antibody or an antigen-binding fragment thereof that specifically binds to and neutralizes USAG-1, and comprises three heavy chain complementarity determining regions consisting of amino acid sequences set forth in SEQ ID NO: 15, SEQ ID NO: 16 and SEQ ID NO: 17 respectively and three light chain complementarity determining regions consisting of amino acid sequences set forth in SEQ ID NO: 18, SEQ ID NO: 19 and SEQ ID NO: 20 respectively.

A further example of antibody B or a mutant thereof includes an antibody or an antigen-binding fragment thereof that specifically binds to and neutralizes USAG-1, comprises three heavy chain complementarity determining regions comprising amino acid sequences set forth in SEQ ID NO: 15, SEQ ID NO: 16 and SEQ ID NO: 17 respectively and three light chain complementarity determining regions comprising amino acid sequences set forth in SEQ ID NO: 18, SEQ ID NO: 19 and SEQ ID NO: 20 respectively, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises three heavy chain complementarity determining regions consisting of amino acid sequences set forth in SEQ ID NO: 15, SEQ ID NO: 16 and SEQ ID NO: 17 respectively and three light chain complementarity determining regions consisting of amino acid sequences set forth in SEQ ID NO: 18, SEQ ID NO: 19 and SEQ ID NO: 20 respectively, and comprises substitution, deletion, insertion or addition of one to several amino acid residues in at least one of the above-mentioned amino acid sequences.

A further example of antibody B or a mutant thereof includes an antibody or an antigen-binding fragment thereof that specifically binds to and neutralizes USAG-1, and comprises a heavy chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 13 and a light chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 14. Preferably provided is an antibody or an antigen-binding fragment thereof that specifically binds to and neutralizes USAG-1, and comprises a heavy chain variable region comprising an amino acid sequence set forth in SEQ ID NO: 13 and a light chain variable region comprising an amino acid sequence set forth in SEQ ID NO: 14. More preferably provided is an antibody or an antigen-binding fragment thereof that specifically binds to and neutralizes USAG-1, and comprises a heavy chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 13 and a light chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 14. Still more preferably provided is an antibody or an antigen-binding fragment thereof that specifically binds to and neutralizes USAG-1, and comprises a heavy chain variable region consisting of an amino acid sequence set forth in SEQ ID NO: 13 and a light chain variable region consisting of an amino acid sequence set forth in SEQ ID NO: 14.

A further example of antibody B or a mutant thereof includes an antibody or an antigen-binding fragment thereof that specifically binds to and neutralizes USAG-1, comprises a heavy chain variable region comprising an amino acid sequence set forth in SEQ ID NO: 13 and a light chain variable region comprising an amino acid sequence set forth in SEQ ID NO: 14, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises a heavy chain variable region consisting of an amino acid sequence set forth in SEQ ID NO: 13 and a light chain variable region consisting of an amino acid sequence set forth in SEQ ID NO: 14, and comprises substitution, deletion, insertion or addition of one to several amino acid residues in at least one of the above-mentioned amino acid sequences.

An example of antibody C or a mutant thereof includes an antibody or an antigen-binding fragment thereof that specifically binds to and neutralizes USAG-1, and comprises three heavy chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 25, SEQ ID NO: 26 and SEQ ID NO: 27 respectively or three light chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 28, SEQ ID NO: 29 and SEQ ID NO: 30 respectively. Preferably provided is an antibody or an antigen-binding fragment thereof that specifically binds to and neutralizes USAG-1, and comprises three heavy chain complementarity determining regions comprising amino acid sequences set forth in SEQ ID NO: 25, SEQ ID NO: 26 and SEQ ID NO: 27 respectively or three light chain complementarity determining regions comprising amino acid sequences set forth in SEQ ID NO: 28, SEQ ID NO: 29 and SEQ ID NO: 30 respectively. More preferably provided is an antibody or an antigen-binding fragment thereof that specifically binds to and neutralizes USAG-1, and comprises three heavy chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 25, SEQ ID NO: 26 and SEQ ID NO: 27 respectively, or three light chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 28, SEQ ID NO: 29 and SEQ ID NO: 30 respectively. Still more preferably provides is an antibody or an antigen-binding fragment thereof that specifically binds to and neutralizes USAG-1, and comprises three heavy chain complementarity determining regions consisting of amino acid sequences set forth in SEQ ID NO: 25, SEQ ID NO: 26 and SEQ ID NO: 27 respectively or three light chain complementarity determining regions consisting of amino acid sequences set forth in SEQ ID NO: 28, SEQ ID NO: 29 and SEQ ID NO: 30 respectively.

A further example of antibody C or a mutant thereof includes an antibody or an antigen-binding fragment thereof that specifically binds to and neutralizes USAG-1, comprises three heavy chain complementarity determining regions comprising amino acid sequences set forth in SEQ ID NO: 25, SEQ ID NO: 26 and SEQ ID NO: 27 respectively or three light chain complementarity determining regions comprising amino acid sequences set forth in SEQ ID NO: 28, SEQ ID NO: 29 and SEQ ID NO: 30 respectively, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises three heavy chain complementarity determining regions consisting of amino acid sequences set forth in SEQ ID NO: 25, SEQ ID NO: 26 and SEQ ID NO: 27 respectively or three light chain complementarity determining regions consisting of amino acid sequences set forth in SEQ ID NO: 28, SEQ ID NO: 29 and SEQ ID NO: 30 respectively, and comprises substitution, deletion, insertion or addition of one to several amino acid residues in at least one of the above-mentioned amino acid sequences.

A further example of antibody C or a mutant includes an antibody or an antigen-binding fragment thereof that specifically binds to and neutralizes USAG-1, and comprises a heavy chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 23 or a light chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 24. Preferably provided is an antibody or an antigen-binding fragment thereof that specifically binds to and neutralizes USAG-1, and comprises a heavy chain variable region comprising an amino acid sequence set forth in SEQ ID NO: 23 or a light chain variable region comprising an amino acid sequence set forth in SEQ ID NO: 24. More preferably provided is an antibody or an antigen-binding fragment thereof that specifically binds to and neutralizes USAG-1, and comprises a heavy chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 23 or a light chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 24. Still more preferably provided is an antibody or an antigen-binding fragment thereof that specifically binds to and neutralizes USAG-1, and comprises a heavy chain variable region consisting of an amino acid sequence set forth in SEQ ID NO: 23 or a light chain variable region consisting of an amino acid sequence set forth in SEQ ID NO: 24.

A further example of antibody C or a mutant thereof includes an antibody or an antigen-binding fragment thereof that specifically binds to and neutralizes USAG-1, comprises a heavy chain variable region comprising an amino acid sequence set forth in SEQ ID NO: 23 or a light chain variable region comprising an amino acid sequence set forth in SEQ ID NO: 24, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises a heavy chain variable region consisting of an amino acid sequence set forth in SEQ ID NO: 23 or a light chain variable region consisting of an amino acid sequence set forth in SEQ ID NO: 24, and comprises substitution, deletion, insertion or addition of one to several amino acid residues in at least one of the above-mentioned amino acid sequences.

A further example of antibody C or a mutant thereof includes an antibody or an antigen-binding fragment thereof that specifically binds to and neutralizes USAG-1, and comprises three heavy chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 25, SEQ ID NO: 26 and SEQ ID NO: 27 respectively and three light chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 28, SEQ ID NO: 29 and SEQ ID NO: 30 respectively. Preferably provided is an antibody or an antigen-binding fragment thereof that specifically binds to and neutralizes USAG-1, and comprises three heavy chain complementarity determining regions comprising amino acid sequences set forth in SEQ ID NO: 25, SEQ ID NO: 26 and SEQ ID NO: 27 respectively and three light chain complementarity determining regions comprising amino acid sequences set forth in SEQ ID NO: 28, SEQ ID NO: 29 and SEQ ID NO: 30 respectively. More preferably provided is an antibody or an antigen-binding fragment thereof that specifically binds to and neutralizes USAG-1, and comprises three heavy chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 25, SEQ ID NO: 26 and SEQ ID NO: 27 respectively and three light chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 28, SEQ ID NO: 29 and SEQ ID NO: 30 respectively. Still more preferably provides is an antibody or an antigen-binding fragment thereof that specifically binds to and neutralizes USAG-1, and comprises three heavy chain complementarity determining regions consisting of amino acid sequences set forth in SEQ ID NO: 25, SEQ ID NO: 26 and SEQ ID NO: 27 respectively and three light chain complementarity determining regions consisting of amino acid sequences set forth in SEQ ID NO: 28, SEQ ID NO: 29 and SEQ ID NO: 30 respectively.

A further example of antibody C or a mutant thereof includes an antibody or an antigen-binding fragment thereof that specifically binds to and neutralizes USAG-1, comprises three heavy chain complementarity determining regions comprising amino acid sequences set forth in SEQ ID NO: 25, SEQ ID NO: 26 and SEQ ID NO: 27 respectively and three light chain complementarity determining regions comprising amino acid sequences set forth in SEQ ID NO: 28, SEQ ID NO: 29 and SEQ ID NO: 30 respectively, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises three heavy chain complementarity determining regions consisting of amino acid sequences set forth in SEQ ID NO: 25, SEQ ID NO: 26 and SEQ ID NO: 27 respectively and three light chain complementarity determining regions consisting of amino acid sequences set forth in SEQ ID NO: 28, SEQ ID NO: 29 and SEQ ID NO: 30 respectively, and comprises substitution, deletion, insertion or addition of one to several amino acid residues in at least one of the above-mentioned amino acid sequences.

A further example of antibody C or a mutant thereof includes an antibody or an antigen-binding fragment thereof that specifically binds to and neutralizes USAG-1, and comprises a heavy chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 23 and a light chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 24. Preferably provided is an antibody or an antigen-binding fragment thereof that specifically binds to and neutralizes USAG-1, and comprises a heavy chain variable region comprising an amino acid sequence set forth in SEQ ID NO: 23 and a light chain variable region comprising an amino acid sequence set forth in SEQ ID NO: 24. More preferably provided is an antibody or an antigen-binding fragment thereof that specifically binds to and neutralizes USAG-1, and comprises a heavy chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 23 and a light chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 24. Still more preferably provided is an antibody or an antigen-binding fragment thereof that specifically binds to and neutralizes USAG-1, and comprises a heavy chain variable region consisting of an amino acid sequence set forth in SEQ ID NO: 23 and a light chain variable region consisting of an amino acid sequence set forth in SEQ ID NO: 24.

A further example of antibody C or a mutant thereof includes an antibody or an antigen-binding fragment thereof that specifically binds to and neutralizes USAG-1, comprises a heavy chain variable region comprising an amino acid sequence set forth in SEQ ID NO: 23 and a light chain variable region comprising an amino acid sequence set forth in SEQ ID NO: 24, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises a heavy chain variable region consisting of an amino acid sequence set forth in SEQ ID NO: 23 and a light chain variable region consisting of an amino acid sequence set forth in SEQ ID NO: 24, and comprises substitution, deletion, insertion or addition of one to several amino acid residues in at least one of the above-mentioned amino acid sequences.

An example of antibody D or a mutant thereof includes an antibody or an antigen-binding fragment thereof that specifically binds to and neutralizes USAG-1, and comprises three heavy chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 42, SEQ ID NO: 43 and SEQ ID NO: 44 respectively or three light chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 45, SEQ ID NO: 46 and SEQ ID NO: 47 respectively. Preferably provided is an antibody or an antigen-binding fragment thereof that specifically binds to and neutralizes USAG-1, and comprises three heavy chain complementarity determining regions comprising amino acid sequences set forth in SEQ ID NO: 42, SEQ ID NO: 43 and SEQ ID NO: 44 respectively or three light chain complementarity determining regions comprising amino acid sequences set forth in SEQ ID NO: 45, SEQ ID NO: 46 and SEQ ID NO: 47 respectively. More preferably provided is an antibody or an antigen-binding fragment thereof that specifically binds to and neutralizes USAG-1, and comprises three heavy chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 42, SEQ ID NO: 43 and SEQ ID NO: 44 respectively or three light chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 45, SEQ ID NO: 46 and SEQ ID NO: 47 respectively. Still more preferably provides is an antibody or an antigen-binding fragment thereof that specifically binds to and neutralizes USAG-1, and comprises three heavy chain complementarity determining regions consisting of amino acid sequences set forth in SEQ ID NO: 42, SEQ ID NO: 43 and SEQ ID NO: 44 respectively or three light chain complementarity determining regions consisting of amino acid sequences set forth in SEQ ID NO: 45, SEQ ID NO: 46 and SEQ ID NO: 47 respectively.

A further example of antibody D or a mutant thereof includes an antibody or an antigen-binding fragment thereof that specifically binds to and neutralizes USAG-1, comprises three heavy chain complementarity determining regions comprising amino acid sequences set forth in SEQ ID NO: 42, SEQ ID NO: 43 and SEQ ID NO: 44 respectively or three light chain complementarity determining regions comprising amino acid sequences set forth in SEQ ID NO: 45, SEQ ID NO: 46 and SEQ ID NO: 47 respectively, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises three heavy chain complementarity determining regions consisting of amino acid sequences set forth in SEQ ID NO: 42, SEQ ID NO: 43 and SEQ ID NO: 44 respectively or three light chain complementarity determining regions consisting of amino acid sequences set forth in SEQ ID NO: 45, SEQ ID NO: 46 and SEQ ID NO: 47 respectively, and comprises substitution, deletion, insertion or addition of one to several amino acid residues in at least one of the above-mentioned amino acid sequences.

A further example of antibody D or a mutant includes an antibody or an antigen-binding fragment thereof that specifically binds to and neutralizes USAG-1, and comprises a heavy chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 40 or a light chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 41. Preferably provided is an antibody or an antigen-binding fragment thereof that specifically binds to and neutralizes USAG-1, and comprises a heavy chain variable region comprising an amino acid sequence set forth in SEQ ID NO: 40 or a light chain variable region comprising an amino acid sequence set forth in SEQ ID NO: 41. More preferably provided is an antibody or an antigen-binding fragment thereof that specifically binds to and neutralizes USAG-1, and comprises a heavy chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 40 or a light chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 41. Still more preferably provided is an antibody or an antigen-binding fragment thereof that specifically binds to and neutralizes USAG-1, and comprises a heavy chain variable region consisting of an amino acid sequence set forth in SEQ ID NO: 40 or a light chain variable region consisting of an amino acid sequence set forth in SEQ ID NO: 41.

A further example of antibody D or a mutant thereof includes an antibody or an antigen-binding fragment thereof that specifically binds to and neutralizes USAG-1, comprises a heavy chain variable region comprising an amino acid sequence set forth in SEQ ID NO: 40 or a light chain variable region comprising an amino acid sequence set forth in SEQ ID NO: 41, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises a heavy chain variable region consisting of an amino acid sequence set forth in SEQ ID NO: 40 or a light chain variable region consisting of an amino acid sequence set forth in SEQ ID NO: 41, and comprises substitution, deletion, insertion or addition of one to several amino acid residues in at least one of the above-mentioned amino acid sequences.

A further example of antibody D or a mutant thereof includes an antibody or an antigen-binding fragment thereof that specifically binds to and neutralizes USAG-1, and comprises three heavy chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 42, SEQ ID NO: 43 and SEQ ID NO: 44 respectively and three light chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 45, SEQ ID NO: 46 and SEQ ID NO: 47 respectively. Preferably provided is an antibody or an antigen-binding fragment thereof that specifically binds to and neutralizes USAG-1, and comprises three heavy chain complementarity determining regions comprising amino acid sequences set forth in SEQ ID NO: 42, SEQ ID NO: 43 and SEQ ID NO: 44 respectively and three light chain complementarity determining regions comprising amino acid sequences set forth in SEQ ID NO: 45, SEQ ID NO: 46 and SEQ ID NO: 47 respectively. More preferably provided is an antibody or an antigen-binding fragment thereof that specifically binds to and neutralizes USAG-1, and comprises three heavy chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 42, SEQ ID NO: 43 and SEQ ID NO: 44 respectively and three light chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 45, SEQ ID NO: 46 and SEQ ID NO: 47 respectively. Still more preferably provides is an antibody or an antigen-binding fragment thereof that specifically binds to and neutralizes USAG-1, and comprises three heavy chain complementarity determining regions consisting of amino acid sequences set forth in SEQ ID NO: 42, SEQ ID NO: 43 and SEQ ID NO: 44 respectively and three light chain complementarity determining regions consisting of amino acid sequences set forth in SEQ ID NO: 45, SEQ ID NO: 46 and SEQ ID NO: 47 respectively.

A further example of antibody D or a mutant thereof includes an antibody or an antigen-binding fragment thereof that specifically binds to and neutralizes USAG-1, comprises three heavy chain complementarity determining regions comprising amino acid sequences set forth in SEQ ID NO: 42, SEQ ID NO: 43 and SEQ ID NO: 44 respectively and three light chain complementarity determining regions comprising amino acid sequences set forth in SEQ ID NO: 45, SEQ ID NO: 46 and SEQ ID NO: 47 respectively, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises three heavy chain complementarity determining regions consisting of amino acid sequences set forth in SEQ ID NO: 42, SEQ ID NO: 43 and SEQ ID NO: 44 respectively and three light chain complementarity determining regions consisting of amino acid sequences set forth in SEQ ID NO: 45, SEQ ID NO: 47 and SEQ ID NO: 48 respectively, and comprises substitution, deletion, insertion or addition of one to several amino acid residues in at least one of the above-mentioned amino acid sequences.

A further example of antibody D or a mutant thereof includes an antibody or an antigen-binding fragment thereof that specifically binds to and neutralizes USAG-1, and comprises a heavy chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 40 and a light chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 41. Preferably provided is an antibody or an antigen-binding fragment thereof that specifically binds to and neutralizes USAG-1, and comprises a heavy chain variable region comprising an amino acid sequence set forth in SEQ ID NO: 40 and a light chain variable region comprising an amino acid sequence set forth in SEQ ID NO: 41. More preferably provided is an antibody or an antigen-binding fragment thereof that specifically binds to and neutralizes USAG-1, and comprises a heavy chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 40 and a light chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 41. Still more preferably provided is an antibody or an antigen-binding fragment thereof that specifically binds to and neutralizes USAG-1, and comprises a heavy chain variable region consisting of an amino acid sequence set forth in SEQ ID NO: 40 and a light chain variable region consisting of an amino acid sequence set forth in SEQ ID NO: 41.

A further example of antibody D or a mutant thereof includes an antibody or an antigen-binding fragment thereof that specifically binds to and neutralizes USAG-1, comprises a heavy chain variable region comprising an amino acid sequence set forth in SEQ ID NO: 40 and a light chain variable region comprising an amino acid sequence set forth in SEQ ID NO: 41, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises a heavy chain variable region consisting of an amino acid sequence set forth in SEQ ID NO: 40 and a light chain variable region consisting of an amino acid sequence set forth in SEQ ID NO: 41, and comprises substitution, deletion, insertion or addition of one to several amino acid residues in at least one of the above-mentioned amino acid sequences.

An example of antibody E or a mutant thereof includes an antibody or an antigen-binding fragment thereof that specifically binds to and neutralizes USAG-1, and comprises three heavy chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 52, SEQ ID NO: 53 and SEQ ID NO: 54 respectively or three light chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 55, SEQ ID NO: 56 and SEQ ID NO: 57 respectively. Preferably provided is an antibody or an antigen-binding fragment thereof that specifically binds to and neutralizes USAG-1, and comprises three heavy chain complementarity determining regions comprising amino acid sequences set forth in SEQ ID NO: 52, SEQ ID NO: 53 and SEQ ID NO: 54 respectively or three light chain complementarity determining regions comprising amino acid sequences set forth in SEQ ID NO: 55, SEQ ID NO: 56 and SEQ ID NO: 57 respectively. More preferably provided is an antibody or an antigen-binding fragment thereof that specifically binds to and neutralizes USAG-1, and comprises three heavy chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 52, SEQ ID NO: 53 and SEQ ID NO: 54 respectively or three light chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 55, SEQ ID NO: 56 and SEQ ID NO: 57 respectively. Still more preferably provides is an antibody or an antigen-binding fragment thereof that specifically binds to and neutralizes USAG-1, and comprises three heavy chain complementarity determining regions consisting of amino acid sequences set forth in SEQ ID NO: 52, SEQ ID NO: 53 and SEQ ID NO: 54 respectively or three light chain complementarity determining regions consisting of amino acid sequences set forth in SEQ ID NO: 55, SEQ ID NO: 56 and SEQ ID NO: 57 respectively.

A further example of antibody E or a mutant thereof includes an antibody or an antigen-binding fragment thereof that specifically binds to and neutralizes USAG-1, comprises three heavy chain complementarity determining regions comprising amino acid sequences set forth in SEQ ID NO: 52, SEQ ID NO: 53 and SEQ ID NO: 54 respectively or three light chain complementarity determining regions comprising amino acid sequences set forth in SEQ ID NO: 55, SEQ ID NO: 56 and SEQ ID NO: 57 respectively, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises three heavy chain complementarity determining regions consisting of amino acid sequences set forth in SEQ ID NO: 52, SEQ ID NO: 53 and SEQ ID NO: 54 respectively or three light chain complementarity determining regions consisting of amino acid sequences set forth in SEQ ID NO: 55, SEQ ID NO: 56 and SEQ ID NO: 57 respectively, and comprises substitution, deletion, insertion or addition of one to several amino acid residues in at least one of the above-mentioned amino acid sequences.

A further example of antibody E or a mutant includes an antibody or an antigen-binding fragment thereof that specifically binds to and neutralizes USAG-1, and comprises a heavy chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 50 or a light chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 51. Preferably provided is an antibody or an antigen-binding fragment thereof that specifically binds to and neutralizes USAG-1, and comprises a heavy chain variable region comprising an amino acid sequence set forth in SEQ ID NO: 50 or a light chain variable region comprising an amino acid sequence set forth in SEQ ID NO: 51. More preferably provided is an antibody or an antigen-binding fragment thereof that specifically binds to and neutralizes USAG-1, and comprises a heavy chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 50 or a light chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 51. Still more preferably provided is an antibody or an antigen-binding fragment thereof that specifically binds to and neutralizes USAG-1, and comprises a heavy chain variable region consisting of an amino acid sequence set forth in SEQ ID NO: 50 or a light chain variable region consisting of an amino acid sequence set forth in SEQ ID NO: 51.

A further example of antibody E or a mutant thereof includes an antibody or an antigen-binding fragment thereof that specifically binds to and neutralizes USAG-1, comprises a heavy chain variable region comprising an amino acid sequence set forth in SEQ ID NO: 50 or a light chain variable region comprising an amino acid sequence set forth in SEQ ID NO: 51, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises a heavy chain variable region consisting of an amino acid sequence set forth in SEQ ID NO: 50 or a light chain variable region consisting of an amino acid sequence set forth in SEQ ID NO: 51, and comprises substitution, deletion, insertion or addition of one to several amino acid residues in at least one of the above-mentioned amino acid sequences.

A further example of antibody E or a mutant thereof includes an antibody or an antigen-binding fragment thereof that specifically binds to and neutralizes USAG-1, and comprises three heavy chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 52, SEQ ID NO: 53 and SEQ ID NO: 54 respectively and three light chain complementarity determining regions comprising amino acid sequences having at least 80%, 85%, 90%, 91%, 92%, 93%, 94%, 95%, 96%, 97%, 98% or 99% sequence identity with amino acid sequences set forth in SEQ ID NO: 55, SEQ ID NO: 56 and SEQ ID NO: 57 respectively. Preferably provided is an antibody or an antigen-binding fragment thereof that specifically binds to and neutralizes USAG-1, and comprises three heavy chain complementarity determining regions comprising amino acid sequences set forth in SEQ ID NO: 52, SEQ ID NO: 53 and SEQ ID NO: 54 respectively and three light chain complementarity determining regions comprising amino acid sequences set forth in SEQ ID NO: 55, SEQ ID NO: 56 and SEQ ID NO: 57 respectively. More preferably provided is an antibody or an antigen-binding fragment thereof that specifically binds to and neutralizes USAG-1, and comprises three heavy chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 52, SEQ ID NO: 53 and SEQ ID NO: 54 respectively and three light chain complementarity determining regions consisting of amino acid sequences having at least 80%, 85%, 90%, 91%, 92%, 93%, 94%, 95%, 96%, 97%, 98% or 99% sequence identity with amino acid sequences set forth in SEQ ID NO: 55, SEQ ID NO: 56 and SEQ ID NO: 57 respectively. Still more preferably provides is an antibody or an antigen-binding fragment thereof that specifically binds to and neutralizes USAG-1, and comprises three heavy chain complementarity determining regions consisting of amino acid sequences set forth in SEQ ID NO: 52, SEQ ID NO: 53 and SEQ ID NO: 54 respectively and three light chain complementarity determining regions consisting of amino acid sequences set forth in SEQ ID NO: 55, SEQ ID NO: 56 and SEQ ID NO: 57 respectively.

A further example of antibody E or a mutant thereof includes an antibody or an antigen-binding fragment thereof that specifically binds to and neutralizes USAG-1, comprises three heavy chain complementarity determining regions comprising amino acid sequences set forth in SEQ ID NO: 52, SEQ ID NO: 53 and SEQ ID NO: 54 respectively and three light chain complementarity determining regions comprising amino acid sequences set forth in SEQ ID NO: 55, SEQ ID NO: 56 and SEQ ID NO: 57 respectively, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises three heavy chain complementarity determining regions consisting of amino acid sequences set forth in SEQ ID NO: 52, SEQ ID NO: 53 and SEQ ID NO: 54 respectively and three light chain complementarity determining regions consisting of amino acid sequences set forth in SEQ ID NO: 55, SEQ ID NO: 56 and SEQ ID NO: 57 respectively, and comprises substitution, deletion, insertion or addition of one to several amino acid residues in at least one of the above-mentioned amino acid sequences.

A further example of antibody E or a mutant thereof includes an antibody or an antigen-binding fragment thereof that specifically binds to and neutralizes USAG-1, and comprises a heavy chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 50 and a light chain variable region comprising an amino acid sequence having at least 80%, 85%, 90%, 91%, 92%, 93%, 94%, 95%, 96%, 97%, 98% or 99% sequence identity with an amino acid sequence set forth in SEQ ID NO: 51. Preferably provided is an antibody or an antigen-binding fragment thereof that specifically binds to and neutralizes USAG-1, and comprises a heavy chain variable region comprising an amino acid sequence set forth in SEQ ID NO: 50 and a light chain variable region comprising an amino acid sequence set forth in SEQ ID NO: 51. More preferably provided is an antibody or an antigen-binding fragment thereof that specifically binds to and neutralizes USAG-1, and comprises a heavy chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 50 and a light chain variable region consisting of an amino acid sequence having at least 80%, 85%, 90%, 91%, 92%, 93%, 94%, 95%, 96%, 97%, 98% or 99% sequence identity with an amino acid sequence set forth in SEQ ID NO: 51. Still more preferably provided is an antibody or an antigen-binding fragment thereof that specifically binds to and neutralizes USAG-1, and comprises a heavy chain variable region consisting of an amino acid sequence set forth in SEQ ID NO: 50 and a light chain variable region consisting of an amino acid sequence set forth in SEQ ID NO: 51.

A further example of antibody E or a mutant thereof includes an antibody or an antigen-binding fragment thereof that specifically binds to and neutralizes USAG-1, comprises a heavy chain variable region comprising an amino acid sequence set forth in SEQ ID NO: 50 and a light chain variable region comprising an amino acid sequence set forth in SEQ ID NO: 51, and comprises substitution, deletion, insertion or addition of one to several amino acid residues in at least one of the above-mentioned amino acid sequences. Preferably provided is an antibody or an antigen-binding fragment thereof that specifically binds to and neutralizes USAG-1, comprises a heavy chain variable region consisting of an amino acid sequence set forth in SEQ ID NO: 50 and a light chain variable region consisting of an amino acid sequence set forth in SEQ ID NO: 51, and comprises substitution, deletion, insertion or addition of one to several amino acid residues in at least one of the above-mentioned amino acid sequences.

As used herein, the term “several” means about 2 to 10, and preferably means, depending on the length of an amino acid sequence, about 2 to 7, for example, 3, 4, 5, or 6. As used herein, the “substitution” may be a conservative or non-conservative substitution, and preferably a conservative substitution. Conservative substitution is known to those skilled in the art, and refers to a substitution that does not affect the biological activity of the resulting molecule. Examples of conservative amino acid substitution include a substitution of alanine to glycine or serine, a substitution of arginine to lysine or histidine, a substitution of asparagine to glutamine or histidine, a substitution of aspartic acid to glutamic acid or asparagine, a substitution of cysteine to serine or alanine, a substitution of glutamine to asparagine, a substitution of glutamic acid to aspartic acid or glutamine, a substitution of glycine to alanine, a substitution of histidine to asparagine or glutamine, a substitution of isoleucine to leucine or valine, a substitution of leucine to isoleucine or valine, a substitution of lysine to arginine or histidine, a substitution of methionine to leucine, isoleucine or tyrosine, a substitution of phenylalanine to tyrosine, methionine or leucine, a substitution of proline to alanine, a substitution of serine to threonine, a substitution of threonine to serine, a substitution of tryptophan to tyrosine or phenylalanine, a substitution of tyrosine to tryptophan or phenylalanine, and a substitution of valine to isoleucine or leucine.

As used herein, the sequence identity may be determined in optimal alignment of two sequences according to a conventional method. For example, the sequence identity may be determined using an algorithm known in the art, such as BLAST or FASTA. The antibody or antigen-binding fragment thereof of the present disclosure may comprise substitution, deletion, insertion or addition of an amino acid residue(s) within the above-mentioned range of sequence identity.

Further, in another aspect of the present invention, an antibody or an antigen-binding fragment thereof that binds to a whole extent or a part of the same epitope as an epitope on USAG-1 to which the antibody A, antibody B, antibody C, antibody D or antibody E, or a mutant thereof, or an antigen-binding fragment thereof binds is provided as the antibody or antigen-binding fragment thereof of the present disclosure. Furthermore, the present invention provides an antibody or an antigen-binding fragment thereof that competes with the antibody A, antibody B, antibody C, antibody D or antibody E, or a mutant thereof, or an antigen-binding fragment thereof for binding to USAG-1 or for binding to a whole extent or a part of an epitope on USAG-1.

Furthermore, in the present invention, the antibody A was found to recognize and bind a polypeptide (epitope) comprising VNDKTRTQRI (SEQ ID NO: 31) on human USAG-1 (corresponding to a sequence of the 134th to 143rd amino acids of human USAG-1 protein). Therefore, an antibody or an antigen-binding fragment thereof that binds to a USAG-1 polypeptide comprising the amino acid sequence set forth in SEQ ID NO: 31 is also an aspect of the antibody or antigen-binding fragment thereof of the present disclosure. Further, an antibody or an antigen-binding fragment thereof that competes with the antibody A or a mutant thereof or an antigen-binding fragment thereof for binding to a USAG-1 polypeptide comprising the amino acid sequence set forth in SEQ ID NO: 31 is also an aspect of the antibody or antigen-binding fragment thereof of the present disclosure. For example, the USAG-1 polypeptide may be a polypeptide consisting of the amino acid sequence set forth in SEQ ID NO: 31. The USAG-1 polypeptide comprising the amino acid sequence set forth in SEQ ID NO: 31 may be substantially the same polypeptide as the USAG-1 polypeptide comprising the amino acid sequence set forth in SEQ ID NO: 31. Examples of the substantially same polypeptide include a polypeptide located at the corresponding positions on USAG-1 protein of an animal other than human.

As used herein, the term “competition” means that an antibody or an antigen-binding fragment thereof competes with a reference antibody (e.g., antibody A, antibody B, antibody C, antibody D, antibody E, or a mutant thereof, or an antigen-binding fragment thereof) in a binding assay using an USAG-1 protein or polypeptide. For example, if a test antibody or an antigen-binding fragment thereof reduces the binding of a reference antibody to an USAG-1 protein or polypeptide in the binding assay, the test antibody “competes” with the reference antibody. An antibody that competes with a reference antibody, for example, reduces the binding of the reference antibody to an antigen protein or polypeptide by at least about 40%, preferably at least about 50%, more preferably at least about 60%, still more preferably at least about 80%, or still more preferably at least 90%. The competitive binding assay can be performed by known methods in the art including, but not limited to, ELISA, flow cytometry, SPR (surface plasmon resonance), and BLI (Bio-Layer Interferometry).

Epitope binning is a technique for classifying two or more antibodies based on their epitopes, for example, by using SPR or BLI. In epitope binning, for example, an antigen protein (target) is added to a biosensor on which a reference antibody is immobilized to allow the reference antibody to bind the target, the biosensor holding a complex of the reference antibody and the target is reacted with a test antibody, and then, binding of the test antibody to the biosensor (i.e., binding of the test antibody to the target captured by the reference antibody immobilized on the biosensor) and dissociation of the binding are analyzed. If the test antibody shares the same epitope with the reference antibody, the test antibody cannot bind to the biosensor because the epitope on the target is already occupied by the binding of the reference antibody. Conversely, if the test antibody recognizes a different epitope from that recognized by the reference antibody, the test antibody can bind to the biosensor. Furthermore, if the test antibody recognizes a region sterically close to an epitope recognized by the reference antibody, the test antibody cannot bind to the biosensor because the binding of the reference antibody to the target interferes with the binding of the test antibody to the epitope. Thus, use of epitope binning enables to determine whether two or more antibody clones compete for binding to a target protein.

The antibody or antigen-binding fragment thereof of the present disclosure binds to USAG-1 or a whole extent or a part of an epitope on USAG-1 at a KD of for example 1 μM or less, preferably 100 nM or less, more preferably 50 nM or less, still more preferably 30 nM or less, still more preferably 10 nM or less, still more preferably 8 nM or less, or still more preferably 5 nM or less.

In the present invention, the antibody is preferably an isolated antibody. In the present invention, the antibody may be a polyclonal antibody or a monoclonal antibody. In the present invention, the antibody may be a human antibody, a humanized antibody, a chimeric antibody, or a multispecific antibody (for example, a bispecific antibody). The humanized antibody includes a human immunoglobulin (recipient antibody) in which the complementarity determining regions (CDRs) of a recipient are replaced by residues from the CDRs of a non-human species (donor antibody) having desired specificity, affinity and binding ability. Optionally, the Fv framework region (FR) residues of the human immunoglobulin may be replaced by the corresponding non-human residues. In addition, the humanized antibody may comprise residues that are not found in the recipient antibody or the donor antibody. Generally, humanized antibodies comprise at least one variable region, typically two variable regions, in which all or substantially all CDRs are replaced by non-human immunoglobulin CDRs and all or substantially all of FR regions consist of human immunoglobulin sequences. The chimeric antibody includes an antibody produced by a genetic recombination technique in which variable regions derived from a donor antibody are linked to constant regions of a recipient antibody. The above antibodies can be produced by methods known in the art.

In the present invention, examples of the antigen-binding fragment include, but not limited to, $F(ab')_2$, Fab', Fab, Fv, rIgG, Fd, a linear antibody, ScFv, Fv-clasp, a minibody, a diabody, a triabody, a tetrabody, a single domain antibody (nanobody), and a multispecific antibody formed from antibody fragments. The antibody fragments can be prepared by methods known in the art.

An isolated nucleic acid encoding the antibody or antigen-binding fragment thereof of the present disclosure is also included in the present invention.

The antibody or antigen-binding fragment thereof of the present disclosure specifically binds to USAG-1 to inhibit the function of USAG-1 and then induce tooth formation. Accordingly, another aspect of the present invention provides a pharmaceutical composition for dental regeneration therapy comprising the antibody or antigen-binding fragment thereof of the present disclosure. The dental regeneration includes, for example, regeneration of a missing tooth (recovery of a missing tooth), and formation of a new tooth such as a third dentition.

The pharmaceutical composition of the present disclosure may contain a pharmaceutically acceptable carrier, and an additive such as a stabilizer or an excipient, in addition to the antibody or antigen-binding fragment thereof of the present disclosure. Examples of the pharmaceutically acceptable carrier include, but not limited to, physiological saline, buffer, glycol, glycerol, gelatin, gelatin hydrogel, polylactic acid, collagen sponge, agarose, polyvinyl alcohol, alginic acid, fibrin gel, an ethylene-vinyl acetate copolymer, and a lactic acid-glycolic acid copolymer. Examples of the additive include, but not limited to, a carbohydrate such as glucose, sucrose or dextran, an antioxidant such as ascorbic acid or glutathione, a chelating agent, and a low molecular weight protein. Those skilled in the art can appropriately select the carrier and additive as mentioned above based on an administration form, administration route or the like of the pharmaceutical composition. Pharmaceutical composition of the present disclosure can be produced using the antibody or antigen-binding fragment thereof, and the additive as appropriate by a conventional method.

Examples of the form of the pharmaceutical composition of the present disclosure include a tablet, a powder, a capsule, a granule, a syrup, a sustained release tablet, a sustained release capsule, an enteric coated drug, an intercalating drug, an infusion, and an injection. A preferable example thereof is an injection. The pharmaceutical composition of the present disclosure is systemically or topically administered. The administration route may be appropriately selected by those skilled in the art, and examples thereof include, but not limited to, oral, nasal, subcutaneous, intravenous, intramuscular, and intraosseous administration. The pharmaceutical composition of the present disclosure may be locally administered, for example, to the site of tooth formation.

In the present invention, the dental regenerative therapy includes the treatment of congenital tooth agenesis and the treatment of acquired tooth loss. Congenital tooth agenesis that can be treated with the pharmaceutical composition of the present disclosure is not particularly limited, and may also include congenital tooth agenesis due to any causative gene. Examples of congenital tooth agenesis that can be treated with the pharmaceutical composition of the present disclosure include, but not limited to, congenital tooth agenesis whose causative gene is RUNX2, MSX1, EDA, WNT10A, PAX9, or AXIN2. Preferable examples thereof include congenital tooth agenesis whose causative gene is RUNX2, MSX1, EDA, or WNT10A. Further, the antibody of the present disclosure induced the formation of supernumerary teeth in wild-type mice. Therefore, the pharmaceutical composition of the present disclosure can induce tooth formation even in normal individuals in which the causative gene of tooth agenesis is not deficient and individuals losing teeth after birth.

Pharmaceutical composition of the present disclosure may be administered to a mammal. Examples of the mammal include a human, a dog, a cat, a horse, a mouse, a ferret, a suncus, a pig, and a monkey. A preferable example thereof is a human.

A dose of the pharmaceutical composition of the present disclosure is not particularly limited. The dose can be appropriately determined by those skilled in the art based on the amount of the antibody or antigen-binding fragment thereof of the present disclosure contained in the pharmaceutical composition, the body weight of a subject to be administered, etc. so that a desired dose of the antibody or antigen-binding fragment thereof of the present disclosure can be administered. For example, the antibody or antigen-binding fragment thereof of the present disclosure is administered in an amount that produces a neutralizing activity such that BMP signaling is increased by at least 30%, preferably at least 60% and/or a neutralizing activity such that Wnt signaling is increased by at least 30%, preferably at least 60%, as compared with the case where the antibody or antigen-binding fragment thereof of the present disclosure is not administered. The neutralizing activities may be determined based on the activity measured in vitro by, for example, an ALP assay or a reporter assay.

A further aspect of the present invention provides a method of regenerating a tooth which comprises administering the antibody or antigen-binding fragment thereof of the present disclosure to a subject in need. The above-mentioned pharmaceutical composition can be used as the antibody or antigen-binding fragment thereof of the present disclosure. The subject in need is a subject having a missing tooth, and examples of the subject include mammals as mentioned above. A route of administration and a dose of the antibody or antigen-binding fragment thereof of the present disclosure, and the treatment for tooth regeneration are as described above for the pharmaceutical composition of the present disclosure.

Hereinafter, the present invention will be described in more detail with reference to Examples which the present invention is not limited to.

Example 1

Preparation of Antibody 1

For preparation of mouse USAG-1 neutralizing antibodies, a human USAG-1 protein derived from an *Escherichia coli* expression system (R & D systems) was used as an antigen. In a Wnt reporter assay using HEK293 cells, the Wnt inhibitory activity of the *Escherichia coli* expression system-derived human USAG-1 protein was confirmed (FIG. 1). In an ALP assay with addition of BMP7 using C2C12 cells, the BMP inhibitory activity of the *Escherichia coli* expression system-derived human USAG-1 protein was confirmed (FIG. 2). For preparation of mouse USAG-1 neutralizing antibodies, three lines of supernumerary tooth model mice, USAG-1KO mice (#116, #118, #138) were newly established using CRISPR-CAS9 (FIG. 3). The neutralizing antibodies were prepared using USAG-1 KO (#116) mice by an iliac lymph node method in ITM Co., Ltd.

Primary screening of 284 wells was performed by ELISA using the immunizing antigen, and a large number of positive wells were found (FIG. 4-1 and FIG. 4-2). Based on a cutoff value of 0.7, 79 clones were selected. After expansion, ELISA was performed using the immunizing antigen and a mouse USAG-1 protein derived from a CHO cell expression system that was prepared by Sysmex Corporation. When a cut-off value of absorbance was set to 0.025 or more, positive wells were found in about half of the clones (FIG. 4-1 and FIG. 4-2). As a result of measurement of antibody subclasses, they were found to be IgG1, 2a, 2b, and 2c (FIG. 4-1 and FIG. 4-2).

The neutralizing activity of each antibody was confirmed as follows. In an experimental system in which an ALP activity in C2C12 cells increased by addition of 300 ng/ml of BMP7 (manufactured by R & D systems) was suppressed by addition of 300 ng/ml of a mammalian cell expression system-derived rat USAG-1 protein (manufactured by MyBiosource), each antibody was added to confirm neutralization of the suppressed ALP activity. The antibodies were classified into a group of those having mild neutralizing activity (*: 60-100% neutralizing activity), a group of those having moderate neutralizing activity (: 100-140% neutralizing activity), and a group of those having high neutralizing activity (*: 140% or more neutralizing activity). For a BMP reporter assay, a commercially available cell line incorporating BRE-Luc, BMP Responsive Reporter Osteoblast Cell Line (Briter cell) (manufactured by Kerafast, Inc.) was used. In an experimental system in which a luciferase activity expressed by addition of 300 ng/ml of BMP7 was suppressed by addition of 300 ng/ml of the mammalian cell expression system-derived rat USAG-1 protein, each antibody was added to confirm neutralization of the suppressed luciferase activity. The antibodies were classified into a group of those having mild neutralizing activity (*: 40-60% neutralizing activity) and a group of those having moderate neutralizing activity (**: 60% or more neutralizing activity). For the WNT reporter assay, an expression plasmid for expressing a TOP-Flash reporter gene having a DNA sequence to bind transcription factor TCF that activates downstream of the WNT signaling, a WNT1 gene, and a reporter gene under the control of an HSV-thymidine kinase promoter for obtaining an internal standard value was introduced into HEK293 cells, and the cells were cultured with addition of the mammalian cell expression system-derived rat USAG-1 protein at a concentration (EC50) for producing 50% of the maximum inhibitory effect on Wnt signaling. An addition amount of the USAG-1 protein was determined in advance. A culture supernatant of an antibody-producing hybridoma was added to the cells so as to be 25%, 20% or 10% in a medium for screening. The experiment was performed three times for evaluation. When added at 25%, the antibodies were classified into a group of those having mild neutralizing activity (*: a luminescence correction value of 1.5-2.0) and a group of those having moderate neutralizing activity (**: a luminescence correction value of 2.0 or more). When added at 20%, the antibodies were classified into a group of those having mild neutralizing activity (*: a luminescence correction value of 1-1.1) and a group of those having moderate neutralizing activity (**: a luminescence correction value of 1.1 or more). When added at 10%, the antibodies were classified into a group of those having mild neutralizing activity (*: a luminescence correction value of 1-1.1) and a group of those having moderate neutralizing activity (**: a luminescence correction value of 1.1 or more). The % of neutralizing activity was calculated based on the activity (100%) under the condition of no addition of USAG-1 protein. Neutralizing activity based on the luminescence value was calculated as a value relative to the activity (1) when no antibody was added.

As measured by the WNT and BMP reporter assays and the BMP7 ALP assay, there were three types of neutralizing antibodies: antibodies that activate either BMP or WNT signaling, and antibodies that simultaneously activate both BMP and WNT signaling. Six antibodies were selected based on the measurement results of neutralizing activity (FIG. 4-1 and FIG. 4-2). The activity of one clone disappeared during expansion and purification processes. Finally, 5 kinds of mouse anti-USAG-1 neutralizing antibodies (E12, E16, E37, E48, E57) were obtained.

Of these, E37 (referred to as antibody A) and E57 (referred to as antibody B) were sequenced. A full-length heavy chain sequence containing a signal sequence and a full-length light chain sequence containing a signal sequence of antibody A are shown in SEQ ID NO: 1 and SEQ ID NO: 2, respectively. A full-length heavy chain sequence containing a signal sequence and a full-length light chain sequence containing a signal sequence of antibody B are shown in SEQ ID NO: 11 and SEQ ID NO: 12, respectively. Variable regions of antibodies A and B are shown in FIG. 14.

Example 2

In Vitro Test of Antibody—1

A mouse USAG-1 (WISE) recombinant protein with a PA tag added to the N-terminal was transiently expressed in Expi293F cells, and a stable expression line was established. Affinity purification was performed using a PA tag system to obtain 0.2 mg of PA-mUSAG-1 (WISE) from 150 mL of a culture supernatant (FIG. 5). The purified PA-mUSAG-1 (WISE) protein was shown to have a molecular weight of about 28 kDa, which is close to the theoretical value (24 kDa), by electrophoresis under reduction (R) and non-reduction (NR). The N-terminal PA-tagged mouse USAG-1 (WISE) protein derived from the mammalian cell Expi293F cell expression system showed dose-dependent WNT signaling inhibitory activity in the WNT reporter assay (FIG. 6) and dose-dependent BMP signaling inhibitory activity in the BMP ALP assay (FIG. 7). The mouse USAG-1 protein whose activity was confirmed was used to confirm the neutralizing activity of 5 mouse anti-USAG-1 neutralizing antibodies (E12, E16, E37, E48, E57). In the WNT reporter assay, cells into which a vector containing a luciferase gene ligated to a promoter and a vector for expressing Wnt1 were introduced were cultured in a medium with addition of 1.7 μg of the mouse USAG-1 recombinant protein and the antibody in an amount of 1/1000, 1/300 or 1/100 of the medium, and luciferase activity was measured. In the BMP ALP assay, C2C12 cells were cultured with 30 ng/ml of the mouse USAG-1 recombinant protein and a 1-fold (30 ng/ml), 10-fold (300 ng/ml) or 100-fold (3 μg/ml) amount of the antibody in the presence of 30 ng/ml of BMP7, and ALP activity was measured.

As a result, in the WNT reporter assay, the existence of antibodies that dose-dependently neutralized the WNT signaling inhibitory activity of the mouse USAG-1 was found (FIG. 8). In the BMP ALP assay, the existence of antibodies that dose-dependently neutralized the BMP signaling inhibitory activity of the mouse USAG-1 was found (FIG. 9).

Example 3

In Vivo Administration Test of Antibody—1

A congenital tooth agenesis model mouse with homozygous EDA-deficiency has high loss (about 90%) of a mandibular third molar (M3). A single dose of the mouse anti-USAG-1 neutralizing antibody A (E37) was intraperitoneally administered to mother mice pregnant with congenital tooth agenesis model mouse due to EDA deficiency. As a result, loss of the mandibular third molar (M3) was recovered in 7 out of 8 born EDA-deficient mice (FIG. 10). No supernumerary tooth was observed in the congenital tooth agenesis model mouse with EDA deficiency to which the mouse anti-USAG-1 neutralizing antibody A was administered. Therefore, it was found that the antibody A can recover a missing tooth. Here, the term "recovery" means that a born EDA-deficient mouse has a tooth at the site (does not lose M3) where a tooth is normally lost in an EDA-deficient mouse.

Example 4

In Vivo Administration Test of Antibody—2

A single dose of the mouse anti-USAG-1 neutralizing antibody B (E57) was intraperitoneally administered to mother mice pregnant with congenital tooth agenesis model mouse due to EDA deficiency. As a result, formation of a supernumerary tooth at an anterior tooth site or a fused tooth at a maxillary molar site was induced in 2 out of 3 born EDA-deficient homozygous mice (FIG. 10). In 5 out of 5 born EDA-deficient heterozygous mice, a supernumerary tooth at an anterior tooth site or a fused tooth at a molar site was observed. Furthermore, when the mouse anti-USAG-1 neutralizing antibody B (E57) was intraperitoneally administered in a single dose to mother mice pregnant with wild-type mice, a supernumerary tooth at an anterior tooth site or a fused tooth at a molar site was observed in 11 out of 12 born wild-type mice (FIG. 11). Therefore, it was found that the antibody B can increase the number of teeth in EDA-deficient homozygous mice, EDA-deficient heterozygous mice, and wild-type mice.

Example 5

In Vivo Administration Test of Antibody—3

A mixture of the five types of anti-USAG-1 neutralizing antibodies obtained in Example 1 including the antibodies A and B was intraperitoneally administered in a single dose to mother mice pregnant with Wnt10a-deficient mice which are tooth agenesis model mice. As a result, a supernumerary tooth was formed at maxillary anterior tooth site (FIG. 10).

Example 6

Data on Human USAG-1 Recognition by Antibody

This Example was performed to confirm that the five types of mouse anti-USAG-1 (WISE) neutralizing antibodies (E12, E16, E37, E48, E57) obtained using the *Escherichia coli* expression system-derived human USAG-1 protein as an antigen in Example 1 recognize human USAG-1 protein. A binding assay was performed using mouse/human N-terminal PA-tagged USAG-1 proteins. Each of the five mouse anti-USAG-1 (WISE) neutralizing antibodies (E12, E16, E37, E48, E57) obtained in Example 1 (5 μg in 1 ml PBS) was captured on Protein A sepharose (30 μl) (room temperature, 2.5 hours). A culture supernatant (1 mL) of Expi293F cells transiently expressing a human or mouse N-terminal PA-tagged USAG-1 (WISE) recombinant protein and NZ1 sepharose (30 μl) were added to the Protein A sepharose, and then incubated (room temperature, 2.5 hours). Washing with a PBS buffer was performed 3 times to remove unbound proteins. All proteins bound to the sepharose were eluted, and bands were detected by SDS-PAGE electrophoresis. As a result, it was found that all of the five antibodies bound not only to the mouse USAG-1 but also to the human USAG-1 protein (FIG. 12).

Furthermore, a human FLAG-tagged USAG-1 cDNA was transiently forcibly expressed in HEK293 cells, and then subjected to immunostaining using 5 types of mouse anti-USAG-1 neutralizing antibodies (E12, E16, E37, E48, E57). As a result, clear positive reaction was observed when the neutralizing antibodies (E12, E37, E57) were used. Therefore, it was found that both the mouse anti-USAG-1 neutralizing antibody A (E37) and the mouse anti-USAG-1 neutralizing antibody B (E57) whose efficacy was confirmed in vivo recognize the human USAG-1 protein. (FIG. 13).

Example 7

Preparation of Antibody—2

For preparation of mouse USAG-1 neutralizing antibodies, a rat USAG-1 protein derived from a baculovirus expression system was used as an antigen. The neutralizing antibodies were prepared by the iliac lymph node method using USAG-1 KO (#116) mice. The baculovirus expression system-derived rat USAG-1 protein was shown to have BMP inhibitory activity and Wnt inhibitory activity in the same manner as described in Example 1. Primary screening of the obtained antibody clones was performed by ELISA using the immunizing antigen (the baculovirus expression system-derived rat USAG-1 protein) and the *Escherichia coli* expression system-derived human USAG-1 protein, and a large number of positive wells were found. Based on a cut-off value of 1.0, 111 clones were selected. After expansion, the clones were subjected to sandwich ELISA using the immunizing antigen. When a cut-off value of absorbance was set to 0.5 or more (His tag) or 1.4 or more (Myc tag), positive wells were found in about half of the clones. As a result of measurement of antibody subclasses, they were found to be IgG1, 2a, 2b, and G3. Further, the neutralizing activity of the obtained antibodies was measured in the same manner as described in Example 1. Finally, four types of mouse anti-USAG-1 neutralizing antibodies (B14, B48, B103, B108) were obtained. Further, in the same manner as in Example 6, a binding assay was performed using moue/human N-terminal PA-tagged USAG-1 proteins to confirm that the obtained mouse anti-USAG-1 neutralizing antibodies (B14, B48, B103, B108) recognize the human USAG-1 protein. Each of the mouse anti-USAG-1 neutralizing antibodies [5 μg in 250 μl protein A/G IgG binding buffer (Pierce™)+250 μl PBS] was captured on Protein A sepharose (30 μl) (room temperature, 1.5 hours). A culture supernatant (0.75 mL) of Expi293F cells transiently expressing a human or mouse N-terminal PA-tagged USAG-1 (WISE) recombinant protein was added to the Protein A sepharose, and then incubated (room temperature, 2 hours). Washing with a PBS buffer was performed 3 times to remove unbound proteins. All proteins bound to the sepharose were eluted, and bands were detected by SDS-PAGE electrophoresis and CBB (Coomassie Brilliant Blue) staining. As a result, all of the tested mouse anti-USAG-1 neutralizing antibodies bound to both the mouse USAG-1 and the human USAG-1 protein (FIG. 15), though the binding of B103 and B108 was weaker than that of B14 and B48.

Of these, B14 (referred to as antibody C) was sequenced. A full-length heavy chain sequence containing a signal sequence and a full-length light chain sequence containing a signal sequence of antibody C are shown in SEQ ID NO: 21 and SEQ ID NO: 22, respectively. Variable regions of antibody C are shown in FIG. 21. Further, B48 (referred to as antibody D) and B103 (referred to as antibody E) were sequenced. Full-length heavy chain sequences containing a signal sequence of antibodies D and E are shown in SEQ ID NO: 38 and SEQ ID NO: 48, respectively. Full-length light chain sequences containing a signal sequence of antibodies D and E are shown in SEQ ID NO: 39 and SEQ ID NO: 49, respectively. Variable regions of antibodies D and E are shown in FIG. 22.

Example 8

Epitope Binning

The five mouse USAG-1 neutralizing antibodies (E12, E16, E37, E48, E57) selected in Example 1 and the neutralizing antibodies (B14, B48, B103, B108) prepared in Example 7 were subjected to epitope binning. FIG. 16 shows comparison of 6 types of antibodies among the obtained competitive binding data. Epitope binning was performed using Octet (registered trademark) Red (manufactured by Pall ForteBio). Briefly, each of the nine antibodies was immobilized on a biosensor as a capture antibody, a target comprising a purified full-length recombinant mouse USAG-1 was added to bind the capture antibody, and then the biosensor was reacted with a test antibody to detect a binding signal. This cycle was repeated in succession using 9 test antibodies including the same antibody as used for capture. An antibody that does not compete with the capture antibody immobilized on the biosensor for the recognition site can bind to the captured USAG-1 protein, and thus the signal increases. In contrast, a competing antibody weakly binds to the captured USAG-1 protein, and thus no increase or little increase in the signal was observed. Based on the signal data obtained, the 9 antibodies were grouped based on their epitopes. Specifically, in a reaction of a test antibody with the sensor immobilizing any of the nine capture antibodies, when the reaction generated a signal equal to or weaker than a signal (indicated by a bold underline in FIG. 16) generated when the same antibody as the capture antibody was added, the test antibody was regarded as belonging to the same group as the capture antibody. As a result, E37 and E48 competed with the E12 antibody, E48, E57 and B14 competed with the E16 antibody, E12 competed with the E37 antibody, E16, E57 and B14 competed with the E48 antibody, E16, E48 and B14 competed with the E57 antibody, E16, E48 and E57 competed with the B14 antibody, and B108 competed with the B103 antibody. Based on these results, the 9 kinds of antibodies were classified into 4 groups as shown in Table 1. However, the E48 antibody was also close to group 1 because it competes with E12, though the E48 antibody was basically classified into group 2.

TABLE 1

| Group | Antibody |
|---|---|
| 1 | E12 |
| | E37 (Neutralizing antibody A) |
| 2 | E16 |
| | E48 |
| | E57 (Neutralizing antibody B) |
| | B14 (Neutralizing antibody C) |
| 3 | B48 (Neutralizing antibody D) |
| 4 | B103 (Neutralizing antibody E) |
| | B108 |

Example 9

Epitope Mapping

The antibody E37 (neutralizing antibody A) of group 1 was subjected to epitope mapping. Briefly, 169 overlapping peptides of 15 amino acids were synthesized based on a human USAG-1 protein sequence (183 amino acid length) excluding a signal peptide by shifting the 15 amino acid sequence from the beginning by one amino acid to prepare a peptide library. The 169 kinds of peptides were bound onto a cellulose membrane to prepare a peptide array. The E37 antibody (0.3 g/ml) was added as a primary antibody and incubated. After washing, an HRP-conjugated anti-mouse antibody (1/25000 dilution) was added as a secondary antibody, and ECL solution was used for color development.

As a result, the E37 antibody was found to specifically bind to 6 peptides: QEWRCVNDKTRTQRI (SEQ ID NO: 32), EWRCVNDKTRTQRIQ (SEQ ID NO: 33), WRCVNDKTRTQRIQL (SEQ ID NO: 34), RCVNDKTRTQRIQLQ (SEQ ID NO: 35), CVNDKTRTQRIQLQC (SEQ ID NO: 36), and VNDKTRTQRIQLQCQ (SEQ ID No: 37). Therefore, the amino acid sequence: VNDKTRTQRI (SEQ ID NO: 31) (corresponding to positions 134 to 143 in the full-length USAG-1 amino acid sequence containing the signal peptide) was identified as an epitope.

Example 10

In Vitro Test of Antibody—2

For 8 out of the 9 antibodies grouped in Example 8, affinities (KD values) were determined by using the same Octet-based BLI method as in Example 8. Specifically, each antibody was immobilized on the biosensor, the purified recombinant mouse USAG-1 protein was added at three different concentrations (10 nM, 30 nM, 100 nM), and binding and dissociation curves were obtained. The affinities were calculated by subjecting the obtained curves to global fitting with an analysis program attached to the Octet device. Results are shown in Table 2.

TABLE 2

| Antibody | KD (nM) |
|---|---|
| E12 | 3.86 |
| E16 | 7.15 |
| E37 (Neutralizing antibody A) | 2.43 |
| E48 | 3.92 |
| E57 (Neutralizing antibody B) | 2.44 |
| B14 (Neutralizing antibody C) | 4.21 |
| B48 (Neutralizing antibody D) | 3.26 |
| B103 (Neutralizing antibody E) | 4.97 |

Example 11

In Vitro Test of Antibody—3

The BMP and Wnt signaling inhibition neutralizing activities of the antibody B14 that was classified into group 2 in Example 8 were determined. Experiments were carried out in the same manner as in Example 2. Specifically, in the WNT reporter assay, cells into which a vector containing a luciferase gene ligated to a promoter and a vector for expressing Wnt1 (1 μg) were introduced were cultured in a medium with addition of 1 μg of the mouse USAG-1 recombinant protein and the antibody in an amount of 1.0, 3.0, 4.0, 6.0, 8.0, 10.0, 12.0, 15.0, or 30.0 μg/ml medium, and luciferase activity was measured. In the BMP ALP assay, C2C12 cells were cultured with 30 ng/ml of the mouse USAG-1 recombinant protein and 30 ng/ml, 150 ng/ml, 300 ng/ml or 1500 ng/ml of the antibody in the presence of 30 ng/ml of BMP7, and ALP activity was measured. Results are shown in FIG. 17. In the WNT reporter assay, the antibody B14 was shown to neutralize the WNT signaling inhibitory activity of USAG-1 (up to 42% neutralizing activity). In the BMP ALP assay, that antibody B14 was shown to neutralize the BMP signaling inhibitory activity of USAG-1.

Further, for obtaining the EC50 value of the antibody B14 against the inhibition of BMP and Wnt signaling by USAG-1, the concentration at the time of 50% inhibition was calculated, wherein the neutralizing activity by no addition of the antibody was defined as 0% and the maximal neutralizing activity was defined as 100%. As a result, the EC50 values were 298 ng/ml and 4.73 μg/ml against the BMP and Wnt signaling inhibition, respectively.

Example 12

In Vivo Administration Test of Antibody—4 (Mouse)

The six antibodies classified into groups 1 and 2 in Example 8 were intraperitoneally administered in a single dose to mother mice pregnant with congenital tooth agenesis model mouse due to EDA homozygous deficiency, congenital tooth agenesis model mouse due to EDA heterozygous deficiency, or wild-type mice. Results are shown in Table 3. All of the six antibodies were found to induce the formation of a supernumerary tooth and/or a fused tooth in the EDA-deficient mice, and increase the number of teeth in the EDA-deficient mice. Particularly, the antibodies of group 1 recovered missing teeth in the EDA-deficient mice. When the antibodies of group 1 were administered, the formation of a supernumerary tooth and a fused tooth was not observed in the wild-type mice. In contrast, the antibodies E57 and B14 of group 2 induced the formation of a supernumerary tooth and a fused tooth in the wild-type mice. The antibody B14 (antibody C) and the antibody E57 (antibody B) were found to increase the number of teeth in all EDA homozygous deficient mice, EDA heterozygous deficient mice and wild-type mice. Here, the term "recovery" means that a born EDA-deficient mouse has a tooth at the site (does not lose M3) where a tooth is normally lost in an EDA-deficient mouse.

TABLE 3

| | | | $EDA^{+/-}$ mouse | $EDA^{-/-}$ mouse | |
|---|---|---|---|---|---|
| Ab | Dose | $EDA^{+/+}$ (wild-type) mouse | Supernumerary tooth/Fused tooth | Recovery | Supernumerary tooth/Fused tooth |
| E12 | 16 ug/g body weight × 7 mice | 0/2 | 1/3 | 2/2 | 0/2 |
| | 48 ug/g body weight × 7 mice | 0/2 | 0/3 | 0/2 | 0/2 |
| | 80 ug/g body weight × 4 mice | 0/3 | 0/1 | | |
| | Total 18 mice | 0/7 | 1/7 (14%) | 2/4 | 0/4 |
| E16 | 8 ug/g body weight × 7 mice | 0/2 | 1/3 | 2/2 | 0/2 |
| | 16 ug/g body weight × 9 mice | 0/2 | 0/4 | 2/3 | 0/3 |
| | 32 ug/g body weight × 5 mice | 0/4 | 1/1 | | |
| | Total 21 mice | 0/8 | 2/8 (25%) | 4/5 (80%) | 0/5 |
| E37 | 8 ug/g body weight × 12 mice | 0/6 | | 3/6 | 0/6 |
| | 16 ug/g body weight × 16 mice | 0/5 | 1/5 | 5/6 | 0/6 |
| | 32 ug/g body weight × mice | 0/2 | 1/2 | 2/2 | 0/2 |
| | 48 ug/g body weight × 5 mice | 0/2 | 0/3 | | |
| | Total 39 mice | 0/15 | 2/10 (20%) | 10/14 (71%) | 0/14 |
| E48 | 8 ug/g body weight × 1 mouse | | 0/1 | | |
| | 16 ug/g body weight × 6 mice | 0/1 | 0/1 | 3/4 | 0/4 |
| | Total 7 mice | 0/1 | 0/2 | 3/4 (75%) | 0/4 |
| E57 | 8 ug/g body weight × 5 mice | 0/2 | 0/2 | 1/1 | 0/1 |
| | 16 ug/g body weight × 8 mice | 5/6 | 1/1 | 0/1 | 1/1 |
| | 32 ug/g body weight × 5 mice | 3/3 | 2/2 | | |
| | 48 ug/g body weight × 6 mice | 3/3 | 2/2 | 1/1 | 1/1 |
| | Total 24 mice | 11/14 (79%) | 5/7 (71%) | 2/3 (66%) | 2/3 (67%) |
| B14 | 0.16 ug/g body weight × 6 mice | 0/3 | 0/2 | 1/1 | 0/1 |
| | 8 ug/g body weight × 8 mice | 0/2 | 2/2 | 2/4 | 0/4 |
| | 16 ug/g body weight × 12 mice | 2/2 | 3/3 | 5/5 | 0/2 |
| | 32 ug/g body weight × 6 mice | 1/1 | 1/2 | 2/3 | 2/3 |
| | 48 ug/g body weight × 5 mice | 1/1 | 2/2 | 2/2 | 2/2 |
| | Total 37 mice | 4/9 (44%) | 8/11 (73%) | 12/15 (80%) | 4/15 (27%) |

Example 13

In Vivo Administration Test of Antibody—5 (Dog)

The anti-mouse USAG-1 neutralizing antibody B14 (50 μg/g body weight) was intraperitoneally administered in a single dose to congenital tooth agenesis model dogs immediately after birth. The congenital tooth agenesis model dogs were individuals developing congenital tooth agenesis of a TOYO beagle line and obtained from KITAYAMA LABES CO., LTD., Hongo Farm. The congenital tooth agenesis model dogs include individuals lacking maxillary third premolars and individuals lacking mandibular fourth premolars. Ten weeks after the administration, calcification of tooth germs was evaluated by dental X-ray radiography. As a result, recovery of missing teeth was found (FIG. 18). Results are shown in Table 4. In addition, the blood concentration of the administered antibody in each individual was measured 3 days, 1 week, 3 weeks, 5 weeks and 7 weeks after the antibody administration. As a result, though there were individual differences, the half-life was 1 week and the antibody in blood was maintained until 7 weeks after administration.

TABLE 4

| Gr. | Basic phenotype | Father/ Mother | Antibody administration | Recovery in each group | Recovery at each lacking site | Total |
|---|---|---|---|---|---|---|
| A | Lack of both maxillary 3rd premolars | 7MW661/ 8FW1301 | (+)<br>(−) | 2/3 (67%)<br>1/5 (20%) | 2/5 (40%)<br>1/7 (14%) | Antibody administration (+) 3/9 (33%) |
| C | Lack of both maxillary 3rd premolars | 7MW661/ 8FW1302 | (+)<br>(−) | 0/2 (0%)<br>0/2 (0%) | | Antibody administration (−) 2/12 (17%) |
| B | Lack of both mandibular 4th premolars | 7MW504/ 8FW1304 | (+)<br>(−) | 0/3 (0%)<br>1/3 (33%) | 1/4 (25%)<br>1/5 (20%) | |
| D | Lack of both mandibular 4th premolars | 7MW504/ 8FW1303 | (+)<br>(−) | 1/1 (100%)<br>0/2 (0%) | | |

As is clear from Table 4, the congenital absent premolars were recovered by single systemic administration of the USAG-1 neutralizing antibody B14. The low recovery rate of absent mandibular premolars are probably due to different causative genes.

Example 14

In Vivo Administration Test of Antibody—6 (Ferret)

Ferrets are diphyodont like humans, and have the number of teeth according to a dental formula consisting of three incisors, one canine, three premolars and two molars, which is similar to the basic dental formula of mammals. Thirty-nine USAG-1 neutralizing antibodies (16 μg/g body weight) including the antibodies prepared in Examples 1 and 7 were intraperitoneally administered to 39 ferrets 1 and 3 weeks after birth (one ferret per each antibody). Fourteen weeks after birth, 38 ferrets survived. Four ferrets to which 4 kinds of antibodies including the antibodies of groups 1 to 4 identified in Example 8 were administered and were observed for a long period of time until 30 weeks after birth. As a result, many large-sized teeth were observed at the sites of the maxillary and mandibular anterior tooth and premolars in two or more ferrets. Furthermore, in the ferret to which the antibody B14 was administered, 14 weeks after birth, induction of the third dentition was observed at the sites of mandibular third premolars on the lingual sides (FIG. 19). In the ferret to which the antibody B103 was administered, 30 weeks after birth, one more anterior tooth appeared on the maxillary lingual (palatal) side, and induction of the third dentition was observed at the maxillary anterior tooth site (FIG. 23). The anterior tooth developed after permanent tooth development, and was similar to the preceding permanent tooth in morphology. The anterior tooth had a short dental root. Furthermore, in the ferret to which the antibody B103 was administered, 30 weeks after birth, induction of the third dentition was observed at the sites of the mandibular left and right premolars (FIG. 24).

Example 15

In Vivo Administration Test of Antibody—7 (Suncus)

Pregnant house musk shrews (suncus) were obtained, and on the 17th day of pregnancy, various USAG-1 neutralizing antibodies (16 μg/g body weight) prepared in Example 1 were intraperitoneally administered. Seven weeks after birth, evaluation was performed by μCT imaging. The house musk shrews which received the USAG-1 neutralizing antibodies did not give birth. However, in the 4 to 8 month-old parent house musk shrew which received the antibody B (E57) or the antibody C (B14), formation of a new tooth was observed around a dental root, where enamel epithelial stem cells topically induced epithelial mesenchymal transition. In the house musk shrew which received the antibody B, induction of the third dentition was observed between the mandibular first and second premolars on the buccal side (FIG. 20). Therefore, the USAG-1 neutralizing antibodies of the present invention were shown to induce the formation of the third dentition.

Example 16

In Vitro Test of Antibody—4

The BMP and Wnt signaling inhibition neutralizing activities of the antibody B48 that was classified into group 3 in Example 8 were determined. Experiments were carried out in the same manner as in Example 2. Specifically, in the WNT reporter assay, cells into which a vector containing a luciferase gene ligated to a promoter and a vector for expressing Wnt1 (1 μg) were introduced were cultured in a medium with addition of 1 μg of the mouse USAG-1 recombinant protein and the antibody in an amount of 1, 3, 6, 10 or 30 μg/ml medium, and luciferase activity was measured. In the BMP ALP assay, C2C12 cells were cultured with 30 ng/ml of the mouse USAG-1 recombinant protein and a 1-fold (30 ng/ml), 10-fold (300 ng/ml) or 100-fold (3 μg/ml) amount of the antibody in the presence of 30 ng/ml of BMP7, and ALP activity was measured. Results are shown in FIG. 25. In the WNT reporter assay, the antibody B48 was shown to neutralize the WNT signaling inhibitory activity of USAG-1 by almost 100%.

Example 17

In Vitro Test of Antibody—5 (Pull-Down Assay with Protein A Sepharose Using PA-Tagged USAG-1 and E1E2)

Wnt binds to Frizzled and its co-receptor, a low-density lipoprotein receptor-related protein (LRP) 5/6 receptor to transmit a signal in cells. LRP6 has four extracellular domains (E1 to E4). Among the domains, E1E2 is known to be involved in the binding of USAG-1. Specifically, USAG-1 binds to the E1E2 region of LRP6 to inhibit Wnt signaling. Thus, the 9 kinds of mouse anti-USAG-1 neutralizing antibodies (E12, E16, E37, E48, E57, B14, B48, B103, B108) grouped in Example 8 were used to determine whether the binding of USAG-1 to LRP6-E1E2 was inhibited.

Each mouse anti-USAG-1 neutralizing antibody (5 μg in 1 ml PBS) was captured on Protein A sepharose (30 μl) (room temperature, 1.5 hours). A culture supernatant (1 mL) of Expi293F cells transiently expressing a N-terminal PA-tagged mouse USAG-1 recombinant protein was added to the Protein A sepharose, and then incubated (room temperature, 2 hours). Then, a culture supernatant (1 mL) expressing LRP6-E1E2 (a region of amino acid numbers 1 to 629 of human LRP6, fused to a His tag) was added, and incubated (room temperature, 2.5 hours). Washing with a PBS buffer (1 mL) was performed 3 times to remove unbound proteins. All proteins bound to the sepharose were eluted, and bands were detected by SDS-PAGE electrophoresis and Oriole gel fluorescence staining. Results are shown in FIG. 26. In FIG. 26, the right panel shows results obtained when the same experiment was performed except that the mouse anti-USAG-1 neutralizing antibody was not captured (no mAb) as a negative control, when a complex of the mouse USAG-1 recombinant protein and LRP6-E1E2 was immunoprecipitated with a PA-tagged antibody NZ-1 (WISE+E1E2 By NZ1) as a positive control, and when the expression level of LRP6-E1E2 only was precipitated with a Ni-NTA resin capable of adsorbing the His tag (E1E2 By NiNTA).

As a result, it was found that LRP6-E1E2 did not bind to complexes of some antibodies (particularly the antibodies B48, B103, B108 of groups 3 and 4) with USAG-1 (FIG. 26). Therefore, the epitopes of these antibodies overlap or are in a region sterically close to the LRP6 binding site of USAG-1, and the antibodies bind to USAG-1 to inhibit the binding of USAG-1 to LRP6, and thereby the inhibition of Wnt signaling by USAG-1 was neutralized.

Example 18

In Vivo Administration Test of Antibody—8 (Mouse)

The three antibodies classified into groups 3 and 4 in Example 8 were intraperitoneally administered in a single dose to mother mice pregnant with congenital tooth agenesis model mouse due to EDA homozygous deficiency, congenital tooth agenesis model mouse due to EDA heterozygous deficiency, or wild-type mice (16 μg/g body weight). In born offspring mice, the presence of supernumerary teeth and fused teeth and the presence or absence of recovery of missing teeth were examined. Results are shown in Table 5. The three antibodies particularly recovered missing teeth in the EDA-deficient mice. Herein, the term "recovery" means that a born EDA-deficient mouse has a tooth at the site (does not lose M3) where a tooth is normally lost in an EDA-deficient mouse.

TABLE 5

| | $EDA^{+/+}$ (wild-type) mouse | $EDA^{+/-}$ mouse | $EDA^{-/-}$ mouse | |
|---|---|---|---|---|
| Antibody | Supernumerary tooth/Fused tooth | Supernumerary tooth/Fused tooth | Recovery | Supernumerary tooth/Fused tooth |
| B48 | 0/1 | 0/1 | 3/4 (75%) | 1/4 |
| B103 | 0/5 | 0/2 | 2/2 | 0/2 |
| B108 | 0/1 | — | 3/3 | 0/3 |

Example 19

In Vivo Administration Test of Antibody—9 (Mouse)

Five kinds of antibodies (E57, B14, B48, B103, B108) were intraperitoneally administered in a single dose to mother mice pregnant with congenital tooth agenesis model mouse Wnt10a homozygous deficient mice, congenital tooth agenesis model mouse Wnt10a heterozygous deficient mice, or wild-type mice (2 μg/g body weight for B103, 16 μg/g body weight for the other antibodies). In born offspring mice, the presence of supernumerary teeth and fused teeth and the presence or absence of recovery of missing teeth were examined. Results are shown in Table 6. Of the antibodies in groups 3 and 4, B48 and B103 induced the formation of supernumerary teeth and fused teeth in the homozygous deficient mice.

TABLE 6

| Antibody | $Wnt10a^{+/+}$ (wild-type) mouse Supernumerary tooth/Fused tooth | $Wnt10a^{+/-}$ mouse Supernumerary tooth/Fused tooth | $Wnt10a^{-/-}$ mouse Supernumerary tooth/Fused tooth |
|---|---|---|---|
| E57 | 3/5 (60%) | 14/29 (48%) | 11/14 (79%) |
| B14 | 5/5 (100%) | 2/3 (67%) | 0/0 |
| B48 | 0/2 | 0/9 | 2/5 (40%) |
| B103 | 0/1 | 0/3 | 1/4 (25%) |

INDUSTRIAL APPLICABILITY

The antibody or antigen-binding fragment thereof of the present disclosure can be used for the treatment of congenital tooth agenesis and acquired tooth loss. In addition, the antibody or antigen-binding fragment thereof of the present disclosure is effective for the formation of the third dentition. Thus, the antibody or antigen-binding fragment thereof of the present disclosure leads to development of a molecular-targeted drug for tooth regeneration in the pharmaceutical field and establishment of a dental regenerative therapy based on formation of the third dentition.

SEQUENCE LISTING FREE TEXT

SEQ ID NO: 32; 15 amino acid peptide for epitope mapping

SEQ ID NO: 33; 15 amino acid peptide for epitope mapping

SEQ ID NO: 34; 15 amino acid peptide for epitope mapping

SEQ ID NO: 35; 15 amino acid peptide for epitope mapping

SEQ ID NO: 36; 15 amino acid peptide for epitope mapping

SEQ ID NO: 37; 15 amino acid peptide for epitope mapping

The invention claimed is:

1. An antibody or antigen-binding fragment thereof that specifically binds to and neutralizes USAG-1, the antibody or antigen-binding fragment thereof comprising:

three heavy chain complementarity determining regions that comprise amino acid sequences set forth in SEQ ID NO: 15, SEQ ID NO: 16 and SEQ ID NO: 17 respectively, and three light chain complementarity determining regions that comprise amino acid sequences set forth in SEQ ID NO: 18, SEQ ID NO: 19 and SEQ ID NO: 20 respectively;

three heavy chain complementarity determining regions that comprise amino acid sequences set forth in SEQ ID NO: 25, SEQ ID NO: 26 and SEQ ID NO: 27 respectively, and three light chain complementarity determining regions that comprise amino acid sequences set forth in SEQ ID NO: 28, SEQ ID NO: 29 and SEQ ID NO: 30 respectively; or three heavy chain complementarity determining regions that comprise amino acid sequences set forth in SEQ ID NO: 52, SEQ ID NO: 53 and SEQ ID NO: 54 respectively, and three light chain complementarity determining regions that comprise amino acid sequences set forth in SEQ ID NO: 55, SEQ ID NO: 56 and SEQ ID NO: 57 respectively.

2. The antibody or antigen fragment thereof according to claim 1, which specifically binds to USAG-1 and neutralizes BMP signaling inhibitory activity of USAG-1.

3. The antibody or antigen fragment thereof according to claim 1, which specifically binds to USAG-1 and neutralizes WNT signaling inhibitory activity of USAG-1.

4. The antibody or antigen-binding fragment thereof according to claim 1, which comprises:

a heavy chain variable region that comprises an amino acid sequence having at least 90% sequence identity with an amino acid sequence set forth in SEQ ID NO: 13, and a light chain variable region that comprises an amino acid sequence having at least 90% sequence identity with an amino acid sequence set forth in SEQ ID NO: 14;

a heavy chain variable region that comprises an amino acid sequence having at least 90% sequence identity with an amino acid sequence set forth in SEQ ID NO: 23, and a light chain variable region that comprises an amino acid sequence having at least 90% sequence identity with an amino acid sequence set forth in SEQ ID NO: 24;

or a heavy chain variable region that comprises an amino acid sequence having at least 90% sequence identity with an amino acid sequence set forth in SEQ ID NO: 50, and a light chain variable region that comprises an amino acid sequence having at least 90% sequence identity with an amino acid sequence set forth in SEQ ID NO: 51.

5. The antibody or antigen-binding fragment thereof according to claim 1, wherein the antibody is a humanized antibody or a chimeric antibody.

6. A pharmaceutical composition for dental regenerative therapy, which comprises the antibody or antigen-binding fragment thereof according to claim 1.

7. The antibody or antigen-binding fragment thereof according to claim 1, which comprises three heavy chain complementarity determining regions that comprise the amino acid sequences set forth in SEQ ID NO: 15, SEQ ID NO: 16 and SEQ ID NO: 17 respectively, and three light chain complementarity determining regions that comprise the amino acid sequences set forth in SEQ ID NO: 18, SEQ ID NO: 19 and SEQ ID NO: 20 respectively.

8. The antibody or antigen-binding fragment thereof according to claim 1, which comprises three heavy chain complementarity determining regions that comprise the amino acid sequences set forth in SEQ ID NO: 25, SEQ ID NO: 26 and SEQ ID NO: 27 respectively, and three light chain complementarity determining regions that comprise the amino acid sequences set forth in SEQ ID NO: 28, SEQ ID NO: 29 and SEQ ID NO: 30 respectively.

9. The antibody or antigen-binding fragment thereof according to claim 1, which comprises three heavy chain complementarity determining regions that comprise the amino acid sequences set forth in SEQ ID NO: 52, SEQ ID NO: 53 and SEQ ID NO: 54 respectively, and three light chain complementarity determining regions that comprise the amino acid sequences set forth in SEQ ID NO: 55, SEQ ID NO: 56 and SEQ ID NO: 57 respectively.

10. The antibody or antigen-binding fragment thereof according to claim 1, which comprises a heavy chain variable region that comprises an amino acid sequence having at least 90% sequence identity with an amino acid sequence set forth in SEQ ID NO: 13, and a light chain variable region that comprises an amino acid sequence having at least 90% sequence identity with an amino acid sequence set forth in SEQ ID NO: 14.

11. The antibody or antigen-binding fragment thereof according to claim 1, which comprises a heavy chain variable region that comprises an amino acid sequence having at least 90% sequence identity with an amino acid sequence set forth in SEQ ID NO: 23, and a light chain variable region that comprises an amino acid sequence having at least 90% sequence identity with an amino acid sequence set forth in SEQ ID NO: 24.

12. The antibody or antigen-binding fragment thereof according to claim 1, which comprises a heavy chain variable region that comprises an amino acid sequence having at least 90% sequence identity with an amino acid sequence set forth in SEQ ID NO: 50, and a light chain variable region that comprises an amino acid sequence having at least 90% sequence identity with an amino acid sequence set forth in SEQ ID NO: 51.

13. The antibody or antigen-binding fragment thereof according to claim 1, which comprises a heavy chain variable region that comprises an amino acid sequence having at least 95% sequence identity with an amino acid sequence set forth in SEQ ID NO: 13, and a light chain variable region that comprises an amino acid sequence having at least 95% sequence identity with an amino acid sequence set forth in SEQ ID NO: 14.

14. The antibody or antigen-binding fragment thereof according to claim 1, which comprises a heavy chain variable region that comprises an amino acid sequence having at least 95% sequence identity with an amino acid sequence set forth in SEQ ID NO: 23, and a light chain variable region that comprises an amino acid sequence having at least 95% sequence identity with an amino acid sequence set forth in SEQ ID NO: 24.

15. The antibody or antigen-binding fragment thereof according to claim 1, which comprises a heavy chain variable region that comprises an amino acid sequence having at least 95% sequence identity with an amino acid sequence set forth in SEQ ID NO: 50, and a light chain variable region that comprises an amino acid sequence having at least 95% sequence identity with an amino acid sequence set forth in SEQ ID NO: 51.

16. The antibody or antigen-binding fragment thereof according to claim 1, which comprises a heavy chain variable region that comprises an amino acid sequence having at least 98% sequence identity with an amino acid sequence set forth in SEQ ID NO: 13, and a light chain variable region that comprises an amino acid sequence having at least 98% sequence identity with an amino acid sequence set forth in SEQ ID NO: 14.

17. The antibody or antigen-binding fragment thereof according to claim 1, which comprises a heavy chain variable region that comprises an amino acid sequence having at least 98% sequence identity with an amino acid sequence set forth in SEQ ID NO: 23, and a light chain variable region that comprises an amino acid sequence having at least 98% sequence identity with an amino acid sequence set forth in SEQ ID NO: 24;

or a heavy chain variable region that comprises an amino acid sequence having at least 98% sequence identity with an amino acid sequence set forth in SEQ ID NO: 50, and a light chain variable region that comprises an amino acid sequence having at least 98% sequence identity with an amino acid sequence set forth in SEQ ID NO: 51.

18. The antibody or antigen-binding fragment thereof according to claim 1, which comprises a heavy chain variable region that comprises the amino acid sequence set forth in SEQ ID NO: 13, and a light chain variable region that comprises an amino acid sequence set forth in SEQ ID NO: 14.

19. The antibody or antigen-binding fragment thereof according to claim 1, which comprises a heavy chain variable region that comprises the amino acid sequence set forth in SEQ ID NO: 23, and a light chain variable region that comprises an amino acid sequence set forth in SEQ ID NO: 24.

20. The antibody or antigen-binding fragment thereof according to claim 1, which comprises a heavy chain variable region that comprises the amino acid sequence set forth in SEQ ID NO: 50, and a light chain variable region that comprises an amino acid sequence set forth in SEQ ID NO: 51.

* * * * *

SEQUENCE LISTING

```
<160> NUMBER OF SEQ ID NOS: 57

<210> SEQ ID NO 1
<211> LENGTH: 467
<212> TYPE: PRT
<213> ORGANISM: Mus musculus

<400> SEQUENCE: 1

Met Glu Trp Ser Trp Val Ser Leu Phe Phe Leu Ser Val Thr Thr Gly
1               5                   10                  15

Val His Ser Gln Val Gln Leu Gln Gln Ser Asp Ala Glu Leu Val Asn
            20                  25                  30

Pro Gly Ala Ser Val Lys Ile Ser Cys Lys Val Ser Gly Tyr Thr Phe
        35                  40                  45

Thr Asp His Thr Ile His Trp Met Lys Gln Arg Pro Glu Gln Gly Leu
    50                  55                  60

Glu Trp Ile Gly Tyr Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Tyr Phe Cys Ala Arg Thr Glu Thr Tyr Tyr Gly Arg Ile Tyr Tyr Tyr
        115                 120                 125

Ala Met Asp Tyr Trp Gly Gln Gly Thr Ser Val Thr Val Ser Ser Ala
    130                 135                 140

Lys Thr Thr Pro Pro Ser Val Tyr Pro Leu Ala Pro Gly Ser Ala Ala
145                 150                 155                 160

Gln Thr Asn Ser Met Val Thr Leu Gly Cys Leu Val Lys Gly Tyr Phe
                165                 170                 175

Pro Glu Pro Val Thr Val Thr Trp Asn Ser Gly Ser Leu Ser Ser Gly
            180                 185                 190

Val His Thr Phe Pro Ala Val Leu Gln Ser Asp Leu Tyr Thr Leu Ser
        195                 200                 205

Ser Ser Val Thr Val Pro Ser Ser Thr Trp Pro Ser Gln Thr Val Thr
    210                 215                 220

Cys Asn Val Ala His Pro Ala Ser Ser Thr Lys Val Asp Lys Lys Ile
225                 230                 235                 240

Val Pro Arg Asp Cys Gly Cys Lys Pro Cys Ile Cys Thr Val Pro Glu
                245                 250                 255

Val Ser Ser Val Phe Ile Phe Pro Pro Lys Pro Lys Asp Val Leu Thr
            260                 265                 270

Ile Thr Leu Thr Pro Lys Val Thr Cys Val Val Val Asp Ile Ser Lys
        275                 280                 285

Asp Asp Pro Glu Val Gln Phe Ser Trp Phe Val Asp Asp Val Glu Val
    290                 295                 300

His Thr Ala Gln Thr Lys Pro Arg Glu Glu Gln Ile Asn Ser Thr Phe
```

-continued

```
305                 310                 315                 320

Arg Ser Val Ser Glu Leu Pro Ile Met His Gln Asp Trp Leu Asn Gly
                325                 330                 335

Lys Glu Phe Lys Cys Arg Val Asn Ser Ala Ala Phe Pro Ala Pro Ile
            340                 345                 350

Glu Lys Thr Ile Ser Lys Thr Lys Gly Arg Pro Lys Ala Pro Gln Val
        355                 360                 365

Tyr Thr Ile Pro Pro Pro Lys Glu Gln Met Ala Lys Asp Lys Val Ser
    370                 375                 380

Leu Thr Cys Met Ile Thr Asn Phe Phe Pro Glu Asp Ile Thr Val Glu
385                 390                 395                 400

Trp Gln Trp Asn Gly Gln Pro Ala Glu Asn Tyr Lys Asn Thr Gln Pro
                405                 410                 415

Ile Met Asp Thr Asp Gly Ser Tyr Phe Val Tyr Ser Lys Leu Asn Val
            420                 425                 430

Gln Lys Ser Asn Trp Glu Ala Gly Asn Thr Phe Thr Cys Ser Val Leu
        435                 440                 445

His Glu Gly Leu His Asn His His Thr Glu Lys Ser Leu Ser His Ser
    450                 455                 460

Pro Gly Lys
465


<210> SEQ ID NO 2
<211> LENGTH: 234
<212> TYPE: PRT
<213> ORGANISM: Mus musculus

<400> SEQUENCE: 2

Met Asp Phe Gln Val Gln Ile Phe Ser Phe Leu Leu Ile Ser Ala Ser
1               5                   10                  15

Val Ile Leu Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met Tyr Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ile Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205
```

-continued

```
His Asn Ser Tyr Thr Cys Glu Ala Thr His Lys Thr Ser Thr Ser Pro
    210                 215                 220

Ile Val Lys Ser Phe Asn Arg Asn Glu Cys
225                 230


<210> SEQ ID NO 3
<211> LENGTH: 124
<212> TYPE: PRT
<213> ORGANISM: Mus musculus

<400> SEQUENCE: 3

Gln Val Gln Leu Gln Gln Ser Asp Ala Glu Leu Val Asn Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Tyr Pro Gly Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Thr Glu Thr Tyr Tyr Gly Arg Ile Tyr Tyr Tyr Ala Met Asp
            100                 105                 110

Tyr Trp Gly Gln Gly Thr Ser Val Thr Val Ser Ser
        115                 120


<210> SEQ ID NO 4
<211> LENGTH: 105
<212> TYPE: PRT
<213> ORGANISM: Mus musculus

<400> SEQUENCE: 4

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Ala Thr Ser Asn Leu Ala Ser Gly Val Pro Ile Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Leu Thr Phe
                85                  90                  95

Gly Ala Gly Thr Lys Leu Glu Leu Lys
            100                 105


<210> SEQ ID NO 5
<211> LENGTH: 8
<212> TYPE: PRT
<213> ORGANISM: Mus musculus

<400> SEQUENCE: 5

Gly Tyr Thr Phe Thr Asp His Thr
1               5
```

-continued

<210> SEQ ID NO 6
<211> LENGTH: 8
<212> TYPE: PRT
<213> ORGANISM: Mus musculus

<400> SEQUENCE: 6

```
Ile Tyr Pro Gly Asp Gly Ser Thr
1               5
```

<210> SEQ ID NO 7
<211> LENGTH: 17
<212> TYPE: PRT
<213> ORGANISM: Mus musculus

<400> SEQUENCE: 7

```
Ala Arg Thr Glu Thr Tyr Tyr Gly Arg Ile Tyr Tyr Tyr Ala Met Asp
1               5                   10                  15

Tyr
```

<210> SEQ ID NO 8
<211> LENGTH: 5
<212> TYPE: PRT
<213> ORGANISM: Mus musculus

<400> SEQUENCE: 8

```
Ser Ser Val Ser Tyr
1               5
```

<210> SEQ ID NO 9
<211> LENGTH: 3
<212> TYPE: PRT
<213> ORGANISM: Mus musculus

<400> SEQUENCE: 9

```
Ala Thr Ser
1
```

<210> SEQ ID NO 10
<211> LENGTH: 8
<212> TYPE: PRT
<213> ORGANISM: Mus musculus

<400> SEQUENCE: 10

```
Gln Gln Trp Ser Ser Asn Leu Thr
1               5
```

<210> SEQ ID NO 11
<211> LENGTH: 466
<212> TYPE: PRT
<213> ORGANISM: Mus musculus

<400> SEQUENCE: 11

```
Met Gly Trp Asn Trp Ile Phe Ile Leu Ile Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Thr Ser Gly Tyr Ser Phe
        35                  40                  45

Thr Gly Tyr Tyr Met Ser Trp Val Lys Gln Ser Pro Glu Lys Ser Leu
    50                  55                  60

Glu Trp Ile Gly Glu Ile Asn Pro Thr Thr Gly Gly Ser Thr Tyr Asn
65                  70                  75                  80
```

-continued

```
Gln Lys Phe Lys Ala Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Glu Gly Tyr Tyr Ser Gly Ile Ser Tyr Asp Ala
        115                 120                 125

Met Asp Tyr Trp Gly Gln Gly Thr Ser Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Gln Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Lys Pro Arg Glu Glu Gln Ile Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asn Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465
```

<210> SEQ ID NO 12
<211> LENGTH: 234
<212> TYPE: PRT

-continued

```
<213> ORGANISM: Mus musculus

<400> SEQUENCE: 12

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Ser Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Arg Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230


<210> SEQ ID NO 13
<211> LENGTH: 123
<212> TYPE: PRT
<213> ORGANISM: Mus musculus

<400> SEQUENCE: 13

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ser Phe Thr Gly Tyr
            20                  25                  30

Tyr Met Ser Trp Val Lys Gln Ser Pro Glu Lys Ser Leu Glu Trp Ile
        35                  40                  45

Gly Glu Ile Asn Pro Thr Thr Gly Gly Ser Thr Tyr Asn Gln Lys Phe
    50                  55                  60

Lys Ala Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Glu Gly Tyr Tyr Ser Gly Ile Ser Tyr Asp Ala Met Asp Tyr
            100                 105                 110

Trp Gly Gln Gly Thr Ser Val Thr Val Ser Ser
```

115 120

<210> SEQ ID NO 14
<211> LENGTH: 107
<212> TYPE: PRT
<213> ORGANISM: Mus musculus

<400> SEQUENCE: 14

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Asn Tyr
20 25 30

Leu Ser Trp Tyr Gln Gln Lys Pro Asp Gly Thr Val Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Arg
85 90 95

Thr Phe Gly Gly Gly Thr Lys Leu Glu Ile Lys
100 105

<210> SEQ ID NO 15
<211> LENGTH: 8
<212> TYPE: PRT
<213> ORGANISM: Mus musculus

<400> SEQUENCE: 15

Gly Tyr Ser Phe Thr Gly Tyr Tyr
1 5

<210> SEQ ID NO 16
<211> LENGTH: 8
<212> TYPE: PRT
<213> ORGANISM: Mus musculus

<400> SEQUENCE: 16

Ile Asn Pro Thr Thr Gly Gly Ser
1 5

<210> SEQ ID NO 17
<211> LENGTH: 16
<212> TYPE: PRT
<213> ORGANISM: Mus musculus

<400> SEQUENCE: 17

Ala Arg Glu Gly Tyr Tyr Ser Gly Ile Ser Tyr Asp Ala Met Asp Tyr
1 5 10 15

<210> SEQ ID NO 18
<211> LENGTH: 6
<212> TYPE: PRT
<213> ORGANISM: Mus musculus

<400> SEQUENCE: 18

Gln Asp Ile Ser Asn Tyr
1 5

<210> SEQ ID NO 19
<211> LENGTH: 3
<212> TYPE: PRT

-continued

<213> ORGANISM: Mus musculus

<400> SEQUENCE: 19

Tyr Thr Ser
1

<210> SEQ ID NO 20
<211> LENGTH: 9
<212> TYPE: PRT
<213> ORGANISM: Mus musculus

<400> SEQUENCE: 20

Gln Gln Gly Asn Thr Leu Pro Arg Thr
1 5

<210> SEQ ID NO 21
<211> LENGTH: 472
<212> TYPE: PRT
<213> ORGANISM: Mus musculus

<400> SEQUENCE: 21

```
Met Gly Trp Asn Trp Ile Phe Ile Leu Ile Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Tyr Met Asn Trp Val Lys Gln Ser Pro Glu Lys Ser Leu
    50                  55                  60

Glu Trp Ile Gly Glu Ile Asn Pro Thr Thr Gly Gly Thr Thr Tyr Asn
65                  70                  75                  80

Gln Lys Phe Lys Ala Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Leu His Tyr Asp Tyr Asp Gly Val Gly Tyr Ala
        115                 120                 125

Met Asp Tyr Trp Gly Gln Gly Thr Ser Val Thr Val Ser Ser Ala Thr
    130                 135                 140

Thr Thr Ala Pro Ser Val Tyr Pro Leu Val Pro Gly Cys Gly Asp Thr
145                 150                 155                 160

Ser Gly Ser Ser Val Thr Leu Gly Cys Leu Val Lys Gly Tyr Phe Pro
                165                 170                 175

Glu Pro Val Thr Val Lys Trp Asn Tyr Gly Ala Leu Ser Ser Gly Val
            180                 185                 190

Arg Thr Val Ser Ser Val Leu Gln Ser Gly Phe Tyr Ser Leu Ser Ser
        195                 200                 205

Leu Val Thr Val Pro Ser Ser Thr Trp Pro Ser Gln Thr Val Ile Cys
    210                 215                 220

Asn Val Ala His Pro Ala Ser Lys Thr Glu Leu Ile Lys Arg Ile Glu
225                 230                 235                 240

Pro Arg Ile Pro Lys Pro Ser Thr Pro Pro Gly Ser Ser Cys Pro Pro
                245                 250                 255

Gly Asn Ile Leu Gly Gly Pro Ser Val Phe Ile Phe Pro Pro Lys Pro
            260                 265                 270

Lys Asp Ala Leu Met Ile Ser Leu Thr Pro Lys Val Thr Cys Val Val
        275                 280                 285
```

Val Asp Val Ser Glu Asp Asp Pro Asp Val His Val Ser Trp Phe Val
290 295 300

Asp Asn Lys Glu Val His Thr Ala Trp Thr Gln Pro Arg Glu Ala Gln
305 310 315 320

Tyr Asn Ser Thr Phe Arg Val Val Ser Ala Leu Pro Ile Gln His Gln
325 330 335

Asp Trp Met Arg Gly Lys Glu Phe Lys Cys Lys Val Asn Asn Lys Ala
340 345 350

Leu Pro Ala Pro Ile Glu Arg Thr Ile Ser Lys Pro Lys Gly Arg Ala
355 360 365

Gln Thr Pro Gln Val Tyr Thr Ile Pro Pro Pro Arg Glu Gln Met Ser
370 375 380

Lys Lys Lys Val Ser Leu Thr Cys Leu Val Thr Asn Phe Phe Ser Glu
385 390 395 400

Ala Ile Ser Val Glu Trp Glu Arg Asn Gly Glu Leu Glu Gln Asp Tyr
405 410 415

Lys Asn Thr Pro Pro Ile Leu Asp Ser Asp Gly Thr Tyr Phe Leu Tyr
420 425 430

Ser Lys Leu Thr Val Asp Thr Asp Ser Trp Leu Gln Gly Glu Ile Phe
435 440 445

Thr Cys Ser Val Val His Glu Ala Leu His Asn His His Thr Gln Lys
450 455 460

Asn Leu Ser Arg Ser Pro Gly Lys
465 470

<210> SEQ ID NO 22
<211> LENGTH: 234
<212> TYPE: PRT
<213> ORGANISM: Mus musculus

<400> SEQUENCE: 22

Met Glu Ser Gln Ile Gln Val Phe Val Phe Val Phe Leu Trp Leu Ser
1 5 10 15

Gly Val Asp Gly Asp Ile Val Met Thr Gln Ser His Lys Phe Met Ser
20 25 30

Thr Ser Val Gly Asp Arg Val Ser Ile Thr Cys Lys Ala Ser Gln Asp
35 40 45

Val Ser Thr Ala Val Ala Trp Tyr Gln Gln Lys Pro Gly Gln Ser Pro
50 55 60

Lys Leu Leu Ile Tyr Ser Ala Ser Tyr Arg Tyr Thr Gly Val Pro Ala
65 70 75 80

Arg Phe Thr Gly Ser Gly Ser Gly Thr Asp Phe Thr Phe Thr Ile Ser
85 90 95

Ser Val Gln Ala Glu Asp Leu Ala Val Tyr Tyr Cys Gln Gln His Tyr
100 105 110

Ser Thr Pro Pro Thr Phe Gly Gly Gly Thr Lys Leu Glu Ile Lys Arg
115 120 125

Ala Asp Ala Ala Pro Thr Val Ser Ile Phe Pro Pro Ser Ser Glu Gln
130 135 140

Leu Thr Ser Gly Gly Ala Ser Val Val Cys Phe Leu Asn Asn Phe Tyr
145 150 155 160

Pro Lys Asp Ile Asn Val Lys Trp Lys Ile Asp Gly Ser Glu Arg Gln
165 170 175

Asn Gly Val Leu Asn Ser Trp Thr Asp Gln Asp Ser Lys Asp Ser Thr

-continued

```
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 23
<211> LENGTH: 123
<212> TYPE: PRT
<213> ORGANISM: Mus musculus

<400> SEQUENCE: 23

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met Asn Trp Val Lys Gln Ser Pro Glu Lys Ser Leu Glu Trp Ile
        35                  40                  45

Gly Glu Ile Asn Pro Thr Thr Gly Gly Thr Thr Tyr Asn Gln Lys Phe
    50                  55                  60

Lys Ala Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Leu His Tyr Asp Tyr Asp Gly Val Gly Tyr Ala Met Asp Tyr
            100                 105                 110

Trp Gly Gln Gly Thr Ser Val Thr Val Ser Ser
        115                 120
```

<210> SEQ ID NO 24
<211> LENGTH: 106
<212> TYPE: PRT
<213> ORGANISM: Mus musculus

<400> SEQUENCE: 24

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Ala Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                85                  90                  95

Thr Phe Gly Gly Gly Thr Lys Leu Glu Ile
            100                 105
```

<210> SEQ ID NO 25
<211> LENGTH: 8
<212> TYPE: PRT
<213> ORGANISM: Mus musculus

<400> SEQUENCE: 25

Gly Tyr Ser Phe Thr Gly Tyr Tyr
1 5

<210> SEQ ID NO 26
<211> LENGTH: 7
<212> TYPE: PRT
<213> ORGANISM: Mus musculus

<400> SEQUENCE: 26

Asn Pro Thr Thr Gly Gly Thr
1 5

<210> SEQ ID NO 27
<211> LENGTH: 16
<212> TYPE: PRT
<213> ORGANISM: Mus musculus

<400> SEQUENCE: 27

Ala Arg Leu His Tyr Asp Tyr Asp Gly Val Gly Tyr Ala Met Asp Tyr
1 5 10 15

<210> SEQ ID NO 28
<211> LENGTH: 6
<212> TYPE: PRT
<213> ORGANISM: Mus musculus

<400> SEQUENCE: 28

Gln Asp Val Ser Thr Ala
1 5

<210> SEQ ID NO 29
<211> LENGTH: 3
<212> TYPE: PRT
<213> ORGANISM: Mus musculus

<400> SEQUENCE: 29

Ser Ala Ser
1

<210> SEQ ID NO 30
<211> LENGTH: 9
<212> TYPE: PRT
<213> ORGANISM: Mus musculus

<400> SEQUENCE: 30

Gln Gln His Tyr Ser Thr Pro Pro Thr
1 5

<210> SEQ ID NO 31
<211> LENGTH: 10
<212> TYPE: PRT
<213> ORGANISM: Homo sapiens

<400> SEQUENCE: 31

Val Asn Asp Lys Thr Arg Thr Gln Arg Ile
1 5 10

<210> SEQ ID NO 32
<211> LENGTH: 15
<212> TYPE: PRT
<213> ORGANISM: Artificial
<220> FEATURE:
<223> OTHER INFORMATION: 15 amino acid peptide for epitope mapping

<400> SEQUENCE: 32

Gln Glu Trp Arg Cys Val Asn Asp Lys Thr Arg Thr Gln Arg Ile
1 5 10 15

<210> SEQ ID NO 33
<211> LENGTH: 15
<212> TYPE: PRT
<213> ORGANISM: Artificial
<220> FEATURE:
<223> OTHER INFORMATION: 15 amino acid peptide for epitope mapping

<400> SEQUENCE: 33

Glu Trp Arg Cys Val Asn Asp Lys Thr Arg Thr Gln Arg Ile Gln
1 5 10 15

<210> SEQ ID NO 34
<211> LENGTH: 15
<212> TYPE: PRT
<213> ORGANISM: Artificial
<220> FEATURE:
<223> OTHER INFORMATION: 15 amino acid peptide for epitope mapping

<400> SEQUENCE: 34

Trp Arg Cys Val Asn Asp Lys Thr Arg Thr Gln Arg Ile Gln Leu
1 5 10 15

<210> SEQ ID NO 35
<211> LENGTH: 15
<212> TYPE: PRT
<213> ORGANISM: Artificial
<220> FEATURE:
<223> OTHER INFORMATION: 15 amino acid peptide for epitope mapping

<400> SEQUENCE: 35

Arg Cys Val Asn Asp Lys Thr Arg Thr Gln Arg Ile Gln Leu Gln
1 5 10 15

<210> SEQ ID NO 36
<211> LENGTH: 15
<212> TYPE: PRT
<213> ORGANISM: Artificial
<220> FEATURE:
<223> OTHER INFORMATION: 15 amino acid peptide for epitope mapping

<400> SEQUENCE: 36

Cys Val Asn Asp Lys Thr Arg Thr Gln Arg Ile Gln Leu Gln Cys
1 5 10 15

<210> SEQ ID NO 37
<211> LENGTH: 15
<212> TYPE: PRT
<213> ORGANISM: Artificial
<220> FEATURE:
<223> OTHER INFORMATION: 15 amino acid peptide for epitope mapping

<400> SEQUENCE: 37

Val Asn Asp Lys Thr Arg Thr Gln Arg Ile Gln Leu Gln Cys Gln
1 5 10 15

<210> SEQ ID NO 38
<211> LENGTH: 467
<212> TYPE: PRT
<213> ORGANISM: Mus musculus

<400> SEQUENCE: 38

Met Lys Cys Ser Trp Val Ile Phe Phe Leu Met Ala Val Val Ile Gly
1 5 10 15

-continued

```
Val Asn Ser Glu Val Gln Leu Gln Gln Ser Gly Ala Glu Leu Val Arg
            20                  25                  30

Pro Gly Ala Ser Val Lys Leu Ser Cys Thr Ala Ser Gly Phe Asn Ile
        35                  40                  45

Lys Asp Asp Tyr Met His Trp Val Lys Gln Arg Pro Glu Gln Gly Leu
    50                  55                  60

Glu Trp Ile Gly Trp Ile Asp Pro Glu Asn Gly Asp Thr Glu Tyr Ala
65                  70                  75                  80

Ser Lys Phe Gln Gly Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ile Thr Pro Tyr Tyr Tyr Gly Ser Ser Phe Ser Tyr Trp
        115                 120                 125

Tyr Phe Asp Val Trp Gly Thr Gly Thr Thr Val Thr Val Ser Ser Ala
    130                 135                 140

Lys Thr Thr Pro Pro Ser Val Tyr Pro Leu Ala Pro Gly Ser Ala Ala
145                 150                 155                 160

Gln Thr Asn Ser Met Val Thr Leu Gly Cys Leu Val Lys Gly Tyr Phe
                165                 170                 175

Pro Glu Pro Val Thr Val Thr Trp Asn Ser Gly Ser Leu Ser Ser Gly
            180                 185                 190

Val His Thr Phe Pro Ala Val Leu Gln Ser Asp Leu Tyr Thr Leu Ser
        195                 200                 205

Ser Ser Val Thr Val Pro Ser Ser Thr Trp Pro Ser Gln Thr Val Thr
    210                 215                 220

Cys Asn Val Ala His Pro Ala Ser Ser Thr Lys Val Asp Lys Lys Ile
225                 230                 235                 240

Val Pro Arg Asp Cys Gly Cys Lys Pro Cys Ile Cys Thr Val Pro Glu
                245                 250                 255

Val Ser Ser Val Phe Ile Phe Pro Pro Lys Pro Lys Asp Val Leu Thr
            260                 265                 270

Ile Thr Leu Thr Pro Lys Val Thr Cys Val Val Val Asp Ile Ser Lys
        275                 280                 285

Asp Asp Pro Glu Val Gln Phe Ser Trp Phe Val Asp Asp Val Glu Val
    290                 295                 300

His Thr Ala Gln Thr Lys Pro Arg Glu Glu Gln Ile Asn Ser Thr Phe
305                 310                 315                 320

Arg Ser Val Ser Glu Leu Pro Ile Met His Gln Asp Trp Leu Asn Gly
                325                 330                 335

Lys Glu Phe Lys Cys Arg Val Asn Ser Ala Ala Phe Pro Ala Pro Ile
            340                 345                 350

Glu Lys Thr Ile Ser Lys Thr Lys Gly Arg Pro Lys Ala Pro Gln Val
        355                 360                 365

Tyr Thr Ile Pro Pro Pro Lys Glu Gln Met Ala Lys Asp Lys Val Ser
    370                 375                 380

Leu Thr Cys Met Ile Thr Asn Phe Phe Pro Glu Asp Ile Thr Val Glu
385                 390                 395                 400

Trp Gln Trp Asn Gly Gln Pro Ala Glu Asn Tyr Lys Asn Thr Gln Pro
                405                 410                 415

Ile Met Asp Thr Asp Gly Ser Tyr Phe Val Tyr Ser Lys Leu Asn Val
            420                 425                 430
```

```
Gln Lys Ser Asn Trp Glu Ala Gly Asn Thr Phe Thr Cys Ser Val Leu
        435                 440                 445

His Glu Gly Leu His Asn His His Thr Glu Lys Ser Leu Ser His Ser
    450                 455                 460

Pro Gly Lys
465


<210> SEQ ID NO 39
<211> LENGTH: 239
<212> TYPE: PRT
<213> ORGANISM: Mus musculus

<400> SEQUENCE: 39

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Arg Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235


<210> SEQ ID NO 40
<211> LENGTH: 124
<212> TYPE: PRT
<213> ORGANISM: Mus musculus

<400> SEQUENCE: 40

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Glu Trp Ile
        35                  40                  45
```

-continued

```
Gly Trp Ile Asp Pro Glu Asn Gly Asp Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ile Thr Pro Tyr Tyr Tyr Gly Ser Ser Phe Ser Tyr Trp Tyr Phe Asp
            100                 105                 110

Val Trp Gly Thr Gly Thr Thr Val Thr Val Ser Ser
        115                 120


<210> SEQ ID NO 41
<211> LENGTH: 112
<212> TYPE: PRT
<213> ORGANISM: Mus musculus

<400> SEQUENCE: 41

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110


<210> SEQ ID NO 42
<211> LENGTH: 8
<212> TYPE: PRT
<213> ORGANISM: Mus musculus

<400> SEQUENCE: 42

Gly Phe Asn Ile Lys Asp Asp Tyr
1               5


<210> SEQ ID NO 43
<211> LENGTH: 8
<212> TYPE: PRT
<213> ORGANISM: Mus musculus

<400> SEQUENCE: 43

Ile Asp Pro Glu Asn Gly Asp Thr
1               5


<210> SEQ ID NO 44
<211> LENGTH: 17
<212> TYPE: PRT
<213> ORGANISM: Mus musculus

<400> SEQUENCE: 44

Ile Thr Pro Tyr Tyr Tyr Gly Ser Ser Phe Ser Tyr Trp Tyr Phe Asp
1               5                   10                  15

Val
```

-continued

<210> SEQ ID NO 45
<211> LENGTH: 11
<212> TYPE: PRT
<213> ORGANISM: Mus musculus

<400> SEQUENCE: 45

```
Gln Ser Leu Leu Asp Ser Asp Gly Lys Thr Tyr
1               5                   10
```

<210> SEQ ID NO 46
<211> LENGTH: 3
<212> TYPE: PRT
<213> ORGANISM: Mus musculus

<400> SEQUENCE: 46

```
Leu Val Ser
1
```

<210> SEQ ID NO 47
<211> LENGTH: 9
<212> TYPE: PRT
<213> ORGANISM: Mus musculus

<400> SEQUENCE: 47

```
Trp Gln Gly Thr His Phe Pro Arg Thr
1               5
```

<210> SEQ ID NO 48
<211> LENGTH: 455
<212> TYPE: PRT
<213> ORGANISM: Mus musculus

<400> SEQUENCE: 48

```
Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Ile Thr
        35                  40                  45

Ser Gly Tyr Tyr Trp Asn Trp Ile Arg Gln Phe Pro Gly Asn Lys Leu
    50                  55                  60

Glu Trp Met Gly Cys Ile Ser Tyr Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
            100                 105                 110

Tyr Cys Ala Arg Gly Gly Leu Leu Trp Gly Gln Gly Thr Thr Leu Thr
        115                 120                 125

Val Ser Ser Ala Lys Thr Thr Pro Pro Ser Val Tyr Pro Leu Ala Pro
    130                 135                 140

Gly Ser Ala Ala Gln Thr Asn Ser Met Val Thr Leu Gly Cys Leu Val
145                 150                 155                 160

Lys Gly Tyr Phe Pro Glu Pro Val Thr Val Thr Trp Asn Ser Gly Ser
                165                 170                 175

Leu Ser Ser Gly Val His Thr Phe Pro Ala Val Leu Gln Ser Asp Leu
            180                 185                 190

Tyr Thr Leu Ser Ser Ser Val Thr Val Pro Ser Ser Thr Trp Pro Ser
        195                 200                 205
```

-continued

Gln Thr Val Thr Cys Asn Val Ala His Pro Ala Ser Ser Thr Lys Val
    210                 215                 220

Asp Lys Lys Ile Val Pro Arg Asp Cys Gly Cys Lys Pro Cys Ile Cys
225                 230                 235                 240

Thr Val Pro Glu Val Ser Ser Val Phe Ile Phe Pro Pro Lys Pro Lys
                245                 250                 255

Asp Val Leu Thr Ile Thr Leu Thr Pro Lys Val Thr Cys Val Val Val
            260                 265                 270

Asp Ile Ser Lys Asp Asp Pro Glu Val Gln Phe Ser Trp Phe Val Asp
        275                 280                 285

Asp Val Glu Val His Thr Ala Gln Thr Lys Pro Arg Glu Glu Gln Ile
    290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Pro Lys Glu Gln Met Ala Lys
        355                 360                 365

Asp Lys Val Ser Leu Thr Cys Met Ile Thr Asn Phe Phe Pro Glu Asp
    370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
                405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His His Thr Glu Lys Ser
        435                 440                 445

Leu Ser His Ser Pro Gly Lys
    450                 455

<210> SEQ ID NO 49
<211> LENGTH: 236
<212> TYPE: PRT
<213> ORGANISM: Mus musculus

<400> SEQUENCE: 49

Met Asp Met Arg Val Pro Ala His Val Phe Gly Phe Leu Leu Leu Trp
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Glu Ile Ser Gly Tyr Leu Ser Trp Leu Gln Gln Lys Pro Asp Gly
    50                  55                  60

Asn Ile Lys Arg Leu Ile Tyr Ala Ala Ser Thr Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Arg Leu Glu Ser Glu Asp Phe Ala Asp Tyr Tyr Cys Leu Gln
            100                 105                 110

Tyr Ala Ser Tyr Pro Trp Thr Phe Gly Gly Gly Thr Lys Leu Glu Ile

-continued

```
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235


<210> SEQ ID NO 50
<211> LENGTH: 113
<212> TYPE: PRT
<213> ORGANISM: Mus musculus

<400> SEQUENCE: 50

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Cys Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Gly Gly Leu Leu Trp Gly Gln Gly Thr Thr Leu Thr Val Ser
            100                 105                 110

Ser


<210> SEQ ID NO 51
<211> LENGTH: 107
<212> TYPE: PRT
<213> ORGANISM: Mus musculus

<400> SEQUENCE: 51

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Asn Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Arg Leu Glu Ser
65                  70                  75                  80

Glu Asp Phe Ala Asp Tyr Tyr Cys Leu Gln Tyr Ala Ser Tyr Pro Trp
                85                  90                  95
```

-continued

```
Thr Phe Gly Gly Gly Thr Lys Leu Glu Ile Lys
            100                 105


<210> SEQ ID NO 52
<211> LENGTH: 9
<212> TYPE: PRT
<213> ORGANISM: Mus musculus

<400> SEQUENCE: 52

Gly Tyr Ser Ile Thr Ser Gly Tyr Tyr
1               5


<210> SEQ ID NO 53
<211> LENGTH: 7
<212> TYPE: PRT
<213> ORGANISM: Mus musculus

<400> SEQUENCE: 53

Ile Ser Tyr Asp Gly Ser Asn
1               5


<210> SEQ ID NO 54
<211> LENGTH: 6
<212> TYPE: PRT
<213> ORGANISM: Mus musculus

<400> SEQUENCE: 54

Ala Arg Gly Gly Leu Leu
1               5


<210> SEQ ID NO 55
<211> LENGTH: 6
<212> TYPE: PRT
<213> ORGANISM: Mus musculus

<400> SEQUENCE: 55

Glu Ile Ser Gly Tyr Leu
1               5


<210> SEQ ID NO 56
<211> LENGTH: 3
<212> TYPE: PRT
<213> ORGANISM: Mus musculus

<400> SEQUENCE: 56

Ala Ala Ser
1


<210> SEQ ID NO 57
<211> LENGTH: 9
<212> TYPE: PRT
<213> ORGANISM: Mus musculus

<400> SEQUENCE: 57

Leu Gln Tyr Ala Ser Tyr Pro Trp Thr
1               5
```